(12) United States Patent
Krusemark et al.

(10) Patent No.: US 12,162,955 B2
(45) Date of Patent: *Dec. 10, 2024

(54) CBX8 CHROMDOMAIN INHIBITORS AND THE USES THEREOF

(71) Applicant: Purdue Research Foundation, West Lafayette, IN (US)

(72) Inventors: Casey J. Krusemark, West Lafayette, IN (US); Emily C. Dykhuizen, West Lafayette, IN (US); Sijie Wang, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/103,694

(22) Filed: Jan. 31, 2023

(65) Prior Publication Data
US 2023/0257421 A1 Aug. 17, 2023

Related U.S. Application Data

(63) Continuation of application No. 16/894,036, filed on Jun. 5, 2020, now Pat. No. 11,566,046.

(60) Provisional application No. 62/858,606, filed on Jun. 7, 2019.

(51) Int. Cl.
| | | |
|---|---|---|
| *C07K 5/10* | (2006.01) | |
| *A61P 35/02* | (2006.01) | |
| *C07K 5/107* | (2006.01) | |
| *C07K 7/06* | (2006.01) | |
| *A61K 38/00* | (2006.01) | |

(52) U.S. Cl.
CPC .............. *C07K 7/06* (2013.01); *A61P 35/02* (2018.01); *C07K 5/1016* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 3,895,231 A | 7/1975 | Sodal et al. | |
| RE33,863 E | 3/1992 | Bowman et al. | |
| 5,436,446 A | 7/1995 | Jarrell et al. | |
| 5,689,111 A | 11/1997 | Dresch et al. | |
| 5,756,995 A | 5/1998 | Maswadeh et al. | |
| 5,856,671 A | 1/1999 | Henion et al. | |
| 6,040,575 A | 3/2000 | Whitehouse et al. | |
| 6,121,609 A | 9/2000 | Littlejohn | |
| 6,396,057 B1 | 5/2002 | Jarrell et al. | |
| 6,501,073 B1 | 12/2002 | Mylchreest et al. | |
| 6,518,581 B1 | 2/2003 | Dheandhanoo et al. | |
| 6,570,152 B1 | 5/2003 | Hoyes | |
| 6,777,672 B1 | 8/2004 | Park | |
| 8,304,718 B2 | 11/2012 | Ouyang et al. | |
| 8,680,464 B2 | 3/2014 | Hashimoto et al. | |
| 8,766,178 B2 | 7/2014 | Ouyang et al. | |
| 8,853,627 B2 | 10/2014 | Ouyang et al. | |
| 11,566,046 B2* | 1/2023 | Krusemark | C07K 5/1016 |
| 2002/0092979 A1 | 7/2002 | McCauley et al. | |
| 2002/0121598 A1 | 9/2002 | Park | |
| 2003/0020013 A1 | 1/2003 | Sakairi | |
| 2005/0269518 A1 | 12/2005 | Bajic et al. | |
| 2006/0051737 A1* | 3/2006 | Lange | C12Q 1/485 435/6.16 |
| 2006/0054805 A1 | 3/2006 | Flanagan et al. | |
| 2007/0018093 A1 | 1/2007 | Earm et al. | |
| 2013/0056633 A1 | 3/2013 | Hashimoto et al. | |
| 2013/0146759 A1 | 6/2013 | Ouyang et al. | |
| 2013/0280819 A1 | 10/2013 | Cooks et al. | |
| 2014/0051180 A1 | 2/2014 | Cooks et al. | |
| 2014/0138540 A1 | 5/2014 | Ouyang et al. | |

FOREIGN PATENT DOCUMENTS

| | | |
|---|---|---|
| EP | 08124518 | 5/1996 |
| EP | 09210965 | 8/1997 |
| WO | 2005/096720 A2 | 10/2005 |
| WO | 2009/023361 A2 | 2/2009 |

OTHER PUBLICATIONS

UniProt entry for Q6XVW3 (retrieved from https://www.uniprot.org/uniprot/Q6XVW3 on Apr. 27, 2021, 4 pages) (Year: 2021).*
Denton et al. ('Robustness of In Vitro Selection Assays of DNA-Encoded Peptidomimetic Ligands to CBX7 and CBX8' SLAS Discovery v23(5) 2018 pp. 417-428) (Year: 2018).*
Denton et al. (supplement for 'Robustness of In Vitro Selection Assays of DNA-Encoded Peptidomimetic Ligands to CBX7 and CBX8' SLAS Discovery v23(5) 2018, 12 pages) (Year: 2018).*
Denton publication date information (retrieved from https://pubmed.ncbi.nlm.nih.gov/29309209/ on Apr. 26, 2021, 2 pages) (Year: 2021).*
Simhadri et al. ('Chromodomain antagonists that target the polycomb-group methylysine reader protein chromobox homolog 7 (CBX7)' Journal of Medicinal Chemistry v57(7) 2014 pp. 2874-2883) (Year: 2014).*
Stuckey et al. ('Structure-activity relationships and kinetic studies of peptidic antagonists of CBX chromodomains' Journal of Medicinal Chemistry v59 2016 pp. 8913-8923) (Year: 2016).*
UniProt entry for Q6XVW3 (retrieved from https://www.uniprot.org/uniprot/Q6XVW3 on Apr. 27, 2021), 4 pages.
Wang, 2020, Optimization of ligands using focused DNA-encoded libraries to develop a selective, cell-permeable CBX8 chromodomain inhibitor ACS Chem Biol v15(1):112-131.

(Continued)

*Primary Examiner* — Ronald T Niebauer
(74) *Attorney, Agent, or Firm* — Brown Rudnick LLP; Adam M. Schoen

(57) ABSTRACT

The present invention relates to series of peptidomimetic compounds selectively targeting CBX8 of polycomb chromobox protein homolog proteins. Pharmaceutical compositions of those compounds and methods of using them in the treatment of diseases involved CBX8 pharmacology, including various cancers and leukemia, by administering therapeutically effective amounts of such compound alone or together with other therapeutics, are within the scope of this disclosure.

6 Claims, 16 Drawing Sheets

Specification includes a Sequence Listing.

(56) References Cited

OTHER PUBLICATIONS

Wang, 2021, A potent, selective CBX2 chromodomain ligand and its cellular activity during prostate cancer neuroendocrine differentiation, ChemBioChem v22, pp. 2335-2344.
Wilm, 1996, Analytical Properties of the Nanoelectrospray Ion Source, Anal. Chem. 68(1):1-8.
Written Opinion of the International Searching Authority as mailed on Mar. 25, 2009 in corresponding PCT application PCT/US2008/065245.
Yamashita, 1984, Electrospray Ion Source, Another Variation on the Free-Jet Theme, J. Phys. Chem. 88:4451-4459.
Zhang, 2018, CBX9 exhibits oncogenic activity via AKT/b-catenin activation in hepatocellular carcinoma, Cancer Research, 78(1)::51-63.
Zhou, 2003, Incorporation of a Ventri Device in Electrospray Ionization, Anal. Chem. 2003, 75, 5978-5983.
Ayton, 2003, Transformation of myeloid progenitors by MLL oncoproteins is dependent on Hoxa7 and Hoxa9. Genes Dev. 17, 2298-2307.
Beguelin, 2016, EZH2 and BCL6 Cooperate to Assemble CBX8-BCOR Complex to Repress Bivalent Promoters, Mediate Germinal Center Formation and Lymphomagenesis. Cancer Cell, 30(2), 197-213.
Bernt, 2011, MLL-rearranged leukemia is dependent on aberrant H3K79 methylation by DOTIL. Cancer cell, 20(1) 66-78.
Carroll, 1975, Atmospheric Pressure Ionization Mass Spectrometry: Corona Discharge Ion Source for Use in Liquid Chromatograph-Mass Spectrometer-Computer Analytical System Anal. Chem. 47(14):2369-2373.
Chen, 2006, Thermal production and reactions of organic ions at atmospheric pressure, Angewandte Chemie, International Edition, 45(22):3656-3660.
Chen, 2007, Neutral Fragment Mass Spectra via Ambient Thermal Dissociation of Peptide and Protein Ions, Journal of the American Chemical Society, 129(18):5880-5886.
Chou, 2011, The roles of EZH2 in cell lineage commitment. American Journal of Translational Research, 3(3), 243-250.
Chung, 2016, Cbx8 Acts Non-canonically with Wdr5 to Promote Mammary Tumorigenesis, Cell Reports, 16(2):472-486.
Cody, 2005, Versatile new ion source for the analysis of materials in open air under ambient conditions, Anal. Chem., 77(8):2297-2302.
Connelly, 2018, Engagement of DNA and H3K27me3 by the CBX8 chromodomain drives chromatin association, Nucleic acids research, 47(5):2289-2305.
Creppe, 2014, A Cbx8-containing polycomb complex facilitates the transition to gene activation during ES cell differentiation. PLoS genetics 10(2), 15 pages.
Denton, 2018, Robustness of In Vitro Selection Assays of DNA-Encoded Peptidomimetic Ligands to CBX7 and CBX8. SLAS Discovery, 23(5):417-428.
Denton, 2018, Supplemental Information: Robustness of In Vitro Selection Assays of DNA-Encoded Peptidomimetic Ligands to CBX7 and CBX8. SLAS Discovery, 12 pages.
Fenn, 1989, Electrospray Ionization for Mass Spectrometry of Large Biomolecules, Science, 246:64-71.
Franzini, 2014, DNA-Encoded Chemical Libraries: Advancing Beyond Conventional Small-Molecule Libraries, Accounts of Chemical Research, 47(4):1247-55.
Gao, 2006, Handheld rectilinear ion trap mass spectrometer. Anal. Chem. 78(17):5994-6002.
Gao, 2008, Breaking the Pumping Speed Barrier in Mass Spectrometry; Discontinuous Atmosheric Pressure Interface, 80(11):4026-4032.
Grim, 2002, Evaluation of Laser Desorption Mass Spectrometry and UV Accelerated Aging of Dyes on Paper as Tools for the Evaluation of a Questioned Document, J. Forensic Sci., 47(6):1265-1273.
Ifa, 2007, Forensic analysis of inks by imaging desorption electrospray ionization (DESI) mass spectrometry,. Analyst, 132:461-467.

International Preliminary Report on Patentability mailed Dec. 10, 2009 PCTUS2008065245.
International Search Report as mailed on Mar. 25, 2009 in corresponding PCT application PCT/US2008/065245.
Kaustov, 2011, Recognition and specificity determinants of the human Cbx Chromodomains, Journal of Biological Chemistry, 286(1):521-529.
Kim, 2016, Targeting EZH2 in cancer, Nature Medicine, 22(2):128-134.
Klauke, 2013, Polycomb Cbx family members mediate the blance between haematopoietic stem cell self-renewal and differentiation, Nature Cell Biology, 15(4):353-362.
Krusemark, 2016, Directed chemical evolution with an outsized genetic code, PloS one, 11.8:e0154765, 16 pages.
Kumar, 2004, Hoxa9 influences the phenotype byt not the incidence of MII-AF9 fusion gene leukemia, Blood, 103:1823-1828.
Kwang, 2006, A review of microvalves, Journal of Micromechanics and Microenfineering Mar. 24, 2006, 16:R13-R39.
Laiko, 2000, Atmospheric Pressue Matrix-Assisted Laser Desorption/Ionization Mass Spectrometry, Anal. Chem., 72:652-657.
Li, 2013, Altered expression of polycomb group genes in glioblastoma multiforme, PloS one, 8.11:e80970, 8 pages.
Loo, 1992, A New Approach for the Study of Gas-Phase Ion-Ion Reactions Using Electrospray Ionization,. Journal of the American Society for Mass Spectrometry 3:695-705.
Marian, 2018, Small molceule targeting of specific BAF (mSWI/SNF) complexes for HIV latency reversal, Cell chemical biology, 25(12):1443-1455.
Mills, 2010, Throwing the cancer switch: Reciprocal roles of polycomb and trithorax proteins, Nature Reviews Cancer, 10(10):669-682.
Milosevich, 2016, Selective Inhibition of CBX6: A Methyllysine Reader Protein in the Polycomb Family, ACS Medicinal Chemistry Letters, 7(2):139-144.
Morey, 2012, Nonoverlapping functions of the Polycomb group Cbx family of proteins in embryonic stem cells, Cell stem cell, 10(1):47-62.
Mueller, 2007, A role for the MLL fusion partner ENL in transcriptional elongation and chromatin modification, Blood, 110(13):4445-4454.
Pan, 2004, Nanoelectrospray Ionization of Protein Mixtures: Solution pH and Protein pI. Anal. Chem. 76(4):1165-1174.
Ren, 2015, Small-molecule modulators of methyl-lysine binding for the CBX7 chromodomain, Chemistry and Biology, 22(2):161-168.
Ren, 2016, Structure-Guided Discovery of Selective Antagonists for the Chromodomain of Polycomb Repressive Protein CBX7, Acs Medicinal Chemistry Letters, 7(6):601-605.
Santiago, 2011, Druggability of Methyl-Lysine Binding Sites, Journal of Computer-Aided Molecular Design, 25 (12):1171-1178.
Satz, 2016, Simulated screens of DNA encoded libraries: the potential influence of chemical synthesis fidelity on interpretation of structure-activity relationships, ACS combinatorial science, 18(7):415-424.
Sauvageau, 2010, Polycomb group proteins: Multi-faceted regulators of somatic stem cells and cancer, Cell Stem Cell, 7(3):299-313.
Shaffer, 1997, A Novel Ion Funnel for Focusing Ions at Elevated Pressure Using Electrospray Ionization Mass Spectrometry, Rapid Communications in Mass Spectrometry 11:1813-1817.
Shiea, 2005, Electrospray-assisted laser desorption/ionization mass spectrometry for direct ambient analysis of solids, Rapid Commun. Mass Spectrom, 19:3701-370.
Simhadri, 2016, Chromodomain Antagonists that Target the Polycomb-Group Methyllysine Reader Protein Chromobox Homolog 7 (CBx7), Journal of Medicinal Chemistry v57(7):2874-2883.
Stuckey, 2016, A cellular chemical probe targeting the chromodomains of Polycomb repressive complex1, Nature Chemical Biology, 12(3):180-187.
Stuckey, 2016, Structure-activity relationships and kinetic studies of peptidic antagonists of CBX chromodomains, Journal of Medicinal Chemistry, v59, pp. 8913-8923.
Takats, 2004, Thermal formation of serine octamer ions,. Chemical Communications, 444-445.

(56) References Cited

OTHER PUBLICATIONS

Takats, 2004, Mass Spectrometry Sampling Under Ambient Conditions with Desorption Electrospray Ionization, Science, 306:471-473.
Tan, 2011, CBX8, a Polycomb Group Protein, Is Essential for MLL-AF9-Induced Leukemogenesis, Cancer Cell, 20 (5):563-575.
Tanaka, 1988, Protein and Polymer Analyses up to m/z 100 000 by Laser Ionization Time-of-flight Mass Spectrometry, T. Rapid Commun. Mass Spectrom. 2(8), 151-153.

* cited by examiner

PSL2B P(-3) cap

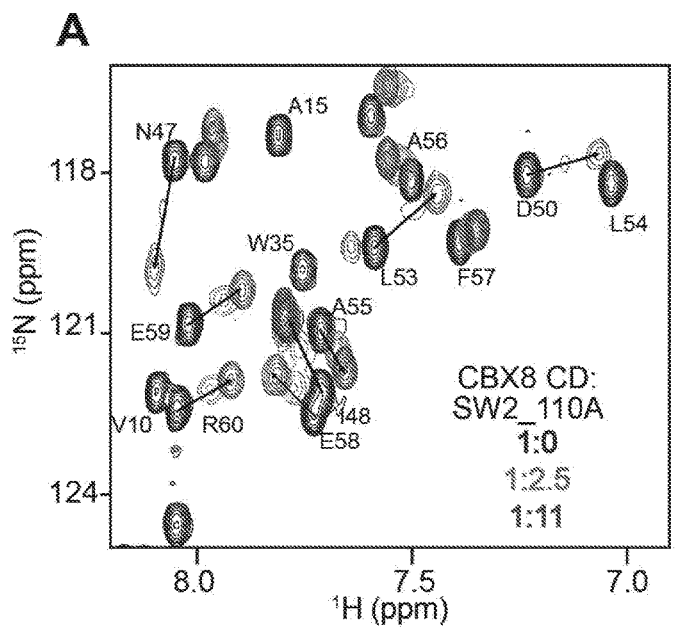
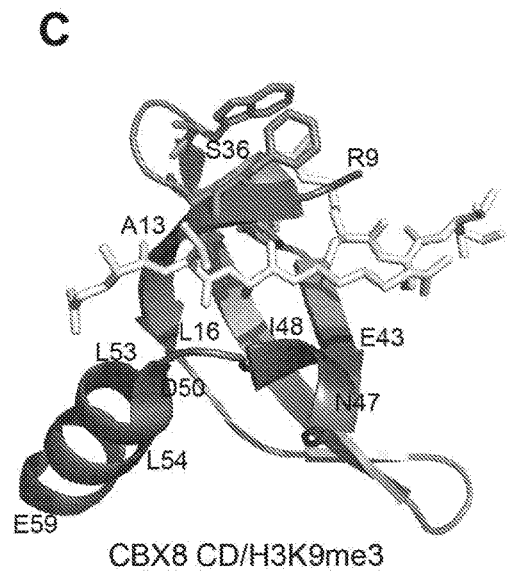
FIG. 4A
FIG. 4C
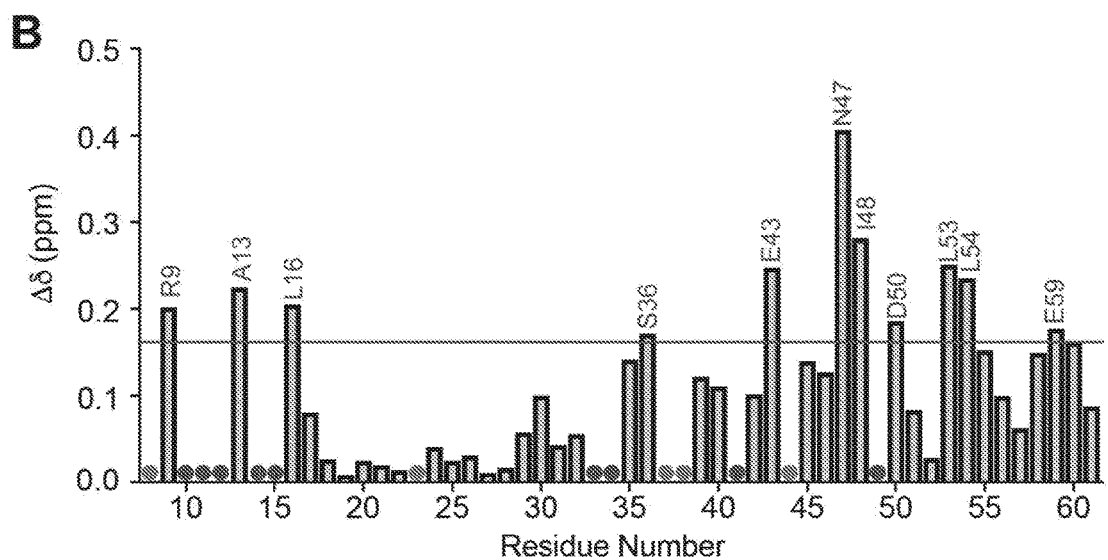
FIG. 4B

A

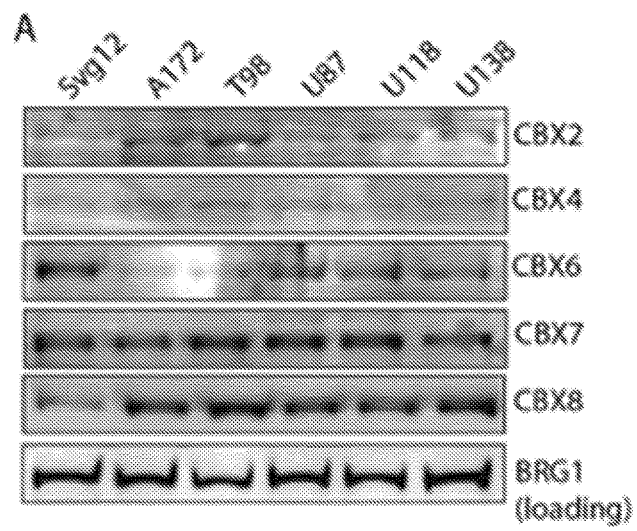
FIG. 8A
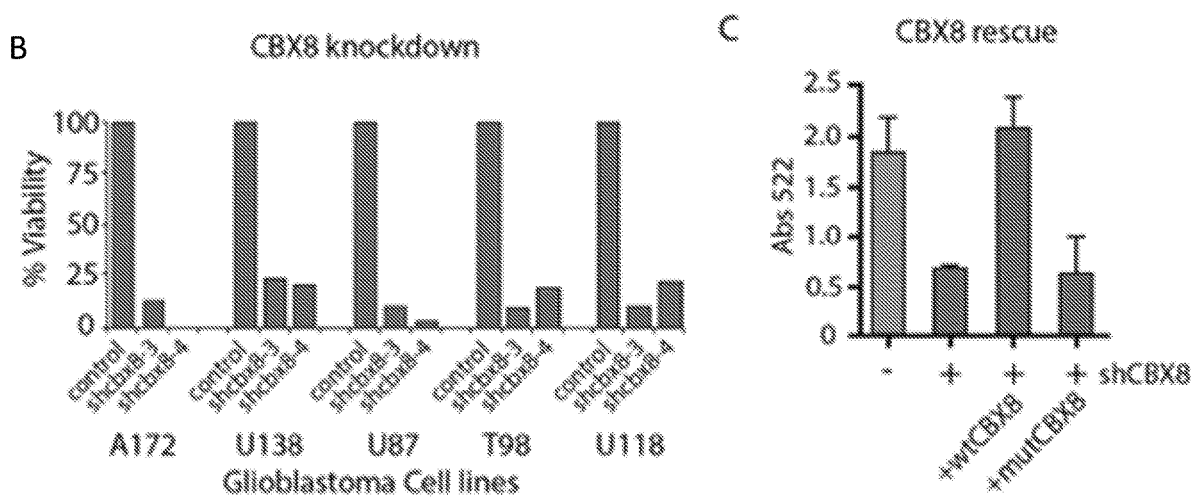
FIG. 8B
FIG. 8C

CBX8 CHROMDOMAIN INHIBITORS AND THE USES THEREOF

CROSS-REFERENCE TO RELATED APPLICATIONS

The present U.S. patent application is a continuation of U.S. nonprovisional application Ser. No. 16/894,036, filed Jun. 5, 2020, which is related to and claims the priority benefit of U.S. Provisional Patent Application Ser. No. 62/858,606, filed Jun. 7, 2019, the contents of each of which are hereby incorporated by reference in their entirety into this disclosure.

GOVERNMENT SUPPORT CLAUSE

This invention was made with government support under GM128894, 1NS101535 and CA207532, awarded by the National Institutes of Health. The government has certain rights in the invention.

STATEMENT OF SEQUENCE LISTING

A computer-readable form (CRF) of the Sequence Listing is submitted concurrently with this application. The file, entitled 68554-02_Seq_Listing_ST25_txt, is generated on Jun. 2, 2020. Applicant states that the content of the computer-readable form is the same and the information recorded in computer readable form is identical to the written sequence listing.

TECHNICAL FIELD

The present invention relates to series of peptidomimetic compounds selectively targeting CBX8 of polycomb chromobox protein homolog proteins. Pharmaceutical compositions of those compounds and methods of using them in the treatment of diseases involved CBX8 pharmacology, including various cancers and leukemia, by administering therapeutically effective amounts of such compound alone or together with other therapeutics, are within the scope of this disclosure.

BACKGROUND

This section introduces aspects that may help facilitate a better understanding of the disclosure. Accordingly, these statements are to be read in this light and are not to be understood as admissions about what is or is not prior art.

Polycomb Group (PcG) proteins are required for proper body segmentation in *Drosophila* through the repression of differentiation genes (Kennison, 1995). PcG proteins are similarly essential in determining body plan in mammals, and also for the maintenance of adult stem cells (M. Sauvageau and Sauvageau, 2010). PcG proteins are part of two distinct complexes, polycomb repressive complex 1 (PRC1) and polycomb repressive complex 2 (PRC2) (FIG. 1A). Canonical PRC1 function, as defined in *Drosophila*, begins with PRC2-mediated trimethylation of lysine 27 of histone 3 (H3K27me3), which recruits PRC1 via the chromodomain (ChD) of the CBX (chromobox homolog) subunit. PRC1 then compacts chromatin and ubiquitinates lysine 119 on histone H2A to promote transcriptional repression.

In mammals, all of the PRC1 subunits have mutually exclusive paralogs that emerged after the whole genome duplications that occurred during vertebrate evolution. As a result, PRC1 complexes are highly heterogeneous, although it is unclear how these closely related PRC1 complexes differentially regulate transcription (FIG. 1A) (Connelly and Dykhuizen, 2017). The CBX subunit can be one of five paralogs (CBX2, CBX4, CBX6, CBX7, CBX8) that shift in expression during development (Klauke et al., 2013), as well as cancer progression (Koppens and van Lohuizen, 2015; Mills, 2010). Studies in multiple cell types show that each paralog has unique, non-overlapping functions in development and in disease (Morey et al., 2012; Klauke et al., 2013).

CBX8 has recently emerged as a potential oncogenic target in multiple malignancies. It drives growth and is correlated with poor patient outcomes in lymphoma (Béguelin et al., 2016), hepatocellular carcinoma (Zhang et al., 2017), breast cancer (Chung et al., 2016) and leukemia with MLL translocations (Tan et al., 2011). CBX8's mode of action has been extensively studied at the level of genetics and cell biology, but the roles of distinct binding domains and potential druggable sites have not been explored. The chemical probes that are needed to study CBX8's roles in transcription and oncogenesis, and to explore its potential as a therapeutic target, have been lacking.

The ChDs of polycomb CBX proteins are considered "druggable" (Santiago, Nguyen, and Schapira, 2011). Yet, significant challenges exist in developing potent and selective chemical probes for the CBX ChDs. The first is that the wide, shallow binding pockets are difficult to target with traditional small molecules. Two reported small molecule ChD inhibitors target CBX7 (Ren et al., 2015; Ren et al., 2016) but display weak (~20 μM) affinity for CBX7 and over 10-fold weaker affinity for CBX8. Larger molecular weight, trimethyllysine-containing peptidomimetics (5-6-mers) developed for CBX4, CBX6, and CBX7 ChDs display much greater affinity (<1 μM); however, they have limited cell permeability (Stuckey, Dickson, et al., 2016; Milosevich and Hof, 2015; Simhadri et al., 2014).

The other daunting challenge lies in developing ChD inhibitors with specificity for one paralog over another. There is high sequence homology for the CBX ChDs, including both the Polycomb CBX ChDs (CBX 2,4,6,7,8) that recognize H3K27me3, and heterochromatin protein 1 (HP1) ChDs (CBX 1,3,5) that recognize H3K9me3 (Kaustov et al., 2011). Moderate selectivity has been achieved for CBX6 ChD, and CBX7/CBX4; (Milosevich et al., 2016; Stuckey, Dickson, et al., 2016). No ligand has been developed with selectivity for CBX8 ChD. There are unmet needs in developing selective ligands for CBX8 ChD as a potential method to fight for cancer.

Cancer is a group of most diverse diseases involving abnormal cell growth. Currently there are more than 100 types of identified cancer that affect human beings as well as animals. In 2016, there were an estimated 1,685,210 new human cancer cases diagnosed and 595,690 cancer deaths in the U.S. alone (Cancer Statistics 2016—American Cancer Society, Inc.). There are unmet and increasing needs for new and novel therapies for fighting cancers.

SUMMARY

The present invention relates to series of peptidomimetic compounds selectively targeting CBX8 of polycomb chromobox protein homolog proteins. Pharmaceutical compositions of those compounds and methods of using them in the treatment of diseases involved CBX8 pharmacology, including various cancers and leukemia, by administering therapeutically effective amounts of such compound alone or together with other therapeutics, are within the scope of this disclosure.

In some illustrative embodiments, this disclosure relates to a compound having the formula (I):

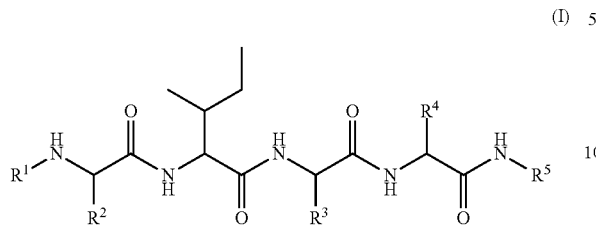

(I)

or a pharmaceutically acceptable salt thereof, wherein,
$R^1$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, heteroarylalkyl, or one to two amino acid residues; each of which is optionally substituted;
$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^3$ is an alkylamino, alkenylamino, cycloalkylamino, cycloalkenylamino, heteroalkylamino, or heteroalkenylamino; each of which is optionally substituted;
$R^4$ is heteroalkyl, heteroalkenyl, heterocyclyl; and
$R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted.

In some other illustrative embodiments, this disclosure relates to a compound having the formula (II):

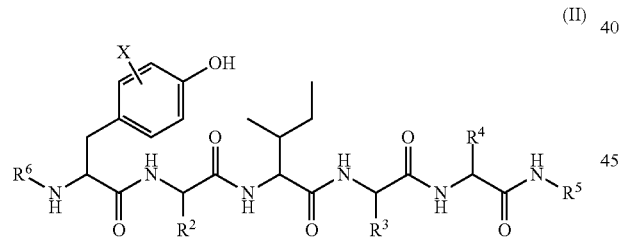

(II)

wherein X represents four substituents, independently, hydrogen or halo;
$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^3$ is an alkylamino, alkenylamino, cycloalkylamino, cycloalkenylamino, heteroalkylamino, or heteroalkenylamino; each of which is optionally substituted;
$R^4$ is heteroalkyl, heteroalkenyl, heterocyclyl;
$R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted; and
$R^6$ is an alkyl, alkenyl, alkynyl, cycloalkyl, cycloalkenyl, heterocyclyl, aryl, heteroaryl, arylalkyl, or heteroarylalkyl, each of which is optionally substituted.

In some other illustrative embodiments, this disclosure relates to a compound having the formula (III):

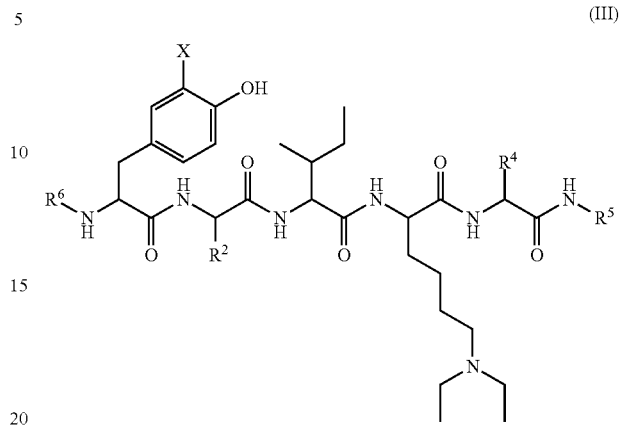

(III)

wherein X represents a halo;
$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^4$ is heteroalkyl, heteroalkenyl, heterocyclyl;
$R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted;
and
$R^6$ is an alkyl, alkenyl, alkynyl, cycloalkyl, cycloalkenyl, heterocyclyl, aryl, heteroaryl, arylalkyl, or heteroarylalkyl, each of which is optionally substituted.

In some other illustrative embodiments, this disclosure relates to a compound having the formula (IV):

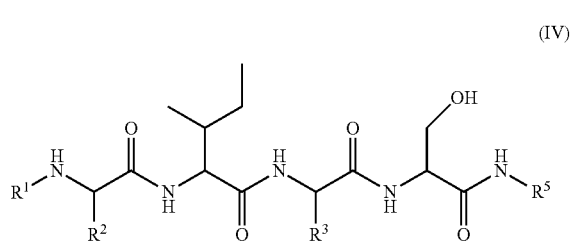

(IV)

wherein $R^1$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^3$ is an alkylamino, alkenylamino, cycloalkylamino, cycloalkenylamino, heteroalkylamino, or heteroalkenylamino; each of which is optionally substituted; and
$R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted.

In some preferred embodiments, this disclosure relates to a compound having the following formula:
SEQ ID NO: 1
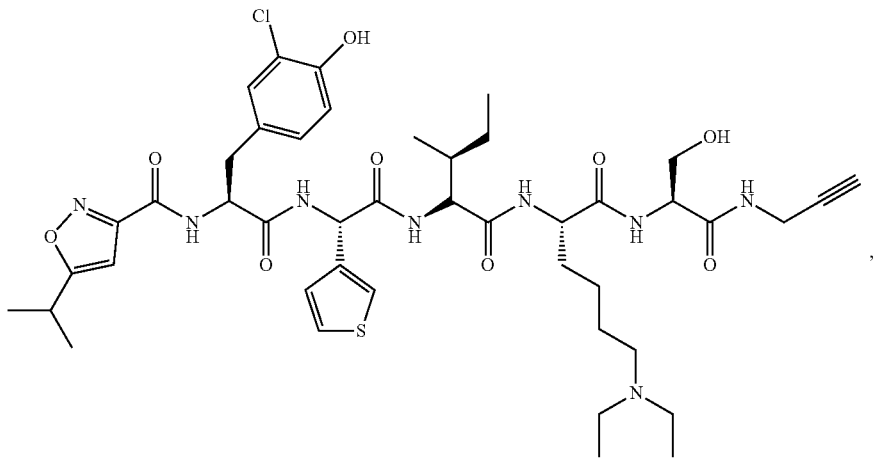
SW2_104A
SEQ ID NO: 2
SEQ ID NO: 3
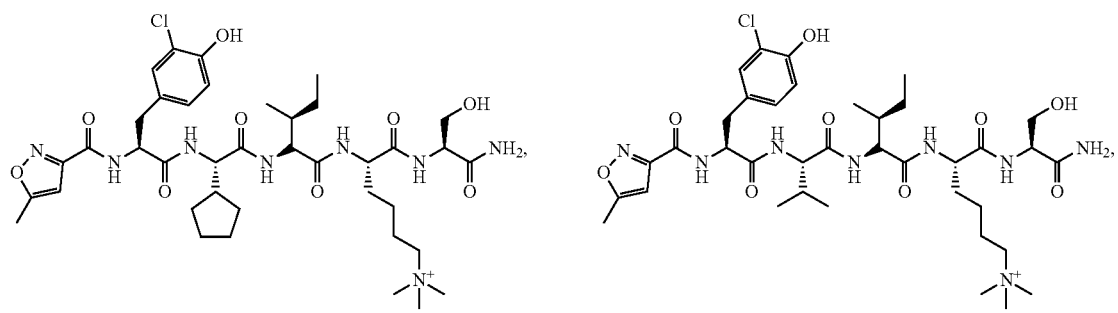
KED98
KED97
SEQ ID NO: 4
SEQ ID NO: 5
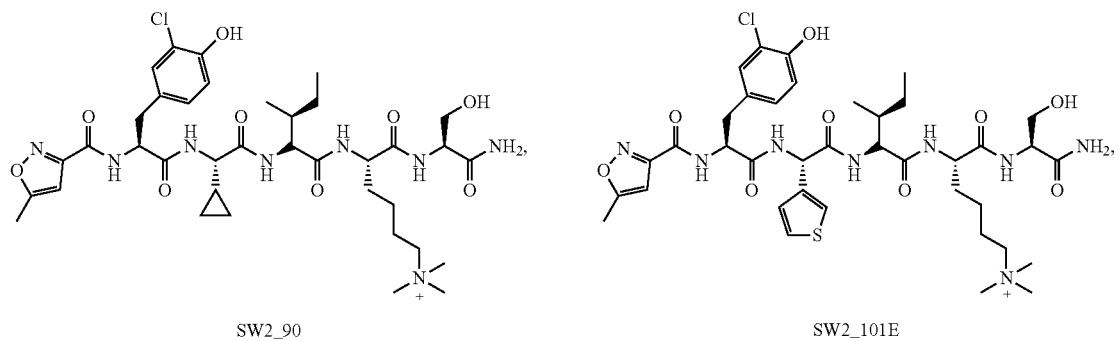
SW2_90
SW2_101E SEQ ID NO: 6
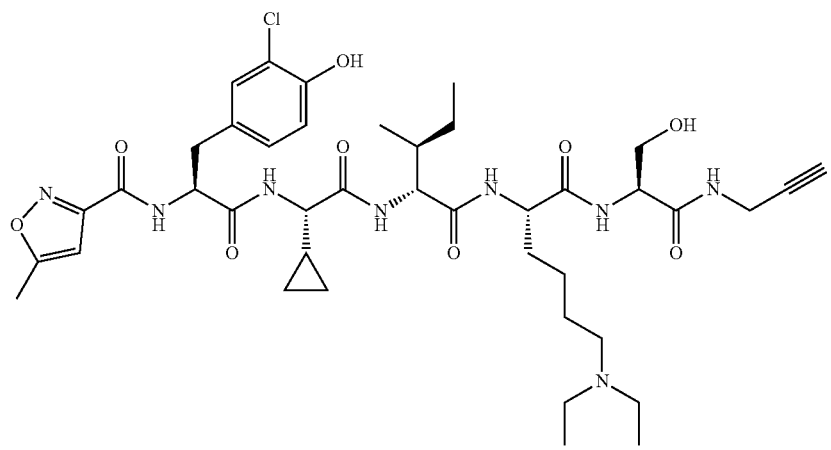
SW2_90L
SEQ ID NO: 7
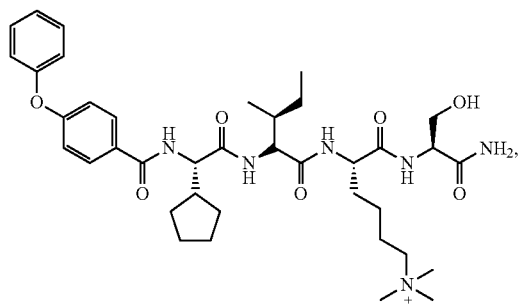
SW2_101B
SEQ ID NO: 8
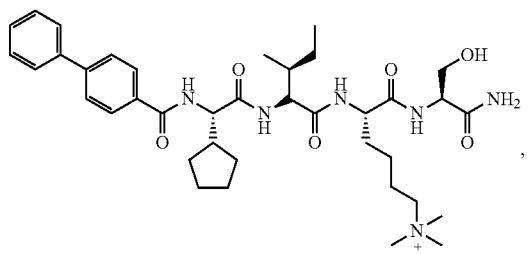
SW2_89
SEQ ID NO: 9
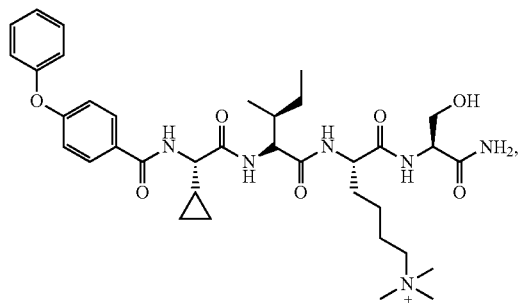
SW2_101F
SEQ ID NO: 10
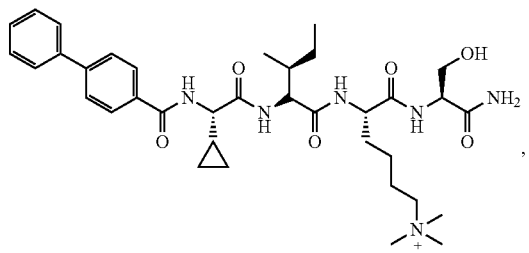
SW2_101A

SEQ ID NO: 11

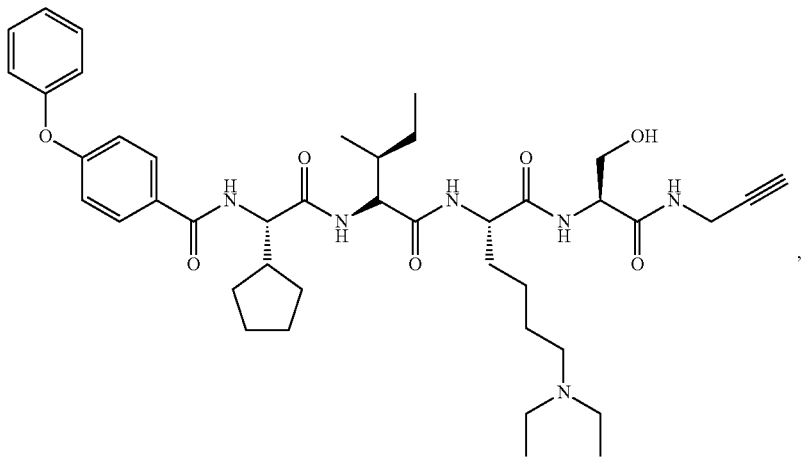
SW2_110A

SEQ ID NO: 12

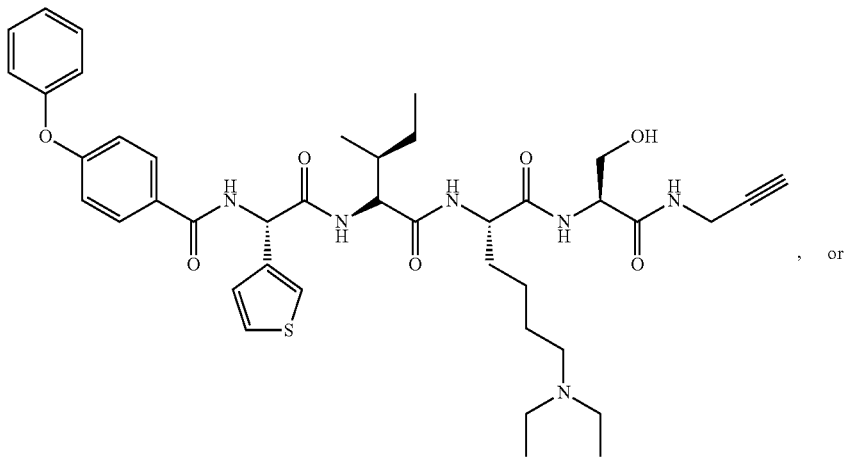
SW2_110B , or (SEQ ID NO: 13)

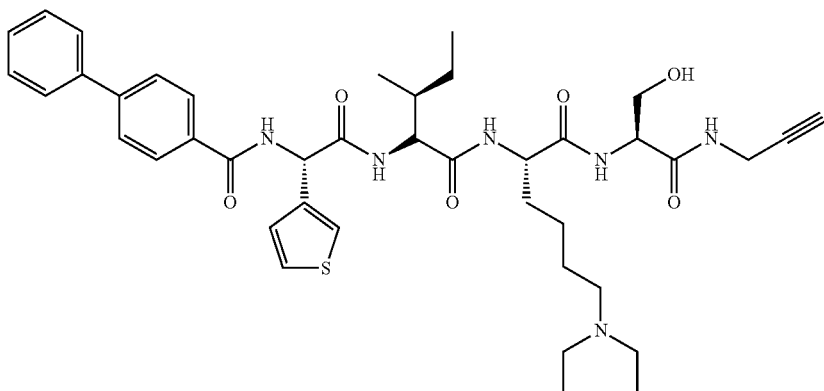
SW2_104B

In some illustrative embodiments, this disclosure relates to a method for treating a patient with a disease caused by abnormal activities of CBX8 of polycomb chromobox protein homolog proteins comprising the step of administering a therapeutically effective amount of one or more compounds as disclosed herein to the patient in need of relief from said disease.

In some illustrative embodiments, this disclosure relates to a method for treating a patient with a disease caused by abnormal activities of CBX8 of polycomb chromobox protein homolog proteins comprising the step of administering a therapeutically effective amount of one or more compounds as disclosed herein to the patient in need of relief from said disease, wherein said disease is a cancer or leukemia.

In some illustrative embodiments, this disclosure relates to a pharmaceutical composition for treating a patient with a disease caused by abnormal activities of CBX8 of polycomb chromobox protein homolog proteins comprising the step of administering a therapeutically effective amount of one or more compounds as disclosed herein to the patient in need of relief from said disease.

In some illustrative embodiments, this disclosure relates to a pharmaceutical composition for treating a patient with a disease caused by abnormal activities of CBX8 of polycomb chromobox protein homolog proteins comprising the step of administering a therapeutically effective amount of one or more compounds as disclosed herein to the patient in need of relief from said disease, wherein said disease is a cancer or leukemia.

BRIEF DESCRIPTION OF THE DRAWINGS

The above and other objects, features, and advantages of the present invention will become more apparent when taken in conjunction with the following description and drawings wherein identical reference numerals have been used, and wherein:

FIG. 2A: A heat map is presented for the enrichment of PSL2A library member to all PcG CBX ChDs and CBX5 ChD. Representative monomer structures are presented. Enrichment was calculated relative to non-ligand from DNA sequencing.

FIG. 2B: A heat map is presented for the enrichment of PSL2B library member to all PcG CBX ChDs and CBX5 ChD. Representative monomer structures are presented. Enrichment was calculated relative to non-ligand from DNA sequencing.

FIG. 3A: PSL2A, P(−2) residue; FIG. 3B: PSL2B, P(−3) cap; FIG. 3C: PSL2B, P(−4) residue.

FIGS. 4A-4C show structural basis of SW2_110A binding. FIG. 4A: Overlay of $^{15}$N-HSQC spectra of CBX8 CD upon addition of increasing concentration of SW2_110A. Molar ratios are color coded as indicated in legend. FIG. 4B: Chemical shift perturbations (CSPs) as a function of CBX8 CD residue. Residues for which resonances disappear upon binding are denoted by a blue sphere, and residues missing resonances entirely are denoted with gray spheres. Perturbations were considered significant if they were greater than the average plus on standard deviation (denoted by the blue line), not including the highest 10% of CSP values or missing peaks. FIG. 4C: Residues with significant CSPs are colored blue on a cartoon representation of CBX8 in complex with H3K9me3 (PDB ID 3191). The H3K9me3 peptide is shown as white sticks, and the aromatic cage residues important for coordinating the methyllysine are shown as gray sticks.

FIG. 8A: The protein expression of all five CBX paralogs (along with BRG1 as a loading control) was assessed using immunoblot analysis. Nuclear lysate (10 µg) was analyzed for five glioblastoma cell lines (A172, T98, U87, U118, U138) along with the non-cancerous astrocyte cell line Svg12. Notably, the glioblastoma cell lines all display an increase in CBX8 and a decrease in CBX6 expression compared to astrocytes.

FIG. 8B: Two shRNA knockdown constructs were tested in glioblastoma cell lines using lentiviral mediated knockdown. The viability was determined using trypan blue and cell counting after 5 days of CBX8 knockdown.

FIG. 8C: shRNA resistant exogenous CBX8, but not a chromodomain mutant CBX8 (K31A, W32A), could rescue the viability defect observed upon CBX8 knockdown. The viability was determined using sulforhodamine assay after 5 days of CBX8 knockdown.

DETAILED DESCRIPTION

Figure 1A:
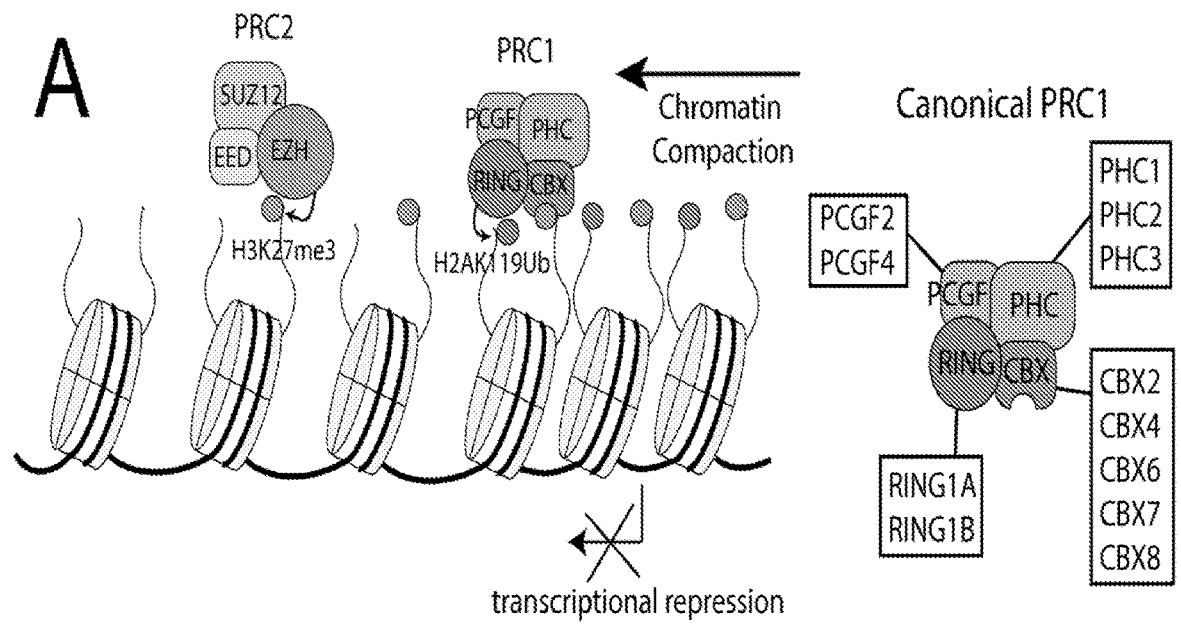
FIG. 1A: Canonical Pc-mediated gene transcriptional repression. Trimethyllysine marks installed by PRC2 on H3K27 are recognized by PRC1, followed up by monoubiquitination at H2AK119, resulting in chromatin compactions and transcriptional repression. Paralogous subunits combine to produce many possible PRC1 complexes with unknown function.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Those skilled in the art will recognize that numerous modifications can be made to the specific implementations described above. The implementations should not be limited to the particular limitations described. Other implementations may be possible.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, or within 99% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, e.g. E, and Z, double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C(CH$_3$)— and the like.

The term "alkylene" as used herein refers to substituted or unsubstituted straight chain and branched divalent alkylene groups and cycloalkylene groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$) or, in some embodiments, from 1 to 4 carbon atoms ($C_1$-$C_4$), from 1 to 5 carbon atoms ($C_1$-$C_5$), from 2 to 5 carbon atoms ($C_2$-$C_5$) or from 3 to 4 carbon atoms ($C_3$-$C_4$). Examples of straight chain alkylene groups include those with from 1 to 8 carbon atoms such as methylene (—CH$_2$—), ethylene (—CH$_2$CH$_2$—), n-propylene (—CH$_2$CH$_2$CH$_2$—), n-butylene (—CH$_2$(CH$_2$)$_2$CH$_2$—) and the like. Examples of branched alkylene groups include, but are not limited to, isopropylidene (CH$_2$CH(CH$_3$)) and the like. Examples of cycloalkylene groups include, but are not limited to, cyclopropylidene, cyclobutylidene, cyclopentylidene and the like.

The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heteroarylalkyl" as used herein refers to alkyl groups as defined herein in which a hydrogen or carbon bond of an alkyl group is replaced with a bond to a heteroaryl group as defined herein.

The term "amine" as used herein refers to primary, secondary, and tertiary amines. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of halo alkyl include trifluoromethyl, 1,1-dichloroethyl, perfluorobutyl, —CF($CH_3$)$_2$ and the like.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, that are synthetic, naturally occurring, and non-naturally occurring, have similar binding properties as the reference nucleic acid, and metabolized in a manner similar to the reference nucleotides.

The terms "polypeptide," "peptide," and "protein" are used interchangeably herein to refer to a polymer of amino acid residues, a polypeptide, or a fragment of a polypeptide, peptide, or fusion polypeptide. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the corresponding naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e. a carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Various embodiments of the present invention also contemplate pharmaceutical compositions comprising one or more compounds of the various embodiments of the present invention and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some embodiments, the present invention contemplates compositions comprising a therapeutically effective amount of one or more compounds of the various embodiments of the present invention. In some embodiments, the compositions are useful in a method for treating cancer, the method comprising administering a therapeutically effective amount of one or more compounds of any claim to a patient in need thereof. In some aspects, the various embodiments of the present invention contemplate a compound of the formula (I) (II) and (III) for use as a medicament for treating a patient in need of relief from cancers, including, but not limited to, prostate cancer, lung cancer, breast cancer, or pancreatic cancer.

In some other embodiments, the present invention contemplates compositions comprising a therapeutically effective amount of a compound of the present invention, together with a therapeutically effective amount of one or more other compounds of the same or different mode of action to a patient in need of relief from said cancer.

The term "therapeutically effective amount" as used herein, refers to that amount of one or more compounds of the various embodiments of the present invention that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, this present invention is related to a compound having a general formula (I):

(I)

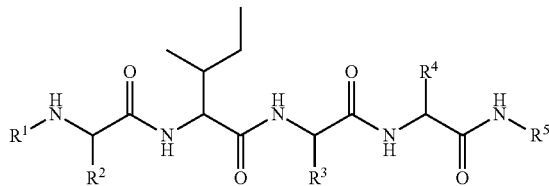

or a pharmaceutically acceptable salt thereof, wherein,
$R^1$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, heteroarylalkyl, or one to two amino acid residues; each of which is optionally substituted;
$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^3$ is an alkylamino, alkenylamino, cycloalkylamino, cycloalkenylamino, heteroalkylamino, or heteroalkenylamino; each of which is optionally substituted;
$R^4$ is heteroalkyl, heteroalkenyl, heterocyclyl; and
$R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted.

In some illustrative embodiments, this present invention is related to a compound having a general formula (II):

(II)

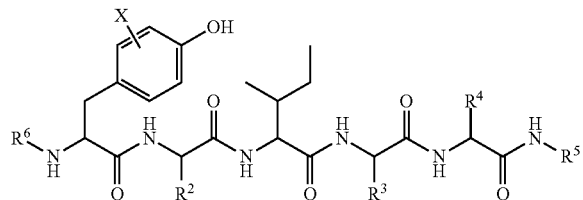

or a pharmaceutically acceptable salt thereof, wherein X represents four substituents, independently, hydrogen or halo;
$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^3$ is an alkylamino, alkenylamino, cycloalkylamino, cycloalkenylamino, heteroalkylamino, or heteroalkenylamino; each of which is optionally substituted;
$R^4$ is heteroalkyl, heteroalkenyl, heterocyclyl;
$R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted; and
$R^6$ is an alkyl, alkenyl, alkynyl, cycloalkyl, cycloalkenyl, heterocyclyl, aryl, heteroaryl, arylalkyl, or heteroarylalkyl, each of which is optionally substituted.

In some illustrative embodiments, this present invention is related to a compound having a general formula (III):

(III)

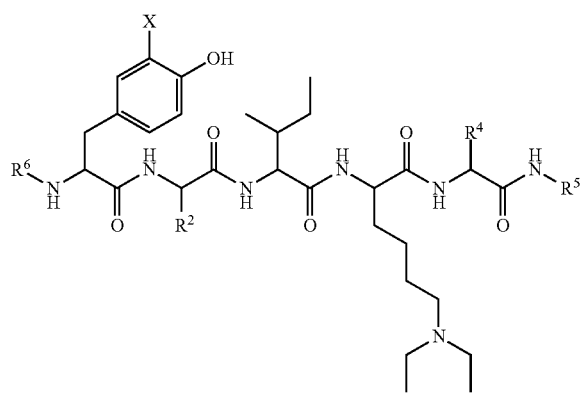

or a pharmaceutically acceptable salt thereof, wherein X represents a halo;
$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;
$R^4$ is heteroalkyl, heteroalkenyl, heterocyclyl;

R[5] is hydrogen, an alkyl, alkenyl, alkynyl, cycloalkyl, cycloalkenyl, heterocyclyl, aryl, heteroaryl, arylalkyl, or heteroarylalkyl, each of which is optionally substituted;
and
R[6] is an alkyl, alkenyl, alkynyl, cycloalkyl, cycloalkenyl, heterocyclyl, aryl, heteroaryl, arylalkyl, or heteroarylalkyl, each of which is optionally substituted.

In some illustrative embodiments, this present invention is related to a compound having a general formula (III), wherein R[4] is hydroxymethyl and X is chloro.

In some illustrative embodiments, this present invention is related to a compound having a general formula (III), wherein the compound is

SEQ ID NO: 1

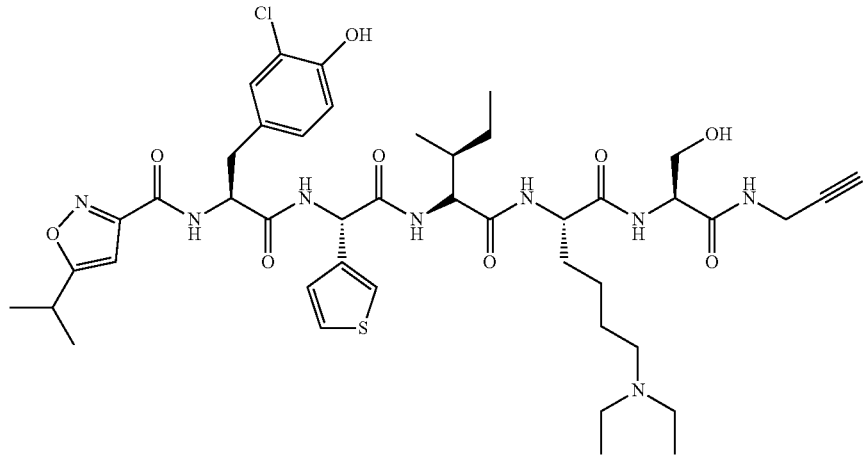

SW2_104A

SEQ ID NO: 2

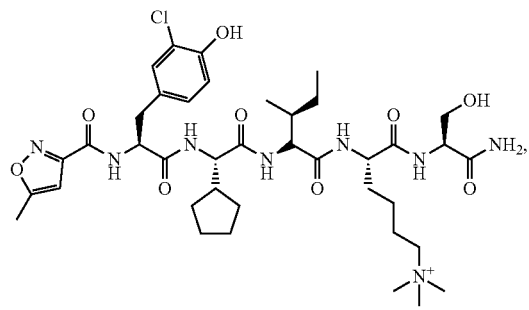

KED98

SEQ ID NO: 3

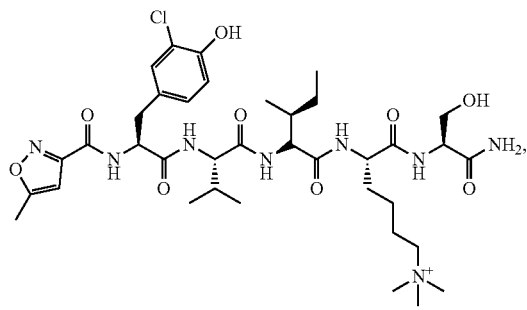

KED97

SEQ ID NO: 4

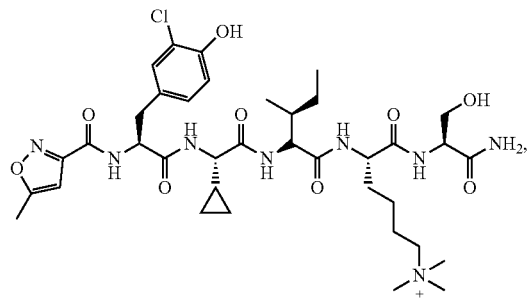

SW2_90

SEQ ID NO: 5

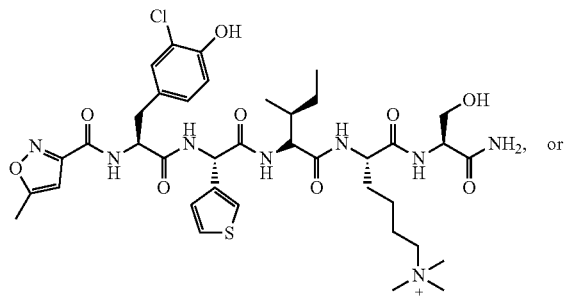

SW2_101E or

SEQ ID NO: 6

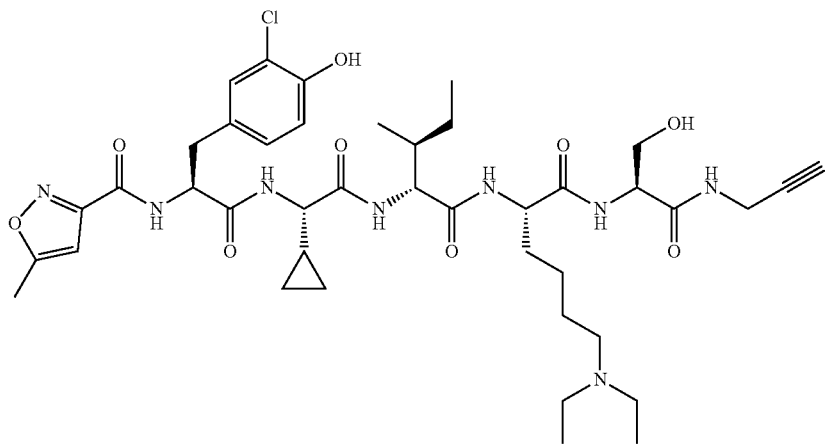

SW2_90L

In some illustrative embodiments, this present invention is related to a compound having a general formula (IV):

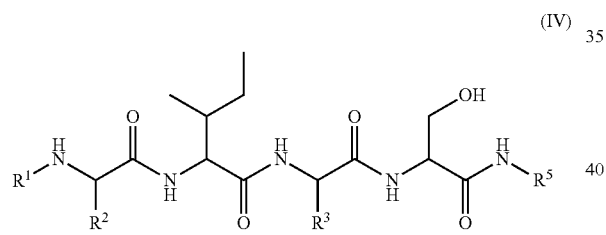

(IV)

or a pharmaceutically acceptable salt thereof, wherein $R^1$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;

$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;

$R^3$ is an alkylamino, alkenylamino, cycloalkylamino, cycloalkenylamino, heteroalkylamino, or heteroalkenylamino; each of which is optionally substituted; and $R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted.

In some illustrative embodiments, this present invention is related to a compound having a general formula (IV), wherein the compound is

SEQ ID NO: 7

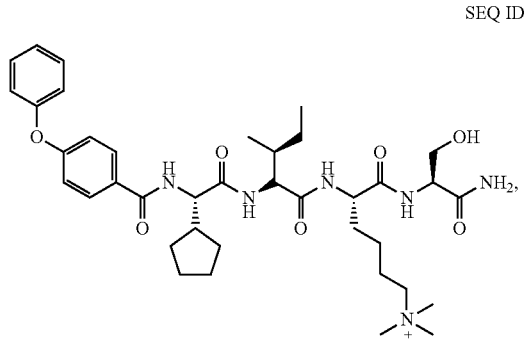

SW2_101B

SEQ ID NO: 8

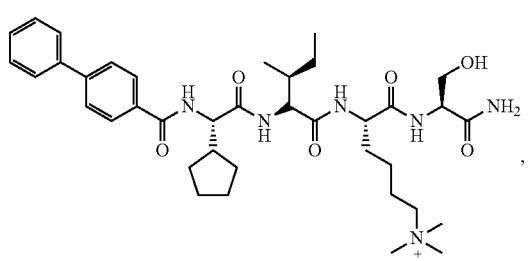

SW2_89

SEQ ID NO: 9
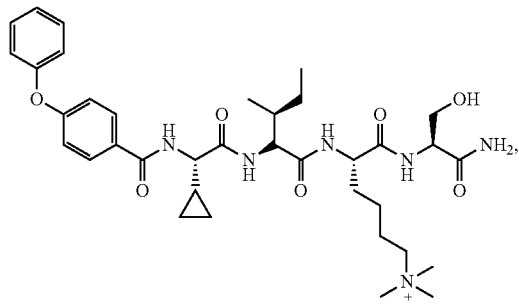
SW2_101F
SEQ ID NO: 10
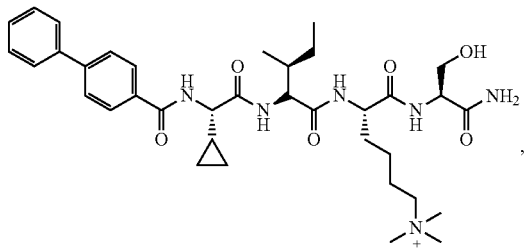
SW2_101A
SEQ ID NO: 11
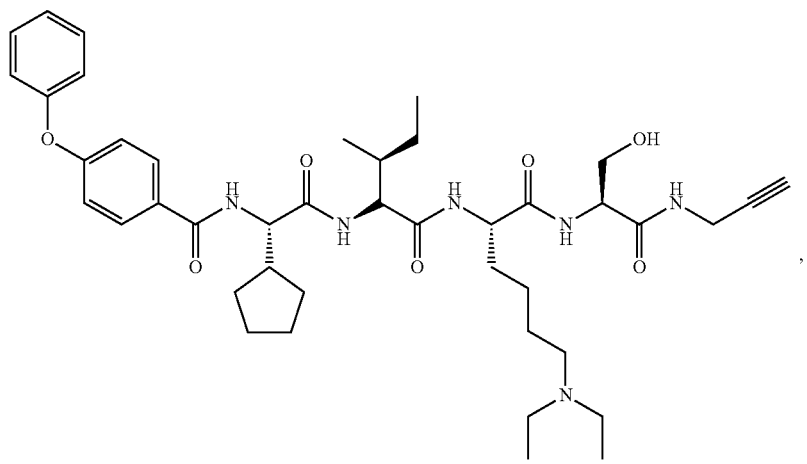
SW2_110A
SEQ ID NO: 12
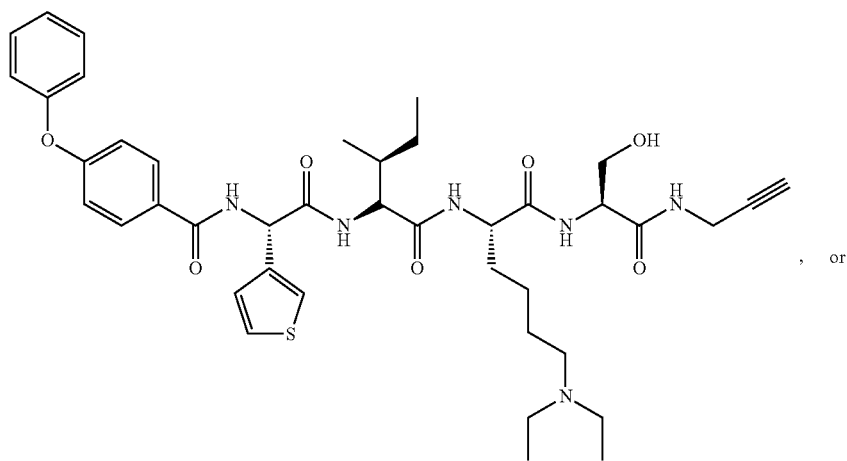
, or
SW2_110B

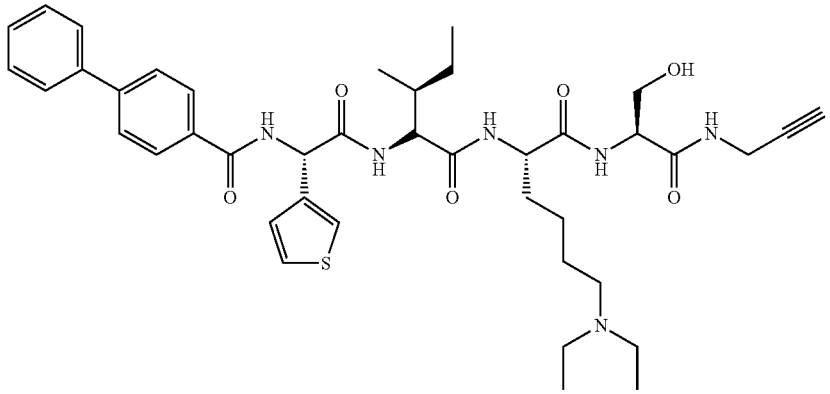

SW2_104B (SEQ ID NO: 13)

In some illustrative embodiments, this present invention is related to a compound having a general formula (IV), wherein said compound is:

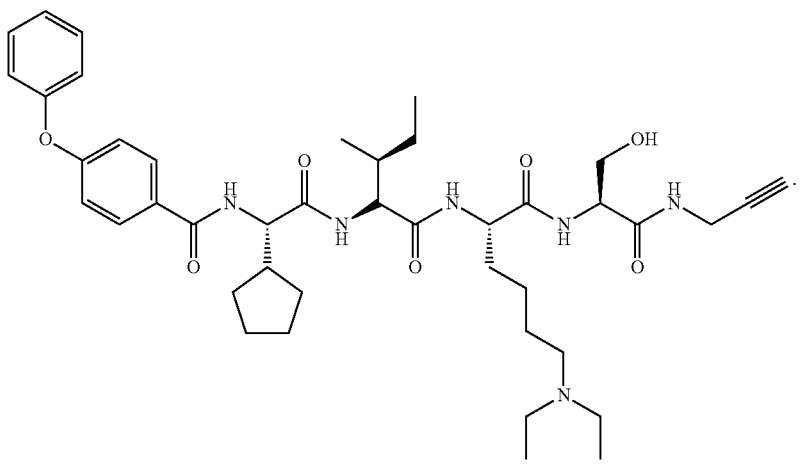

(SEQ. ID NO: 11)

In some illustrative embodiments, this present invention is related to a pharmaceutical composition comprising one or more compounds as disclosed herein, together with one or more pharmaceutically acceptable diluents, excipients, or carriers.

In some illustrative embodiments, this present invention is related to a method for treating a patient with a disease caused by abnormal activities of CBX8 of polycomb chromobox protein homolog proteins comprising the step of administering a therapeutically effective amount of a compound as disclosed herein, to the patient in need of relief from said disease.

In some illustrative embodiments, this present invention is related to a method for treating a patient with a cancer or leukemia caused by abnormal activities of CBX8 of polycomb chromobox protein homolog proteins comprising the step of administering a therapeutically effective amount of a compound as disclosed herein, to the patient in need of relief from said disease.

In some illustrative embodiments, this present invention is related to a method for treating a patient with a disease caused by abnormal activities of CBX8 of polycomb chromobox protein homolog proteins comprising the step of administering a therapeutically effective amount of a compound as disclosed herein, together with a therapeutically effective amount of one or more other compounds of the same or different mode of action, to the patient in need of relief from said disease.

In some illustrative embodiments, this present invention is related to a method for treating a patient with a disease caused by abnormal activities of CBX8 of polycomb chromobox protein homolog proteins comprising the step of administering a therapeutically effective amount of one or more compounds to the patient in need of relief from said disease, wherein said compound has a formula (I)

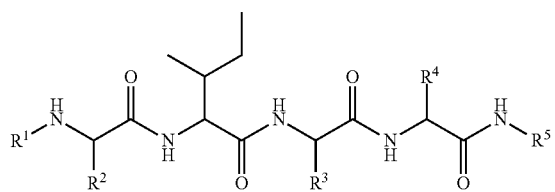

or a pharmaceutically acceptable salt thereof, wherein,

R¹ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, heteroarylalkyl, or one to two amino acid residues; each of which is optionally substituted;

R² is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;

R³ is an alkylamino, alkenylamino, cycloalkylamino, cycloalkenylamino, heteroalkylamino, or heteroalkenylamino; each of which is optionally substituted;

R⁴ is heteroalkyl, heteroalkenyl, heterocyclyl; and

R⁵ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted.

In some illustrative embodiments, this present invention is related to a method for treating a patient with a disease caused by abnormal activities of CBX8 of polycomb chromobox protein homolog proteins comprising the step of administering a therapeutically effective amount of one or more compounds as disclosed herein, to the patient in need of relief from said disease, wherein said compound is

SEQ ID NO: 1

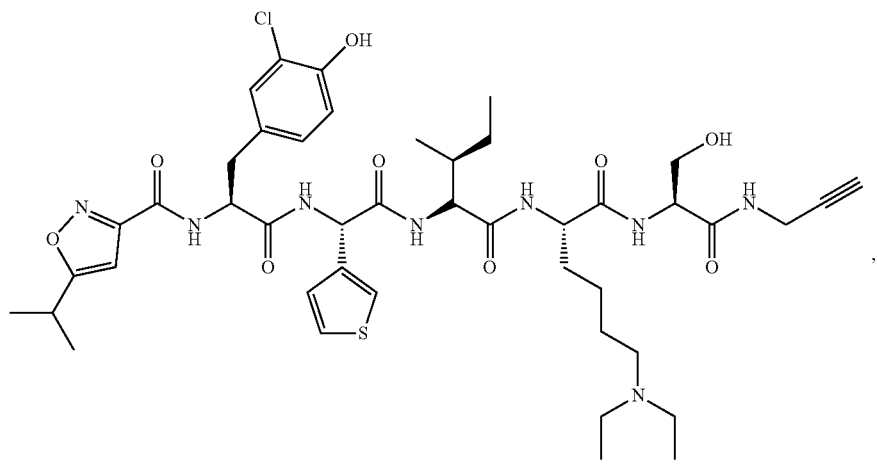

SW2_104A

SEQ ID NO: 2

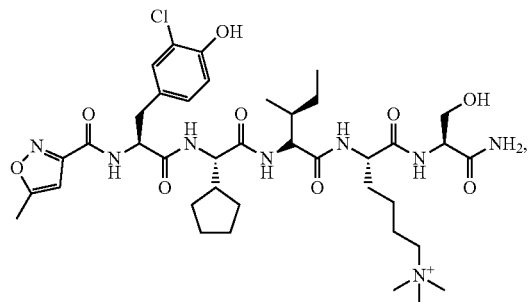

KED98

SEQ ID NO: 3

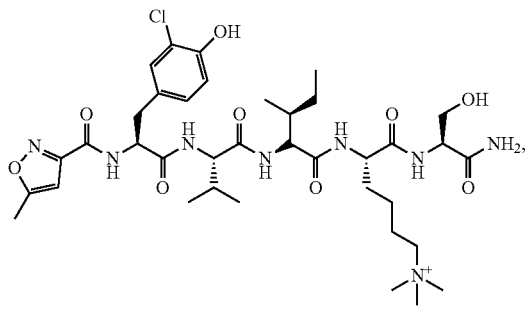

KED97

SEQ ID NO: 4
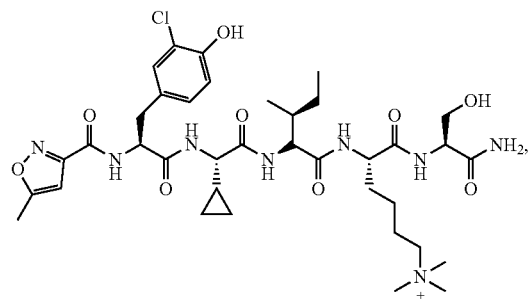
SW2_90
SEQ ID NO: 5
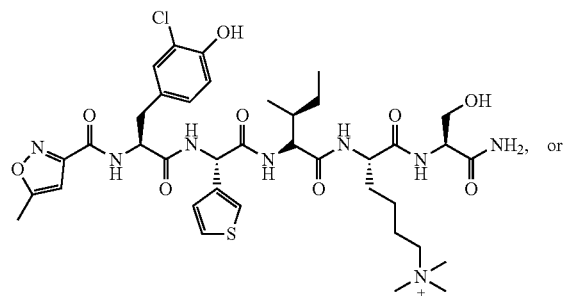
SW2_101E, or
SEQ ID NO: 6
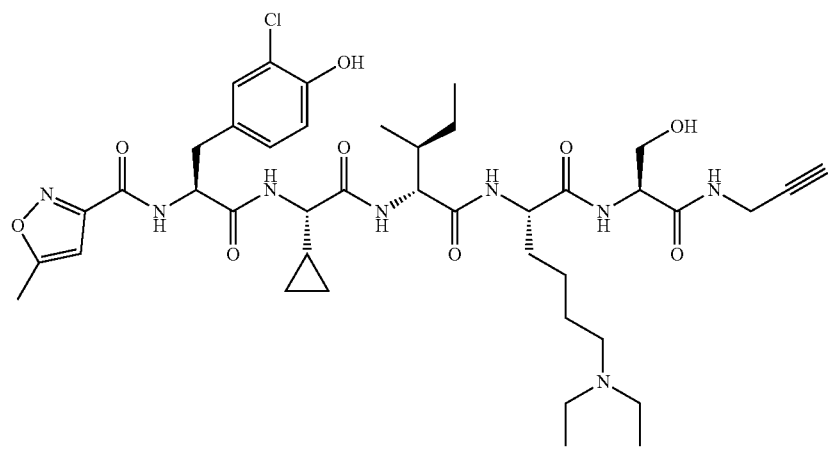
SW2_90L
SEQ ID NO: 7
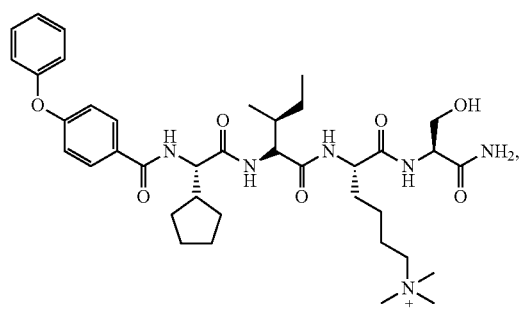
SW2_101B
SEQ ID NO: 8
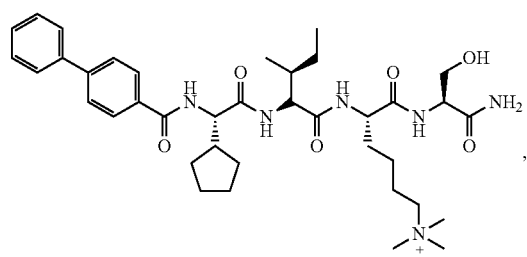
SW2_89
SEQ ID NO: 9
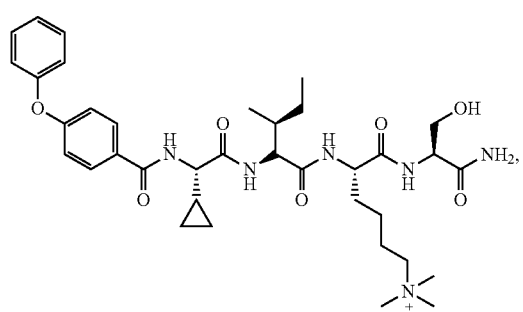
SW2_101F
SEQ ID NO: 10
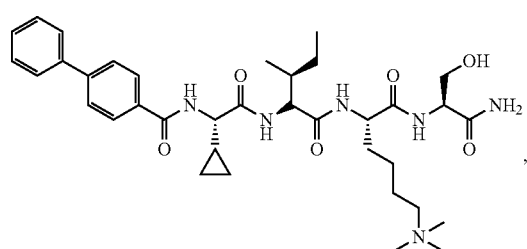
SW2_101A SEQ ID NO: 11
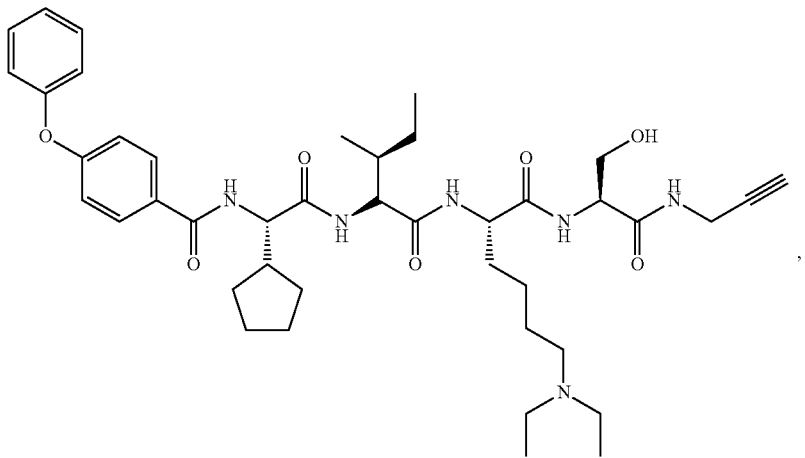
SW2_110A
SEQ ID NO: 12
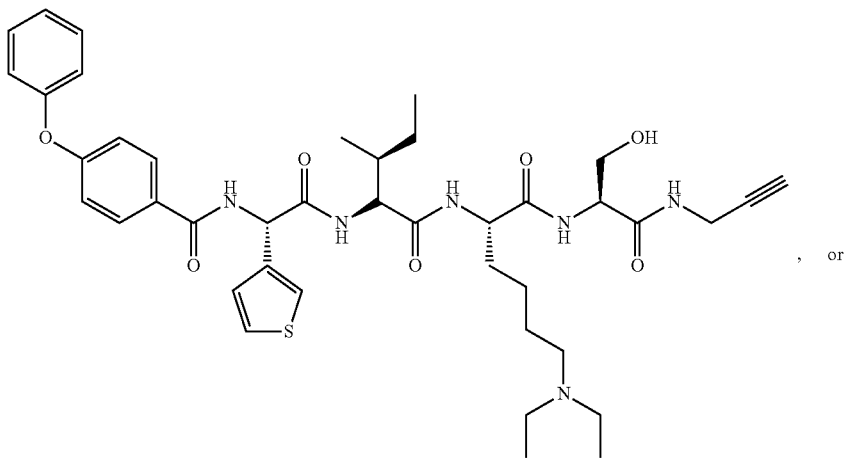
SW2_110B , or
(SEQ ID NO: 13)
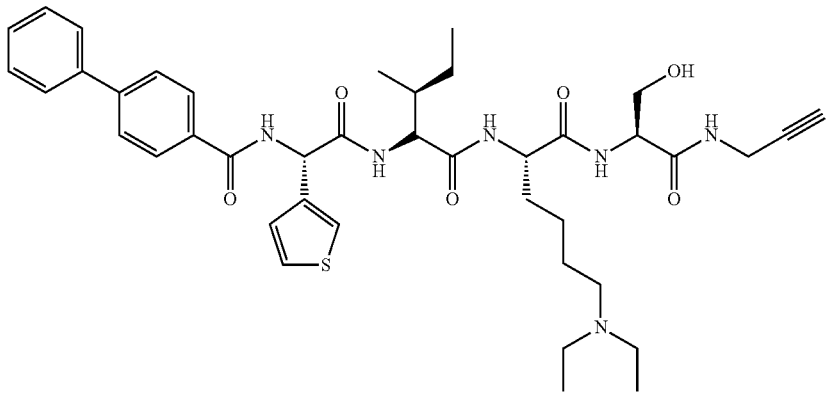
SW2_104B
In some illustrative embodiments, this present invention is related to a method for treating a patient of cancer or leukemia, wherein said patient has an abnormal activities of CBX8, comprising the step of administering a therapeutically effective amount one or more compounds having the formula (I):

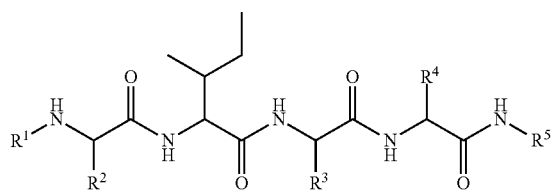

(I)

or a pharmaceutically acceptable salt thereof, wherein, $R^1$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, heteroarylalkyl, or one to two amino acid residues; each of which is optionally substituted;

$R^2$ is an alkyl, alkenyl, alkynyl, acyl, arylalkylacyl, arylacyl, cycloalkyl, cycloalkenyl, heterocyclyl, aryl, heteroalkyl, heteroalkenyl, heteroalkynyl, heteroaryl, arylalkyl, arylalkenyl, arylalkynyl, or heteroarylalkyl; each of which is optionally substituted;

$R^3$ is an alkylamino, alkenylamino, cycloalkylamino, cycloalkenylamino, heteroalkylamino, or heteroalkenylamino; each of which is optionally substituted;

$R^4$ is heteroalkyl, heteroalkenyl, heterocyclyl; and $R^5$ is hydrogen, an alkyl, alkenyl, alkynyl, cycloalkyl, cycloalkenyl, heterocyclyl, aryl, heteroaryl, arylalkyl, or heteroarylalkyl, each of which is optionally substituted.

In some illustrative embodiments, this present invention is related to a method for treating a patient of cancer or leukemia, wherein said patient has an abnormal activities of CBX8, comprising the step of administering a therapeutically effective amount one or more compounds, or a pharmaceutically acceptable salt thereof, wherein said compound is:

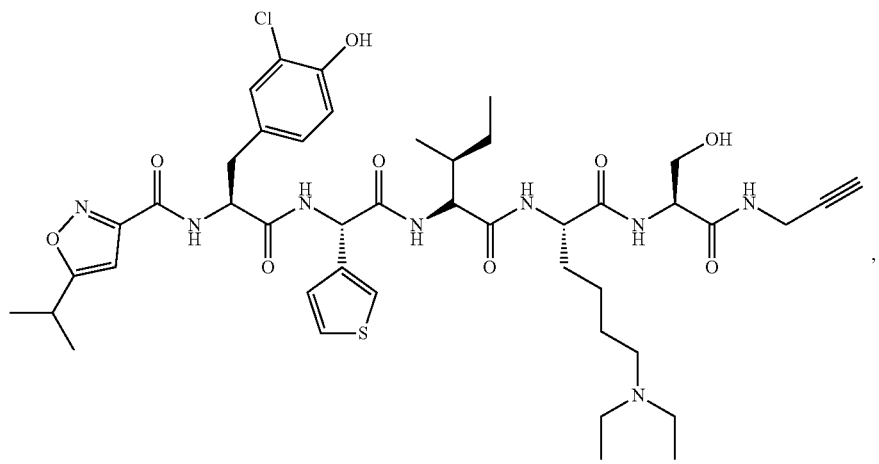

SEQ ID NO: 1

SW2_104A

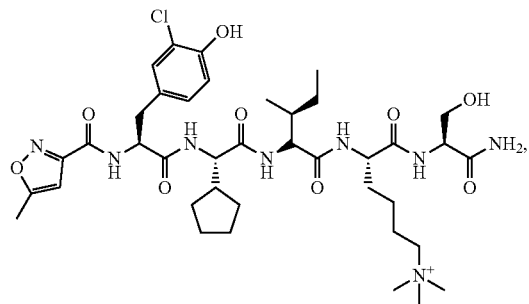

SEQ ID NO: 2

KED98

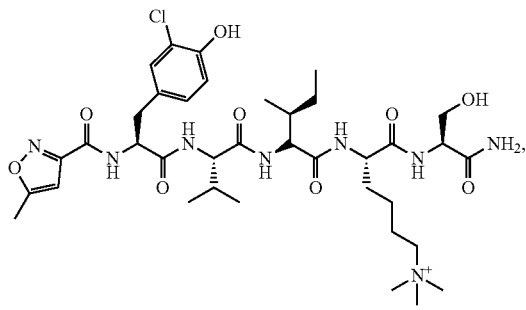

SEQ ID NO: 3

KED97

SEQ ID NO: 4
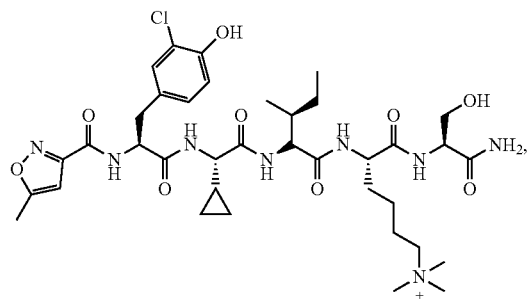
SW2_90
SEQ ID NO: 5
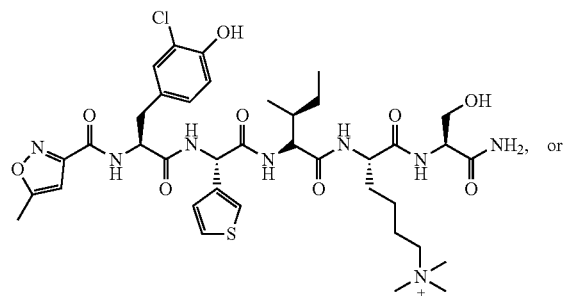
SW2_101E
or
SEQ ID NO: 6
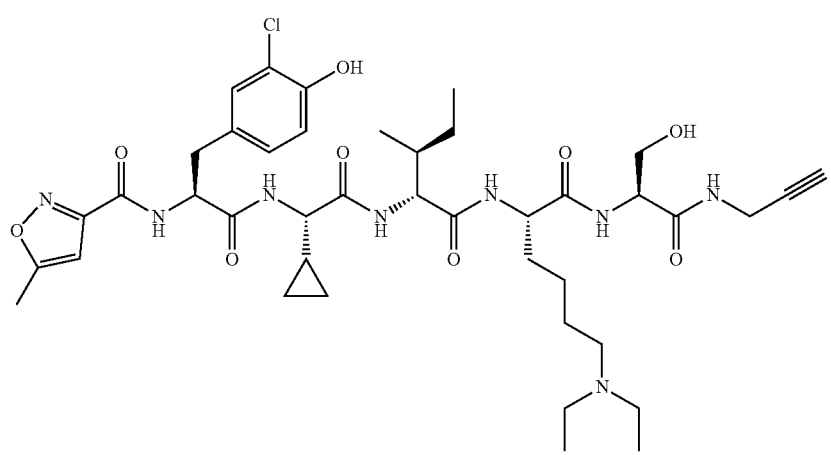
SW2_90L
SEQ ID NO: 7
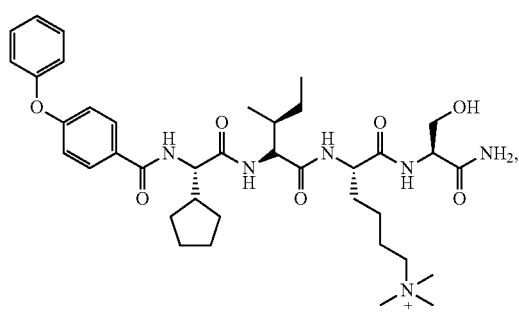
SW2_101B
SEQ ID NO: 8
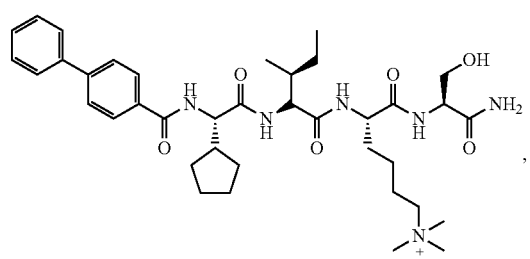
SW2_89
SEQ ID NO: 9
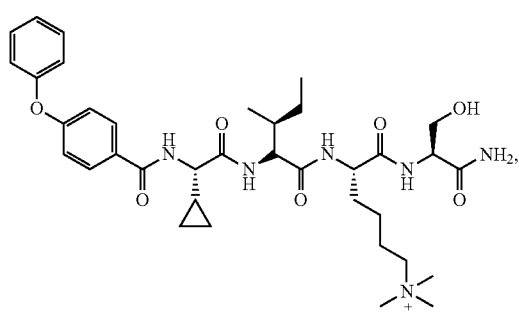
SW2_101F
SEQ ID NO: 10
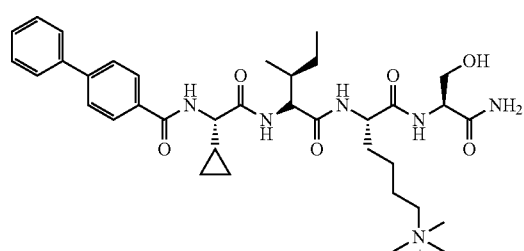
SW2_101A

SEQ ID NO: 11

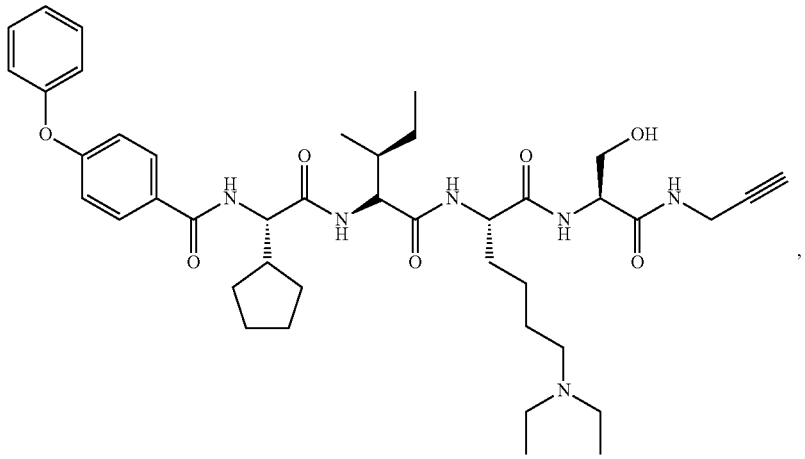
SW2_110A

SEQ ID NO: 12

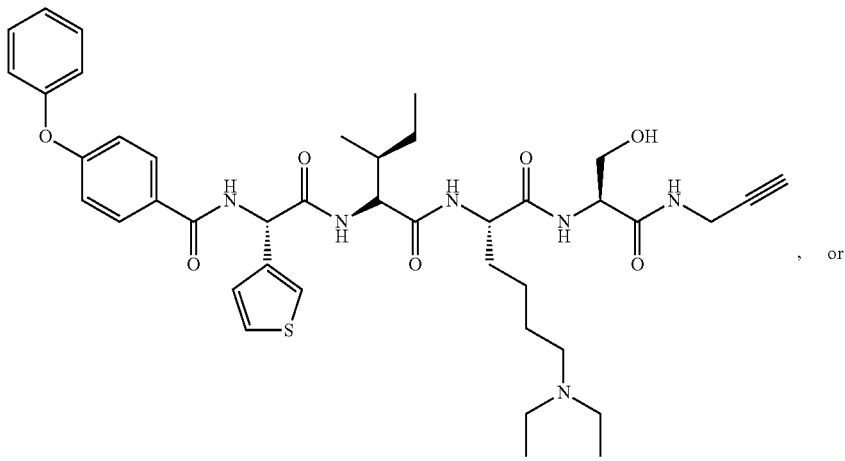
SW2_110B , or (SEQ ID NO: 13)

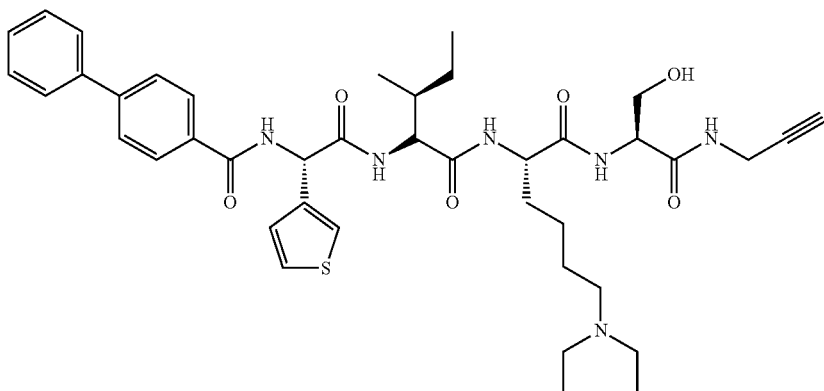
SW2_104B

In some illustrative embodiments, this present invention is related to a method for treating a patient with a mixed lineage leukemia (MLL) caused by abnormal activities of CBX8 of polycomb chromobox protein homolog proteins comprising the step of administering a therapeutically effective amount of a compound as disclosed herein, to the patient in need of relief from said disease.

In some illustrative embodiments, this present invention is related to a method for treating a patient with glioblastoma caused by abnormal activities of CBX8 of polycomb chromobox protein homolog proteins comprising the step of administering a therapeutically effective amount of a compound as disclosed herein, to the patient in need of relief from said disease.

Polycomb repressive complex 1 (PRC1) is critical for mediating gene expression during development. Five Polycomb Chromobox protein homolog (CBX) proteins, CBX2, 4,6,7,8, form mutually exclusive PRC1 complexes and mediate specific targeting to trimethylated lysine 27 of histone H3 (H3K27me3) via the N-terminal chromodomain (ChD). Individual CBX paralogs have been implicated as drug targets for cancer; however, high homologies in sequence and structure among the CBX chromodomains (ChD) provide a major obstacle in developing selective CBX ChD inhibitors. Here we report the use of DNA-encoded chemical libraries for the development of SW2_110A, a selective, cell-permeable inhibitor of the CBX8 chromodomain (ChD). SW2_110A binds CBX8 ChD with a KI of ~800 nM, with minimally 5-fold selectivity for CBX8 over all other CBX paralogs in vitro. SW2_110A specifically inhibits the association of CBX8 with chromatin in cells and inhibits proliferation of THP1 leukemia cells driven by MLL-AF9 translocation. In THP1 cells, SW2_110A treatment results in the significant decrease in the expression of the MLL-AF9 target gene HOXA9, validating a role for the CBX8 chromodomain in MLL-AF9 transcriptional regulation. SW2_110A will be a useful tool for further investigation of CBX8's role in MLL-AF9 mediated transcription, CBX8's role in other cancer types, and the mechanism by which CBX8 regulates chromatin structure and transcription. The success of SW2_110A provides great promise for the development of highly selective and cell permeable probes for the full CBX family.

We have employed DNA-encoded chemical libraries, which have numerous advantages over conventional ligand discovery and development approaches (Goodnow, Dumelin, and Keefe, 2017; Franzini, Neri, and Scheuermann, 2014). In a previous study, we used CBX7 ligands with over 10-fold weaker affinity for CBX8 (Stuckey, Simpson, et al., 2016) to develop quantitative metrics for affinity selection assays of DNA-encoded libraries against CBX chromodomains. With a library of DNA-encoded peptidomimetics, we demonstrated that selection assays are capable of faithfully replicating known SAR of CBX7 and CBX8 ligands and identified 5 monomers that increased affinity and selectivity to CBX8 (Denton et al., 2018), In this manuscript, we utilized DNA-encoding and affinity selection further with on-DNA medicinal chemistry optimization of CBX8 chromodomain inhibitors with high affinity (400-800 nM), selectivity (>5-20-fold compared to other paralogs), and cell permeability. We used these ligands as chemical probes to define the CBX8 ChD as a therapeutic target in MLL-AF9 leukemia using cell line THP1.

In Vitro Selection Assays of Peptidomimetic Ligands to CBX Chromodomains Via DNA-Encoded Positional Scanning Library (PSL)

First-Generation DNA-Encoded Positional Scanning Library (PSL1)

Figure 1B:
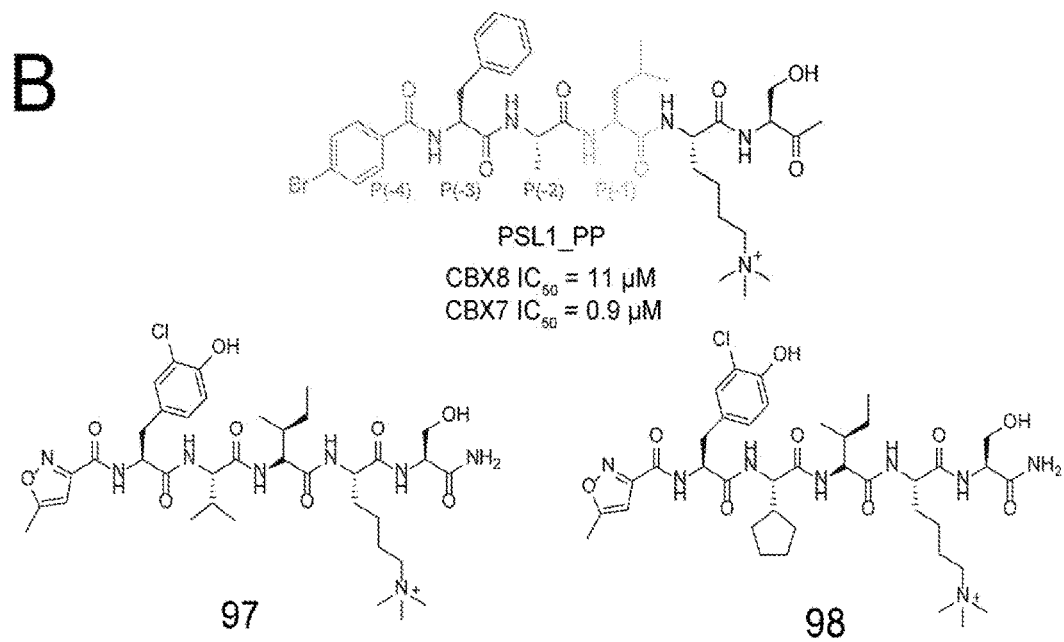
FIG. 1B: Parental Peptide for PSL1 (PSL1_PP) and final PSL1 ligands (97 and 98) with combined synthons. $IC_{50}$ values for 97 and 98 to all PcG CBX ChDs and CBX1 ChD are measured with the FP assay and recapitulates selectivity measurements from the primary screen. NB: no binding.
Figure 1C:
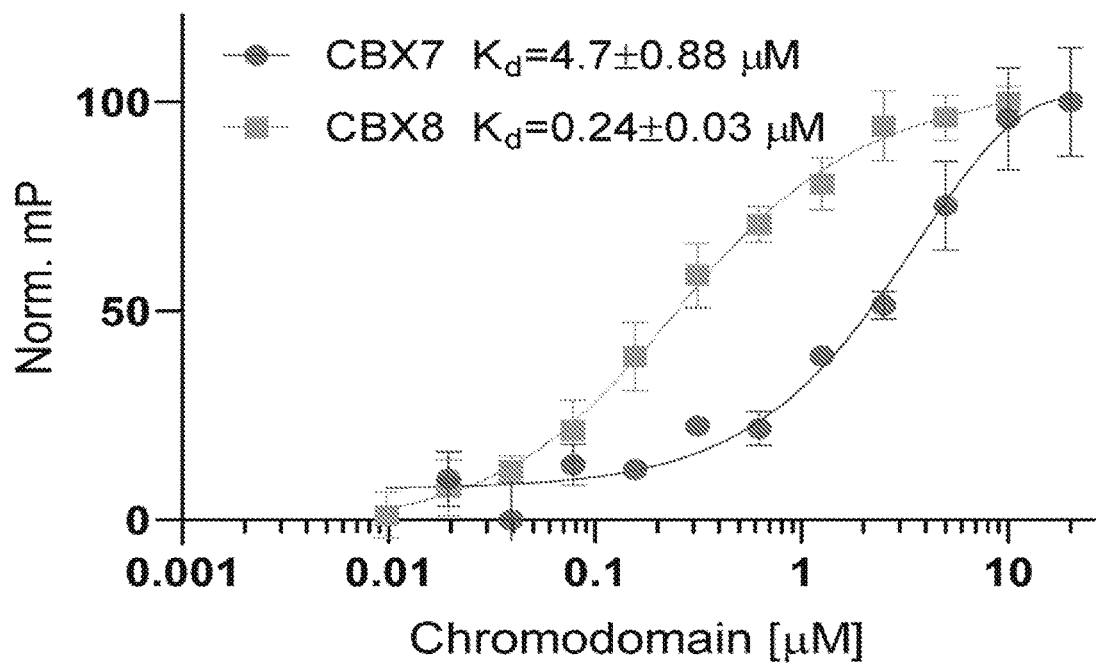
FIG. 1C: Derivatization of 97L (the diethyl-Lys variant of 97) with fluorescein allows for rapid determination of $K_d$ values.
Figure 1D:
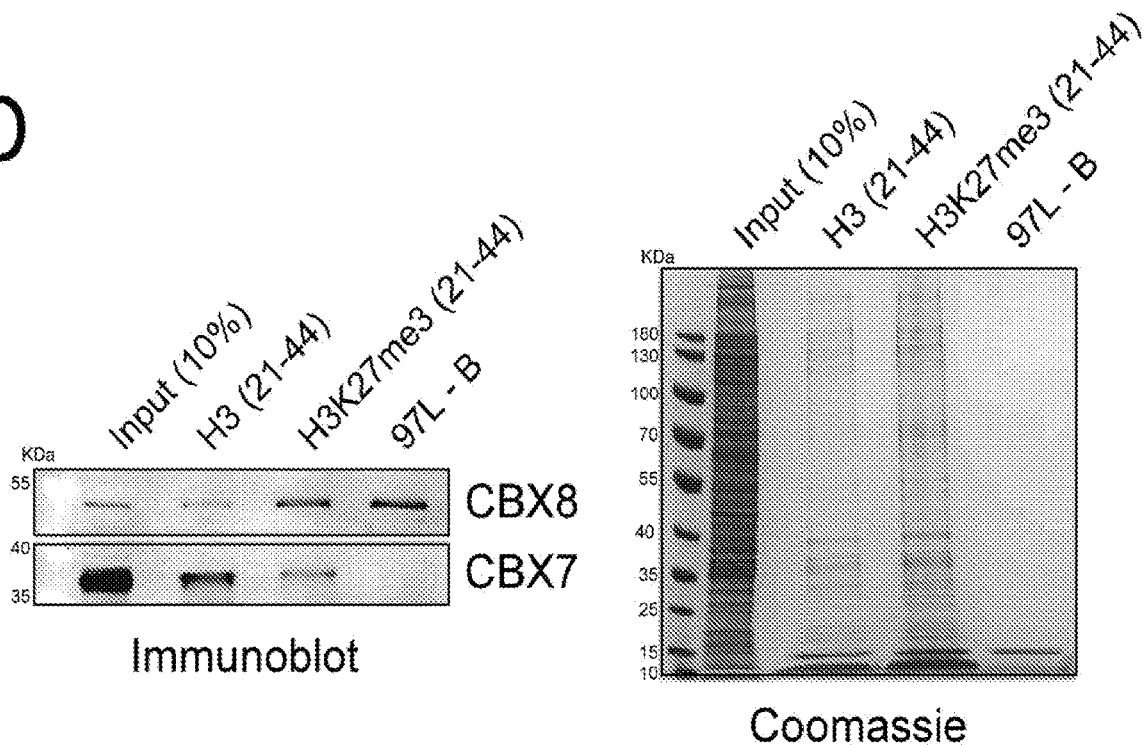
FIG. 1D: Peptide pull-downs from HEK293T lysates using biotin-labeled histone peptides and biotin-labeled CBX8 ChD ligand (97L-B). In immunoblot analysis, 97L-B selectively pulls down endogenous CBX8 from the lysate, but not CBX7. Right is a commassie stain of all enriched proteins.

In the DNA-encoded positional scanning library (PSL1) reported in Denton et al., we identified five monomers within a peptidic ligand that increased ligand selectivity for CBX8 over CBX7. We synthesized two ligands composed of combinations of monomers off-DNA and determined the $IC_{50}$ values for CBX7 and CBX8 in a fluorescence polarization displacement assay (Milosevich et al., 2016). Both peptides were highly selective for CBX8 over CBX7 (FIG. 1B). We further defined the affinity of the more potent ligand, KED97, to CBX7 and CBX8 ChDs by direct fluorescence titration of fluorophore conjugate KED97L-FL (FIG. 1C). For KED97L, the trimethyllysine in KED97 was replaced with diethyllysine, which has shown to increase cell permeability and have little impact on the binding affinity of ligands to polycomb CBX ChDs (Stuckey, Dickson, et al., 2016). Resulting molecule KED97L demonstrated high affinity to the CBX8 ChD ($K_d$=240 nM) and high selectivity (20-fold) over the CBX7 ChD (FIG. 1C). This selectivity was maintained in the context of the full PRC1 complex, as chemoprecipitations from cellular lysates enriched CBX8 but not CBX7 (FIG. 1D). To test cellular activity, we tested KED97L in published CBX8-dependent assays of cell viability (Tan et al., 2011), transcription (Li et al., 2013), and chromatin binding (Pemberton et al., 2014). The growth of the THP1 cell line has previously shown to be dependent on CBX8 by RNAi (Tan et al., 2011), which we confirmed with CRISPR-mediated CBX8 knockout (data not shown). THP1 cell viability was only slightly affected, however, with KED97L treatment at 50 µM. Similarly, gene expression changes of a CBX8 regulated gene in HEK293T cells was only slightly affected, even at high compound concentrations. Levels of CBX8 binding at a known target in Hs68 fibroblast cells, as assessed by ChIP-qPCR, was completely unaffected, even after treatment with 120 µM KED97L. This lack of activity was hypothesized to be due to poor cell permeability, which was confirmed using the chloroalkane penetration assay (CAPA) (Peraro et al., 2017) with a chloroalkane-modified ligand (KED97L-CA). We determined that indeed the permeability was poor ($CP_{50}$>100 µM compared to an $CP_{50}$ of 0.1 µM for the linker alone), which severely limits the utility of this compound.

Before designing a second-generation library, we performed selections of PSL1 against all five chromodomains of the Pc CBX paralogs, along with the chromodomain of CBX5, an HP1 protein, in order to identify additional selectivity determinants. Affinity selections of this library were conducted at three effective protein concentrations, similar to the previous report (Denton et al., 2018). As observed previously, position −2 was the most critical selectivity determinant for binding to CBX paralogs due to differences in the size of a hydrophobic binding pocket. (Simhadri et al., 2014; Stuckey et al., 2016; Milosevich et al., 2016). This pocket in CBX2 and CBX8 is lined by a valine, leucine and alanine, while in CBX4 and CBX7, it is defined by two valines and a leucine, making it considerably smaller (Stuckey et al., 2016). The PSL1 selection results found large decreases in binding for CBX7 and CBX4 as the size of the P(−2) side chain increased beyond a methyl group (Ala, parental compound), while CBX2, CBX6 and CBX8 generally tolerated larger side chains. Interestingly, CBX8 and CBX2 showed an even greater tolerance for large side chains at P(−2) than did CBX6, even though they share the same residues lining this binding pocket. Using a fluorescence polarization displacement assay, we confirmed that KED98 showed similar selectivity as KED97, with slightly improved selectivity for CBX8 over CBX6 (FIG. 1B), the closest PcG CBX paralog by sequence homology. Therefore, cyclopentylglycine was selected as the P(−2) monomer in the parental molecule for PSL2.

Second-Generation DNA-Encoded Positional Scanning Library (PSL2)

To identify probes of CBX8 with improved affinity, selectivity, and cellular permeability, we designed and synthesized a second-generation positional scanning library (PSL2) utilizing KED98 as the parental molecule. For PSL2, we again varied the four positions to the N-terminal side of the trimethyllysine in a parent using building blocks chosen to expand upon the structure-activity relationships (SAR) observed with PSL1 (Denton et al., 2018).

Figure 2A:
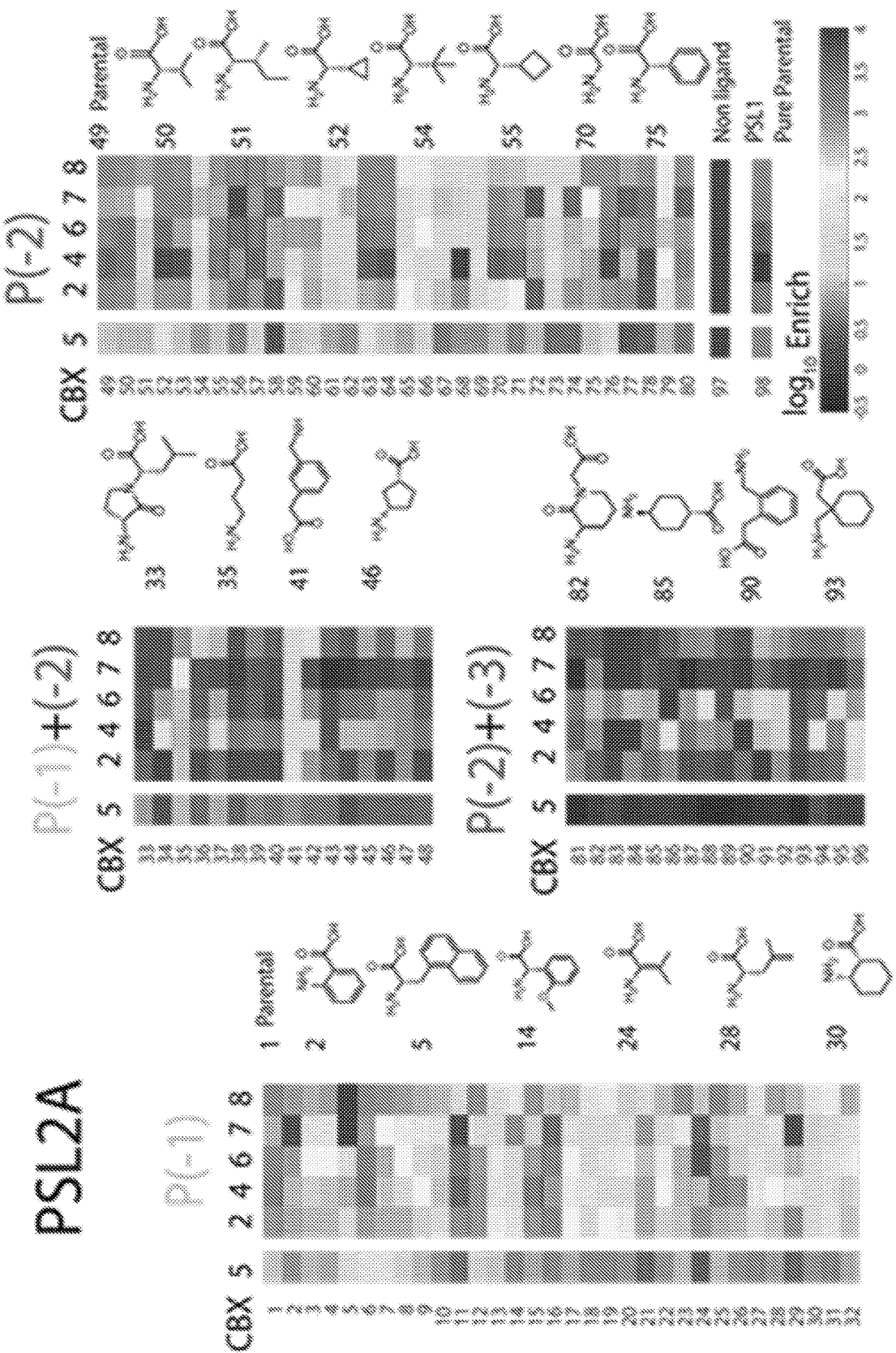
FIGS. 2A-2B: Affinity profiling of 192 peptidic compounds against 6 CBX ChD isoforms by DNA sequencing. 188 unique monomers were tested at each position along with 4 replicates of a parental molecule for the total 192 members in PSL2 library.
Figure 2B:
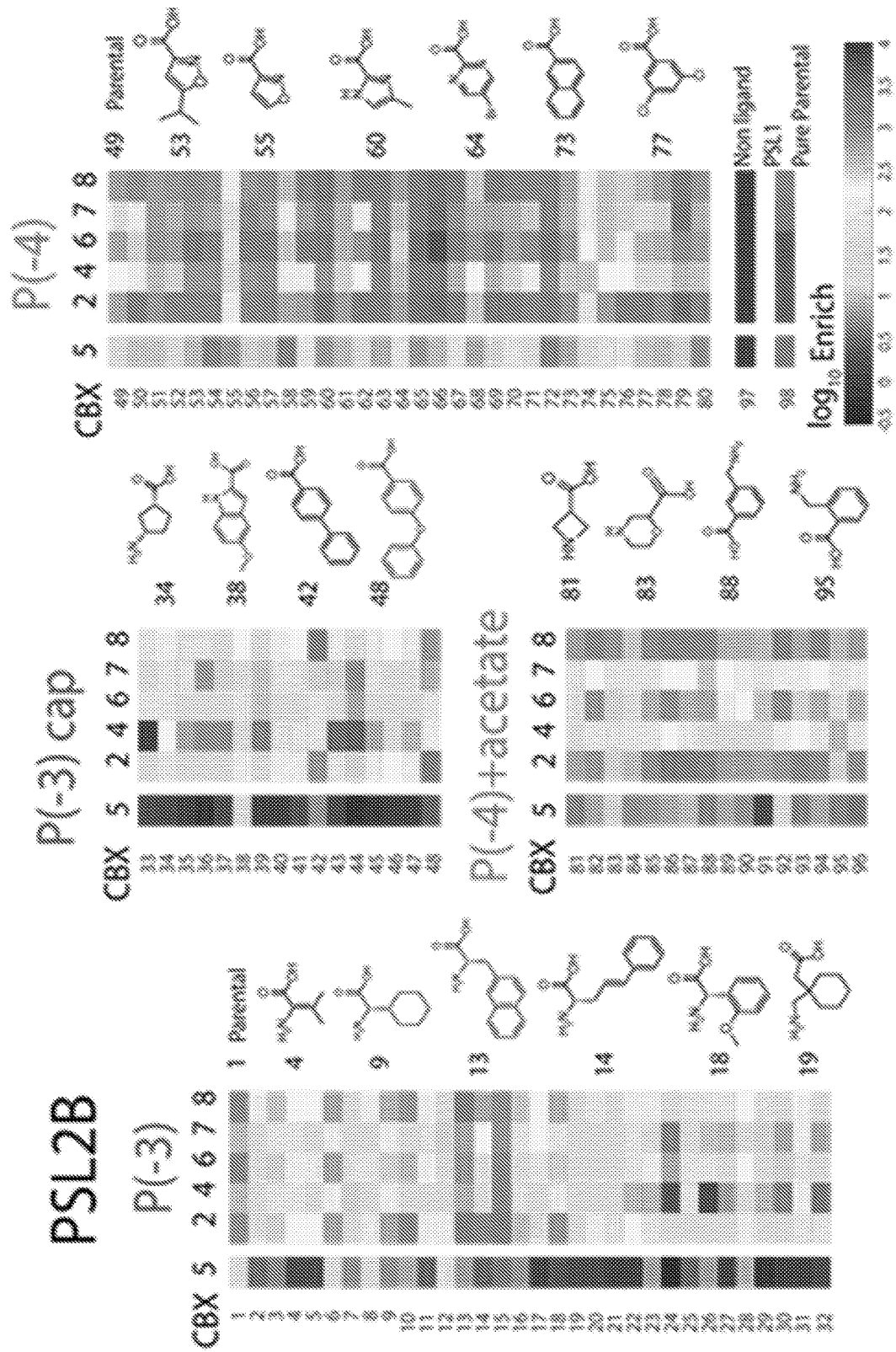

In an effort to reduce the number of amide bonds and molecular weight, we also included a number of larger monomers that might substitute for two sequential monomers (alpha amino acids or the acyl cap) from the parental molecule (either −1+−2, −2+−3, or −3+−4) (FIGS. 2A-2B). Using 96 unique 140-mer dsDNA constructs, we prepared the 192-membered PSL2 in two sets: PSL2A and PSL2B. PSL2A incorporated 32 synthons for positions −1 and −2 and 16 monomer synthons for combined −1+−2 as well as combined −2+−3 positions. Likewise, PSL2B included 32 synthons for positions −3 and −4, as well as 16 synthons for combined −3+−4 positions and 16 amino acid synthons for position −4 with an acetate cap.

For position −1 (PSL2A_1-32), lipophilic amino acids with side chains of different chemical geometry were enriched for all paralogs, with the exception of non-α-amino acids (compound PSL2A_2, PSL2A_16, PSL2A_21, PSL2A_27, PSL2A_29, PSL2A_30) and phenylglycine derivatives (compound PSL2A_14). In general, there was little indication that modification of the P(−1) residue could increase selectivity of the parental ligand for CBX8, or any paralog, with the notable exception of compound PSL2A_5, where a naphthyl Phe derivative decreased binding to all paralogs except CBX4. For position −2 (PSL2A_49-80), synthons with small hydrophobic groups were well tolerated by all Pc CBXs, while non-α-amino acids were not tolerated by any CBX paralogs (Compound PSL2A_56, 72,74,77,78). The tolerance of larger side chains at P(−2) by CBX2, 6, and 8 was reiterated, and synthons as large as isoleucine (PSL2A_51) and phenylglycine (PSL2A_75) indicated binding. For position −3, Phe derivatives (PSL2B_10, PSL2B_13, PSL2B_14, PSL2B_15) are all favored for binding, as with the parental synthon $C_1$-Tyrosine. For position −4, numerous isoxazole derivatives, as well as additional heterocyclic structures were included. The majority of these synthons were favored or well tolerated by the polycomb CBX paralogs.

Monomers included to substitute for both P(−1) and P(−2) positions (compounds PSL2A_33-48) were not tolerated, with the exception of gamma-amino butyric acid (PSL2A_35), which could not be confirmed in off-DNA follow up studies. Similarly, monomers intended to substitute for both P(−2) and P(−3) residues (PSL2A_81-96) were not tolerated. Gratifyingly, two monomers among those included to substitute for both P(−3) and P(−4) monomers (PSL2B_33-48) were tolerated without a large loss in CBX8 binding. Specifically, ligands with a biphenylcarboxylic acid (PSL2B_42) and phenoxybenzoic acid (PSL2B_48) acyl caps at the −3/−4 position demonstrated affinity and selectivity towards CBX8. We synthesized these hits off-DNA via solid phase synthesis for the determination of $IC_{50}$ using a competition fluorescence polarization (FP) assay (Milosevich et al., 2016) (Table 1, column A). Both bind tightly to CBX8 and are completely selective over CBX6, as was indicated in the DNA sequencing data.

Several trends in the PSL2 data sets suggested that selection conditions were not sufficiently stringent to yield differential enrichment among high affinity ligands. In particular, we observed greater affinity of P(−2) cyclopropyl glycine over P(−2) cyclopentyl glycine containing peptides for CBX8 in off-DNA ligands, yet enrichments observed for PSL2A_52 and PSL2A_49 were quite similar. This was also observed with CBX7, which showed a more striking reduction in affinity of the off-DNA ligands (Table 1). Additionally, the majority of the acyl cap monomers displayed similarly high levels of enrichment for the all Pc CBX ChDs despite their varied structures. Therefore, we performed selections against CBX8 a second time using more stringent conditions with lower on-resin protein concentrations to differentiate the top binders in PSL2.

Optimized High Stringency (HS) Selections Against CBX8 ChD

Figure 3A:
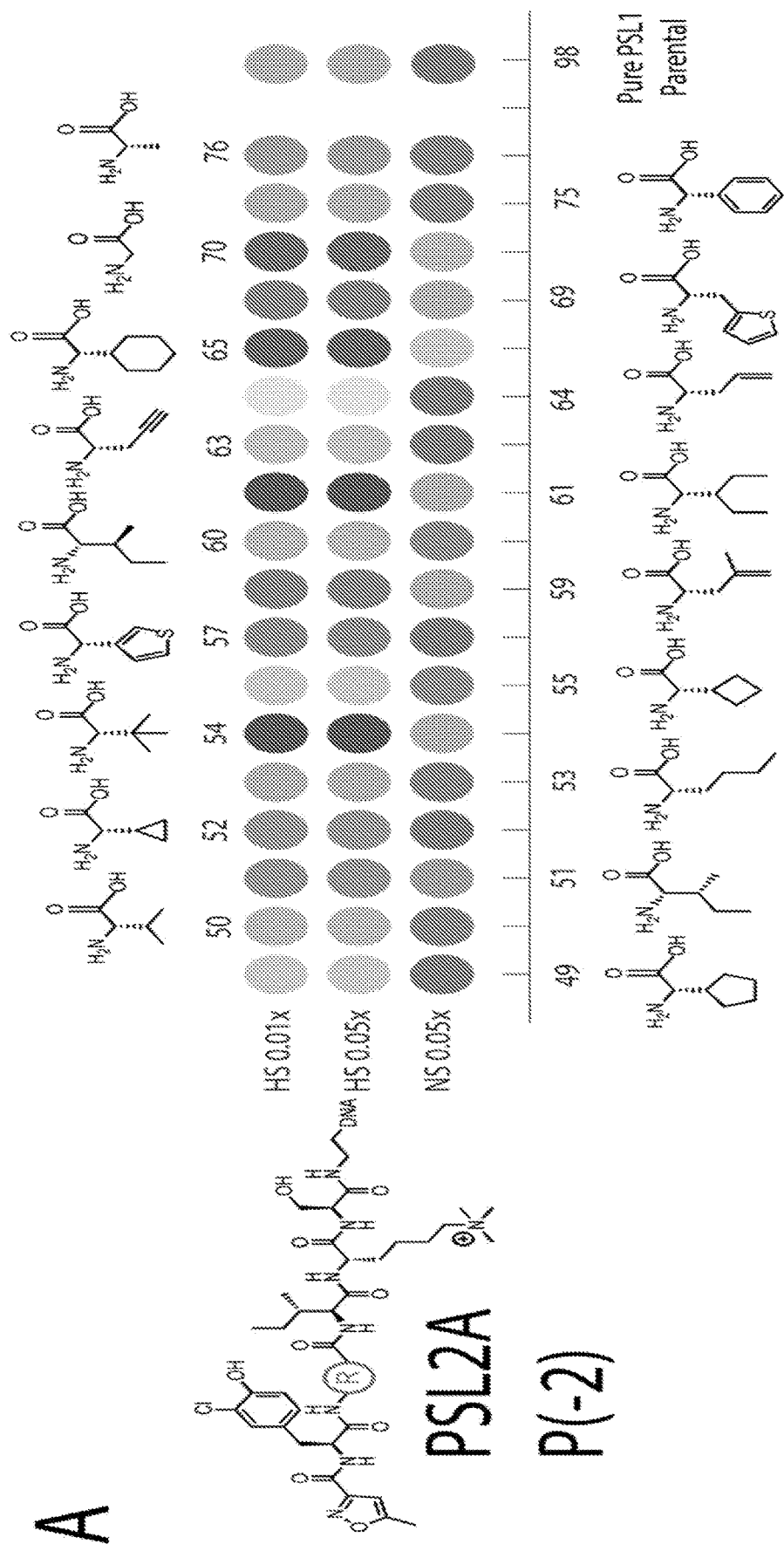
FIGS. 3A-3C. High stringency selections against CBX8 ChD. Compared to normal stringency as three on-bead effective protein concentrations (1×, 0.1×, and 0.05×), we applied high stringency (HS) as increased washing cycles and lower on-bead protein concentration (0.01×, ~1 μM on-bead effective protein concentration) in the selection of PSL2 library against CBX8 ChD. A heat map is presented for the comparison of enrichment between normal stringency 0.05×and high stringency 0.05×/0.01×. Representative monomer structures are presented. Enrichment was calculated relative to non-ligand from DNA sequencing.
Figure 3B:
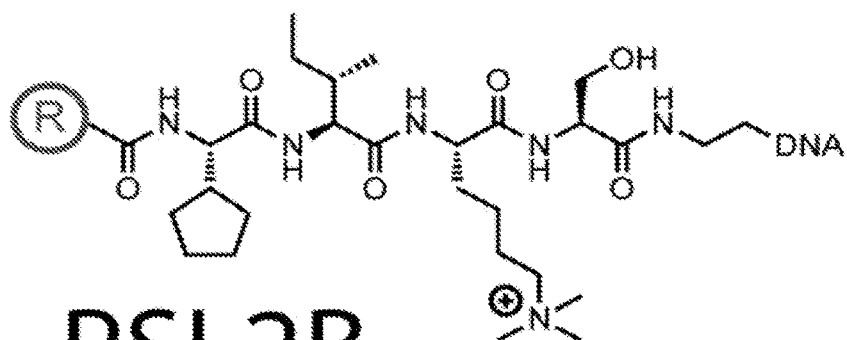
Figure 3B:
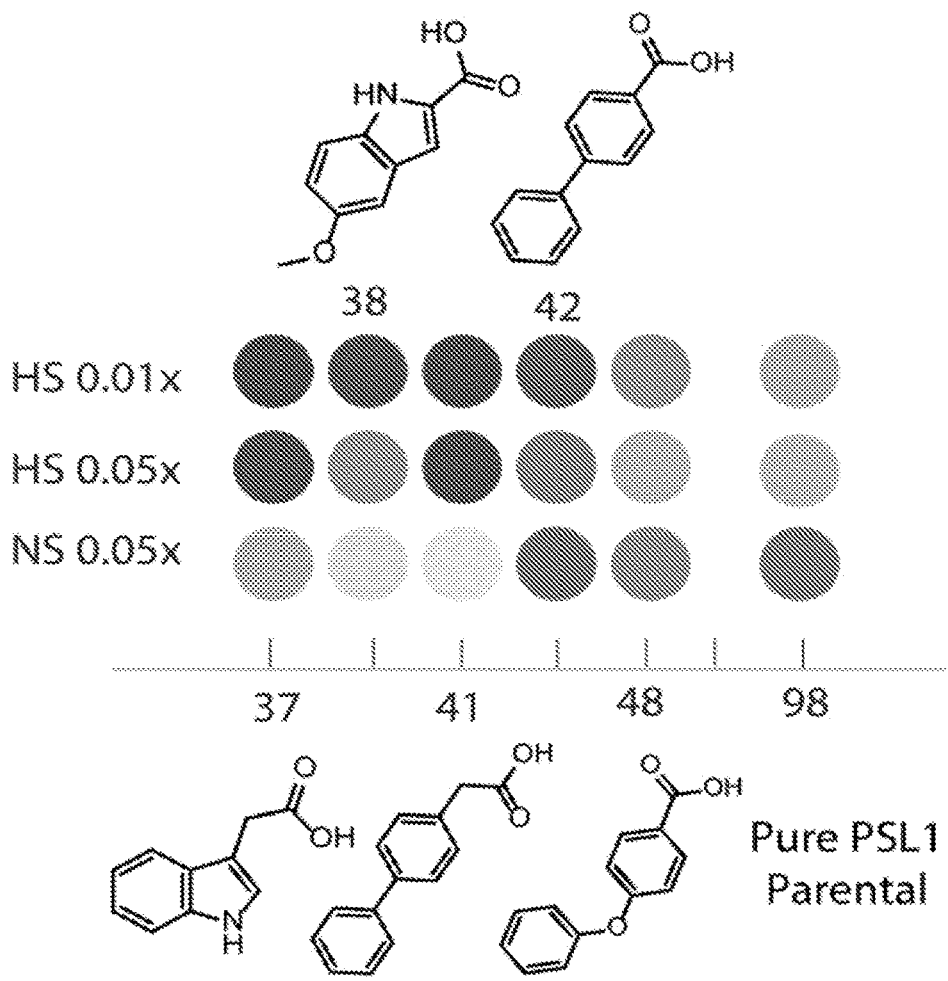
Figure 3C:
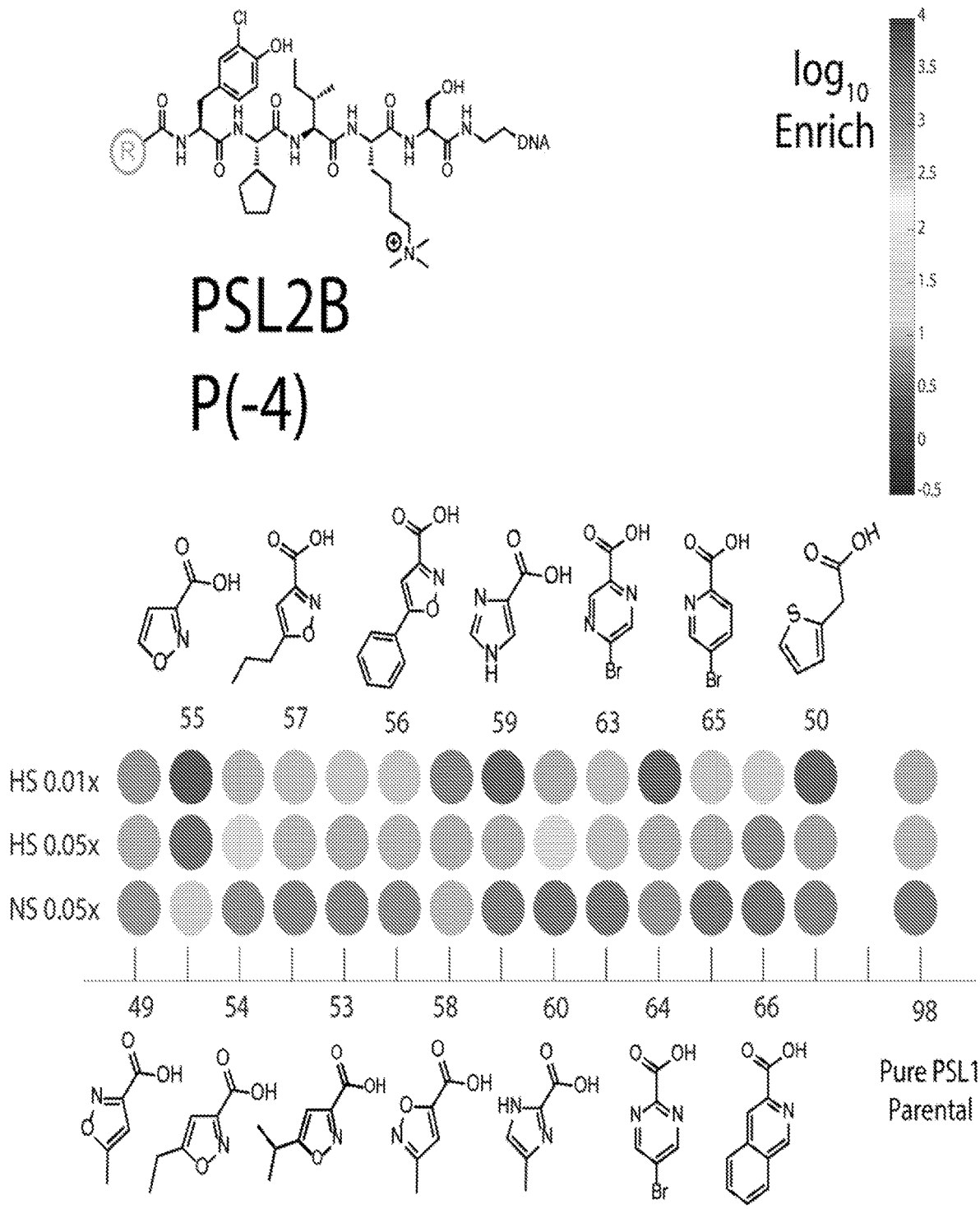

To increase the stringency of the affinity selection assay, we reduced the on-bead protein concentration either 5-fold from the lowest of the three concentrations from the previous selection and increased the bead wash number cycles and time (FIGS. 3A-3C). As expected, we now observed greater differential enrichment among high enriching ligands under the previous conditions.

Under these conditions, valine at P(−2) (PSL2A_50) now showed higher enrichment than cyclopentylglycine (PSL2A_49), consistent with off-DNA competitive FP assays (FIG. 1B). Among additional substitutions at the −2 position, we now observe the highest enrichment of cyclopropylglycine (PSL2A_52), 3-thienylglycine (PSL2A_57), and 1-alanine (PSL2A_76) (FIG. 3A). This was confirmed off-DNA using the competitive FP assay, where cyclopropylglycine (PSL2A_52) and 3-thienylglycine (PSL2A_57) have higher binding affinity to CBX8 than cyclopentylglycine (Table 1A). Enrichment of other monomers at P(−2) decreased roughly with increasing side chain size, as anticipated Similar enrichment was observed for cyclobutaneacetic acid (PSL2A_55), propargylglycine (PSL2A_63), and allylglycine (PSL2A_64), and decreased enrichment was found for allo-isoleucine (PSL2A_51), isoleucine (PSL2A_60), norleucine (PSL2A_53), and phenylglycine (PSL2A_75) compared to parental (PSL2A_1 and PSL2A_49).

As with the low stringency selections, few substitutions at either P(−1) and P(−3) positions suggested significant gains in affinity could be achieved. As with the −2 position, the HS selection was able to resolve high and medium binders at the −4 position (FIG. 3C). 3-isoxazole with various substituents (PSL2B_53, 54, 56, 57) 5-bromo-2-pyrazinecarboxylic acid (PSL2B_63), 5-bromopyridine-2-carboxylic acid (PSL2B_65), and isoquinoline-3-carboxylic acid (PSL2B_66) have higher enrichment to CBX8 than the parental ligand, while 2-thiopheneacetic acid (PSL2B_50) and 1H-imidazole-4-carboxylic acid (PSL2B_59) showed significantly lower enrichment. These results were consistent with both published and PSL1 SAR of ligands to CBX8, which showed increased affinity for benzoyl caps with lipophilic para substituents (Denton et al., 2018).

TABLE 1

Ligands with combined synthons, displaying either increased enrichment or selectivity, were synthesized off DNA by solid phase peptide synthesis.

| Compound | R = | IC$_{50}$ (µM) | | |
|---|---|---|---|---|
| | | CBX6 | CBX7 | CBX8 |
| | A (peptide scaffold shown above) | | | |
| KED98 (PP) | (5-methylisoxazole-3-carboxamide-chlorotyrosine-cyclopentylglycine) | 34 ± 1.3 | 83 ± 1.6 | 14 ± 1.3 |
| SW2_101B (PSL2B_48) | (4-phenoxybenzamide-cyclopentylglycine) | NB | ND (>100) | 12 ± 1.1 |
| SW2_89 (PSL2B_42) | (biphenyl-4-carboxamide-cyclopentylglycine) | ND (Aggreg.) | 22 ± 1.1 | 13 ± 1.1 |

TABLE 1-continued

Ligands with combined synthons, displaying either increased enrichment or selectivity, were synthesized off DNA by solid phase peptide synthesis.

| Compound | R = | IC$_{50}$ (μM) | | |
| --- | --- | --- | --- | --- |
| | | CBX6 | CBX7 | CBX8 |
| SW2_90 (PSL2A_52) | | 0.36 ± 0.054 | 0.82 ± 0.12 | 2.1 ± 0.51 |
| SW2_101E (PSL2A_57) | | 4.8 ± 0.58 | 83 ± 1.1 | 3.1 ± 0.84 |
| SW2_101F | | ND (>100) | 1.6 ± 0.32 | 4.0 ± 1.1 |
| SW2_101A | | 98 ± 26 | 35 ± 9.4 | 40 ± 8.3 |

TABLE 1-continued
Ligands with combined synthons, displaying either increased enrichment or selectivity, were synthesized off DNA by solid phase peptide synthesis.
| Compound | R = | IC$_{50}$ (μM) | | |
| --- | --- | --- | --- | --- |
| | | CBX6 | CBX7 | CBX8 |
| | 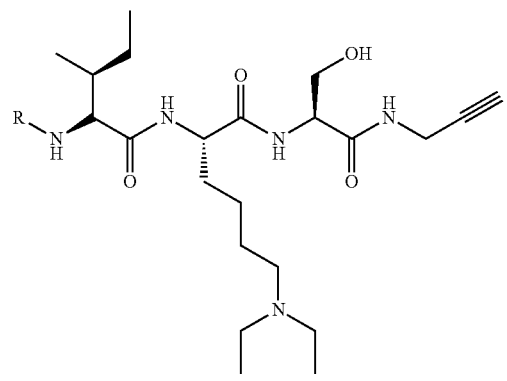 B | | | |
| SW2_110A | 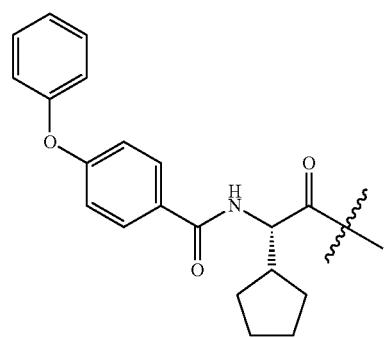 [SMILES: *C(=O)[C@@H](NC(=O)c1ccc(Oc2ccccc2)cc1)C1CCCC1] | ND (Aggreg.) | ND (Aggreg.) | >7.0 (Aggreg.) |
| SW2_104B | 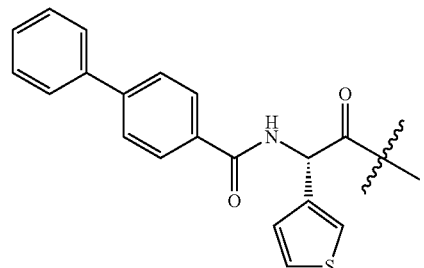 [SMILES: *C(=O)[C@@H](NC(=O)c1ccc(-c2ccccc2)cc1)C1CCCC1] | ND (Aggreg.) | ND (Aggreg.) | >15 (Aggreg.) |

TABLE 1-continued

Ligands with combined synthons, displaying either increased enrichment or selectivity, were synthesized off DNA by solid phase peptide synthesis.

| Compound | R = | IC$_{50}$ (μM) | | |
| --- | --- | --- | --- | --- |
| | | CBX6 | CBX7 | CBX8 |
| SW2_110B | 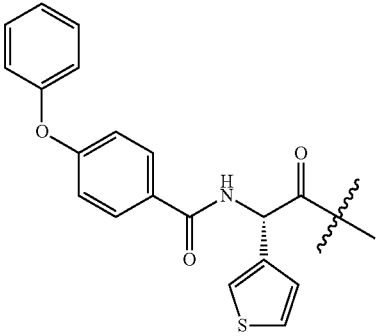 [SMILES: *C(=O)[C@@H](NC(=O)c1ccc(Oc2ccccc2)cc1)c1ccsc1] | ND (Aggreg.) | ND (Aggreg.) | >5.7 (Aggreg.) |
| SW2_104A | 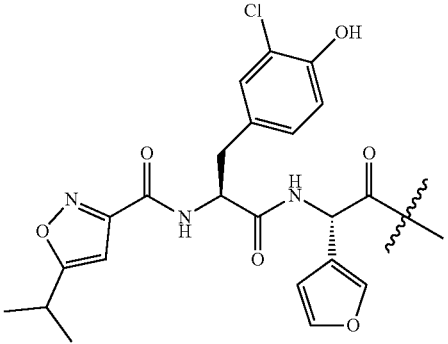 [SMILES: *C(=O)[C@@H](NC(=O)[C@H](Cc1ccc(O)c(Cl)c1)NC(=O)c1cc(C(C)C)on1)c1ccoc1] | 2.7 ± 0.70 | 4.8 ± 0.94 | 1.6 ± 0.62 |

IC50 values for each ligand against CBX6, CBX7, and CBX8 ChD, were measured with the fluorescence polarization assay.
IC50 values are reported as the average of quadruplicates ± s.d.
NB: No binding.
ND: Not detectable.
Either compound showed no observable binding or IC50 >100 μM in the assay.
Aggreg.: Aggregations.
IC50 cannot be determined due to the poor solubility in the assay.

PSL2 Hit Structure Optimization

From both sets of selection assays, we identified monomers that indicated increases in both selectivity and affinity to CBX8 compared to the parent compound. We next combined the selective monomers at the −3+−4 (either the phenoxybenzyl or biphenyl) with the high affinity monomers identified for the −2 position (cyclopropyl, thienyl) (Table 1). SW2_101F had increased affinity for CBX8 compared to KED98, but gave decreased selectivity in binding to CBX7. Interestingly, the biphenyl cap gave significantly reduced affinity for both CBX8 and CBX7 when paired with the P(−2) cyclopropyl glycine (SW2_101A), while in the context of the P(−2) cyclopentyl glycine (SW2_89) there was little change in affinity. For compounds SW110B and SW104B the affinity was not measurable due to solubility issues. Combining 5-isopropyl-3-isoxazole at position −4 with the 3-thienylglycine at position −2 in SW2_104A did increase affinity further compared to the thienylglycine alone (SW2_101E).

These results were confirmed using direct fluorescence polarization assays to measure K$_d$ values (Table 2). The K$_d$ of SW2_110A-FL for the CBX8 ChD was determined to be ∼800 nM, which was confirmed using a microscale thermophoresis (MST) binding assay. The affinity was a modest decrease in affinity compared to the KED97L-FL, the optimal molecule developed from PSL1; however, SW2_110A-FL displayed dramatic improvements in selectivity. This compound was completely selective for CBX8 over CBX4 and CBX6, while maintaining 20-fold selectivity over CBX7 and 5-fold selectivity over CBX2. In contrast, the selectivity of SW2_104A for CBX8 ChD was not significantly different than KED97L, even though the affinity to all paralogs was increased over 15-fold, with a K$_d$ of 2.9 nM for CBX8 (5.4 nM using MST), making it the tightest CBX8 chromodomain ligand to date.

Combining phenoxyphenyl cap with the thienylglycine at P(−2) (SW2_110B-FL) showed no comparably observable binding in the direct binding assay due to poor solubility, and the binding constant determined using MST was similar to that obtained for SW2_110A-FL.

TABLE 2
Quantitative analysis of PSL2 hits binding to PcG CBX ChDs by direct fluorescence polarization assays.
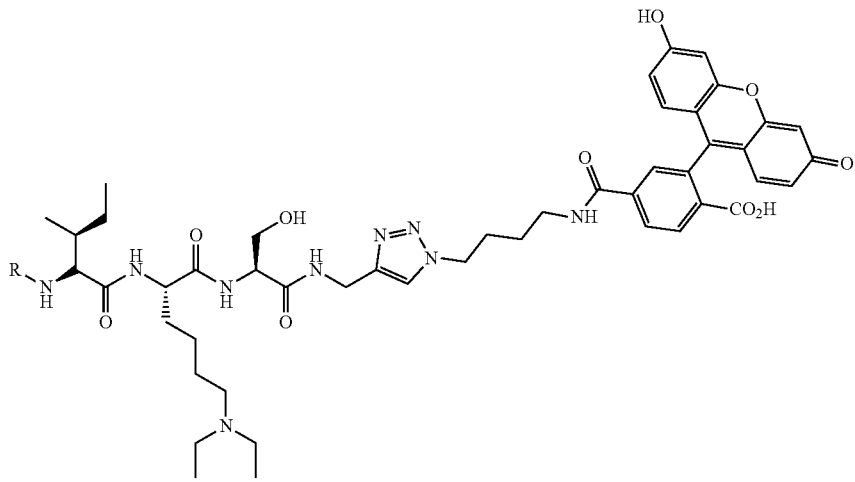
| Compound | R = | CBX Protein Chromodomain $K_d$ (μM) | | | | |
| --- | --- | --- | --- | --- | --- | --- |
| | | CBX2 | CBX4 | CBX6 | CBX7 | CBX8 |
| KED97L-FL | | 1.1 ± 0.38 | 2.7 ± 0.36 | 0.26 ± 0.12 | 4.7 ± 0.88 | 0.24 ± 0.030 |
| SW2_110A-FL | | 4.6 ± 0.89 | NB | NB | >16 ± 5.2 | 0.80 ± 0.23 (MST: 0.70 ± 0.11) |
| SW2_104A-FL | | 0.051 ± 0.036 | 0.17 ± 0.043 | 0.014 ± 0.0040 | 0.84 ± 0.38 | 0.0029 ± 0.00080 (MST: 0.0054 ± 0.0010) |

TABLE 2-continued

Quantitative analysis of PSL2 hits binding to PcG CBX ChDs by direct fluorescence polarization assays.

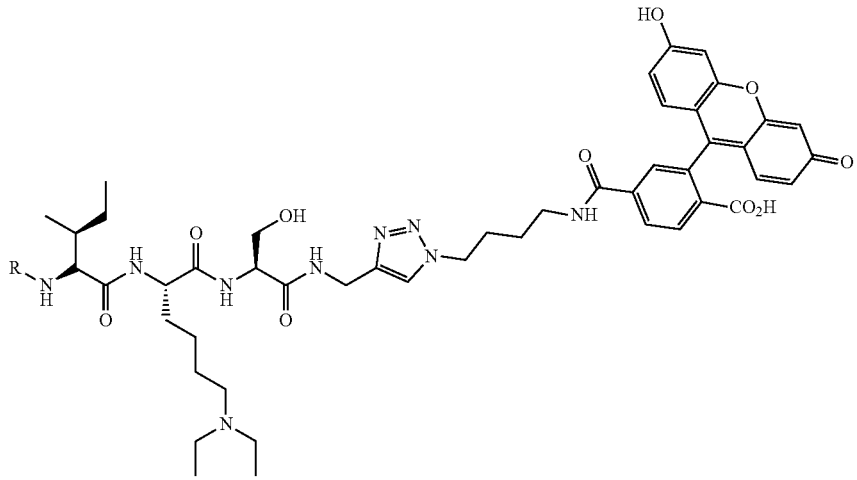

| Compound | R = | CBX2 | CBX4 | CBX6 | CBX7 | CBX8 |
|---|---|---|---|---|---|---|
| SW2_110B-FL | | ND | NB | NB | NB | ND (MST: 0.82 ± 0.10) |

Kd values are reported as the average of quadruplicates ± s.d.
NB: No binding.
ND: Not detectable (Compound showed no comparably observable binding in the assay).
MST: MicroScale Thermophoresis. MicroScale Thermophoresis assay was utilized as an alternative for quantifications of ligand-protein interactions.

Structural Basis of SW2_110A Association with CBX8 CD

To investigate the structural basis of inhibitor binding, we utilized NMR spectroscopy. We collected a series of $^{1}H,^{15}N$ heteronuclear single quantum coherence ($^{15}N$-HSQC) spectra on $^{15}N$-labeled CBX8 CD upon the titration of SW2_110A. Addition of the inhibitor led to substantial changes in the CBX8 CD spectrum, including chemical shift perturbations (CSPs) and disappearance of resonances, indicating binding (FIG. 4 and S14). Mapping the CSPs onto the solved structure of the CD-H3K9me3 complex reveals that residues involved in binding are clustered in and around the peptide binding pocket. This indicates that the inhibitor functions by directly blocking histone tail binding, as expected. Importantly, the limited solubility of the inhibitor at high concentrations required introduction of DMSO. A control titration with DMSO alone showed minimal shifts compared to the inhibitor sample.

We have previously determined the structural basis of H3K27me3 and H3K9me3 binding using NMR spectroscopy (Connelly et al). Comparing the CSPs induced upon addition of SW2_110A to those of an H3K27me3 peptide (residues 21-33?) (SI4) reveals that the largest differences are in resonances corresponding to E43, N47, and I48, as well as D50, L53, and L54. Both subsets of resonances are significantly more perturbed upon inhibitor binding as compared to H3K27me3 and were not significantly perturbed upon addition of DMSO alone. These resonance differences highlight the importance of these residues in binding and the differences in binding mode of the inhibitor compared to the H3K27me3 peptide. Residues E43, N47, and I48 are adjacent to the expected location of the P(−1) and P(−2) side-chains, which are Arg(P-1) and Ala(P-2) in the H3K27 peptide. In addition, residues D50, L53, and L54 lie where the phenoxyphenyl group is expected to bind. A number of resonances (corresponding to V10, F11, A12, E14, A15, K33, G34, T41, and L49) disappear upon binding. These lie in the β1 strand, and the β1-β2 loop, which contain the aromatic cage residues. Based on the crystal structures of the apo CBX8 CD and the CD in complex with H3K9me3, this region is stabilized upon histone tail binding. The disappearance of these peaks upon addition of SW2_110A suggests that, in contrast, inhibitor binding may not fully stabilize this region instead leading to conformational exchange in the bound state on the intermediate NMR timescale.

Interestingly, side-chains identified as important for determining selectivity associate with regions of the CD that are conserved between homologues. Indeed, most of the residues that differ between the CD homologues do not exhibit CSPs upon SW2_110A binding with two exceptions: A15, which is a Ser in CBX6 and CBX7, and S36, which is an Ala in CBX6 and a Pro in CBX7. Neither of these residues, however, are expected to make direct contact with the inhibitor. The fact that several resonances disappear indicates a high level of conformational dynamics of the CD on the intermediate timescale. These data suggest that rather than differences in the manner in which each CD directly coordinates with the inhibitor, specificity is likely due to a difference in the accessible conformational ensemble available to each CBX CD. This could be modulated by small differences in the CD sequence ultimately leading to differences in the size and nature of chemical groups that can be accommodated.

Cellular Selectivity Studies
Pulldown Assay

Figure 5A:
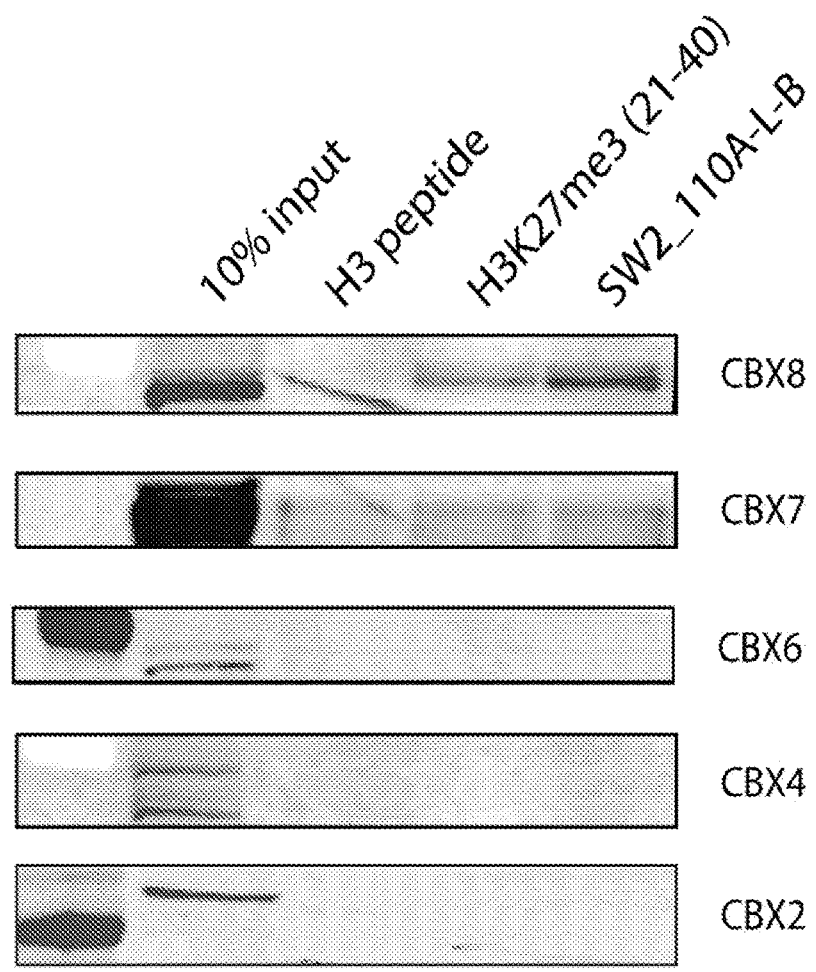
FIG. 5A depicts peptide pull-downs from HEK293T nuclear lysates using biotin-labeled histone peptides and biotin-labeled SW2_110A (SW2_110A-B). In immunoblot analysis, SW2_110A-B selectively pulls down endogenous CBX8 from the lysate.

The CBX chromodomains demonstrate significant structural flexibility, bringing into question whether recombinant chromodomains accurately recapitulate binding properties of the chromodomains found within the context of fully formed PRC1. Therefore, we utilized a biotinylated derivative of SW2_110A, SW2_110A-B, to profile binding to CBX8 and its paralogs from lysates using affinity purification (FIG. 5A). Purification from HEK293T nuclear lysates was performed with SW2_110A-B, along with biotinylated unmodified histone H3 peptide (21-44) and biotinylated histone H3K27me3 (21-44). SW2_110A-B selectively pulls down CBX8 from the nuclear lysate, without enriching any other paralogs, in support of the in vitro competitive FP assay results with recombinant chomodomains. Further, this interaction is abrogated upon incubation of lysates with free ligand.

Sequential Salt Extraction

Figure 5B:
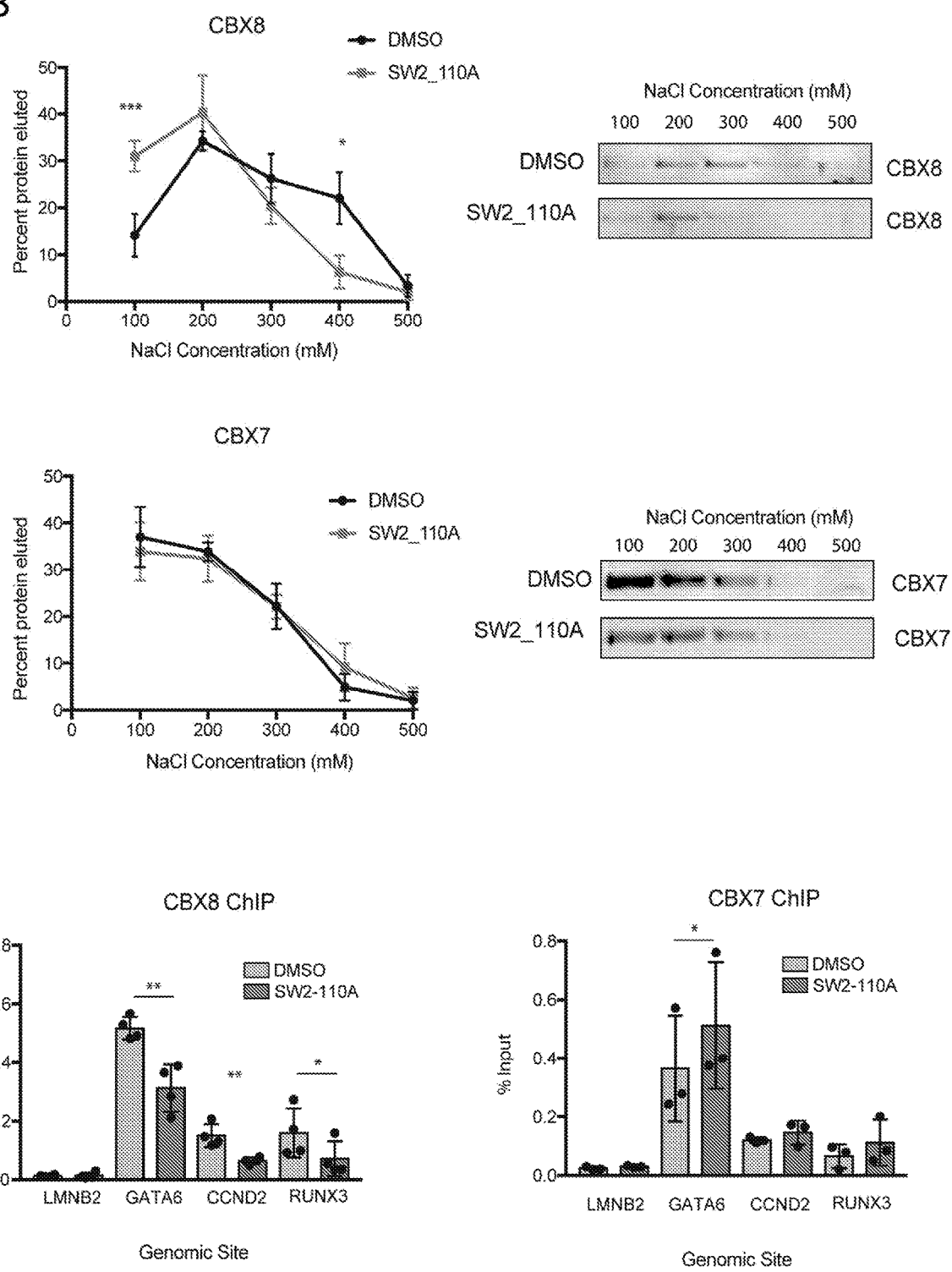
FIG. 5B shows analysis and quantification of SW2_110A in abrogating bulk binding affinity of endogenous CBX proteins to chromatin in HEK293T cells by Sequential Salt Extraction. Quantitation of amount of CBX in each fraction as a percent of total CBX proteins. n=3 independent biological replicates, errors bars represent standard error of the mean (SEM), P-values were calculated using Student's two-tailed t-test: *P<0.05, **P<0.01.

We next performed sequential salt extraction (SSE) to explore if our selective CBX8 ligand can block and attenuate bulk CBX8 chromatin binding. This assay is useful in evaluating the relative binding affinities of chromatin-bound complexes and can be used to qualitatively evaluate the impact of mutation or inhibition of individual chromatin binding domains on the bulk chromatin binding affinity of protein complexes (Porter et al. 2017, Connelly et al. 2018, Marian et al. 2018). Chromatin bound proteins were extracted from isolated nuclear pellets using increasingly stringent salt washes containing SW2_110A. From our results, we demonstrated the selectivity of SW2_110A for CBX8 over CBX7 in abrogating the bulk chromatin binding in the sequential salt extraction assay (FIG. 5B).

ChIP-qPCR

Figure 5C:
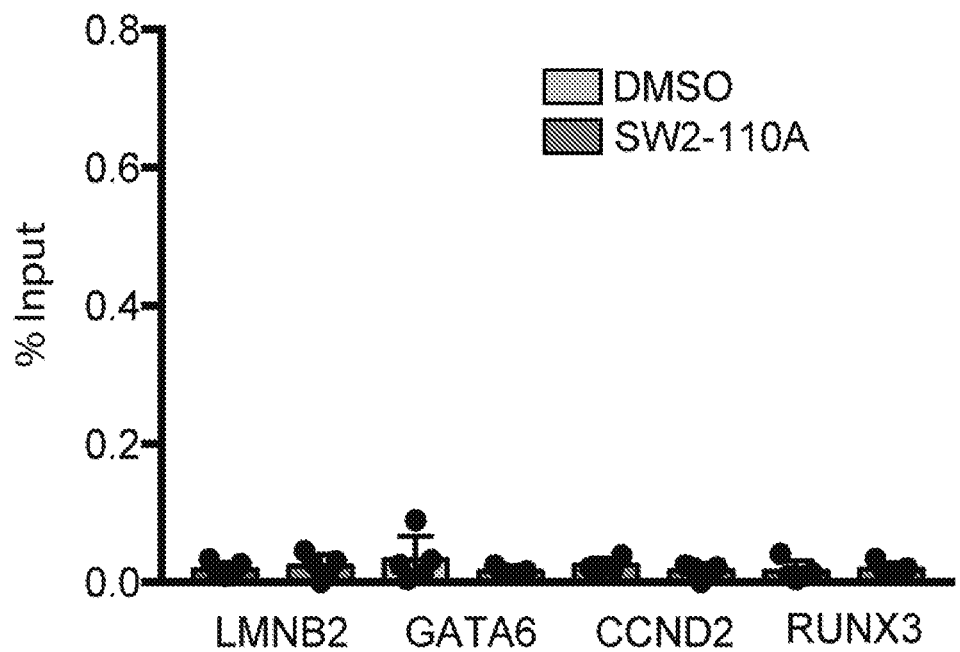
FIG. 5C depicts chromatin immunoprecipitation (ChIP) followed by quantitative PCR of CBX8/CBX7 regulated genes in Hs68 fibroblast cell line. ChIP-qPCR was used to evaluate the ability of SW2_110A to disrupt endogenous CBX protein associations with chromatin in cells.

In order to evaluate the local target specificity of CBX8 hit compound, ChIP followed by quantitative PCR (ChIP-qPCR) was performed to confirm the in vivo selectivity of compound SW2_110A (FIG. 5C). Previous ChIP-Seq using antibodies against CBX6, CBX7 and CBX8 in Hs68 fibroblast cells revealed that those paralogs co-localize at the majority of genomic sites (Pemberton et al., 2014). We selected representative target loci and confirmed the enrichment of CBX7 and CBX8 at those loci using ChIP-qPCR (Connelly et al., 2018). Upon incubation of cells with SW2_110A, we observe significant reduction of CBX8 binding at these sites. CBX7 binding was unaffected or even increased upon treatment with SW2_110A, which was similarly observed in the CBX8 knockdown. Since the CBX paralogs all bind the same H3K27me3 sites, it is possible that selective reduction of CBX8 at a genomic locus could increase the enrichment of other paralogs at the same site.

In conclusion, sequential salt extraction, pulldown assays, and ChIP-qPCR assays demonstrate that SW2_110 binds selectively to native CBX8 and selectively inhibits CBX8 binding to chromatin.

Evaluation of Cytosolic Access Using ChloroAlkane Penetration Assay (CAPA)

Figure 6A:
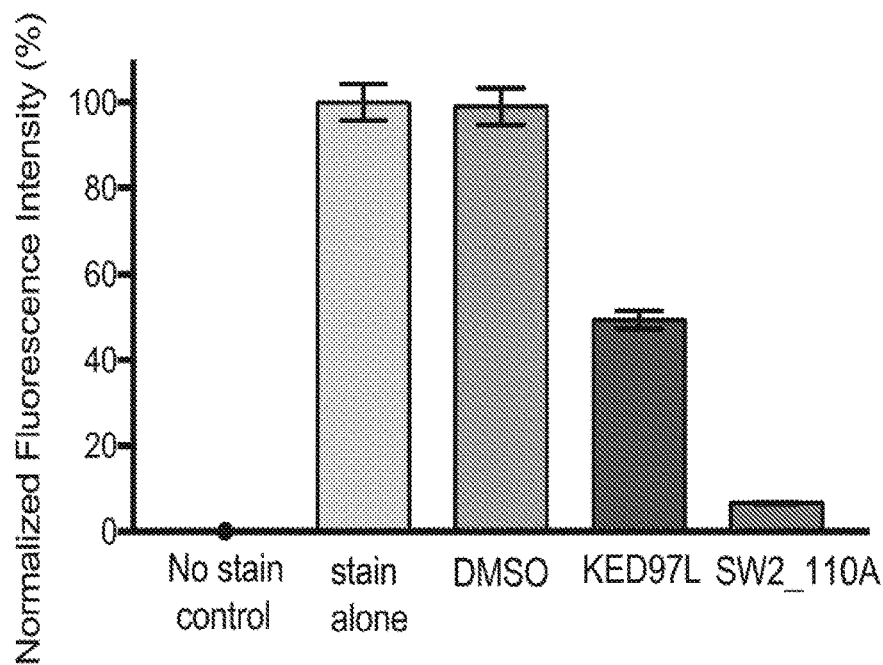
FIG. 6A shows relative cytosolic access of exogenous molecules SW2_110A-CA and KED97L-CA was evaluated by chloroalkane penetration assay (CAPA) (Top Panel). Dose-dependent cytosolic access of SW2_110A-CA was quantified by preincubations of different concentrations of SW2_110A, followed by HT-TAMRA dye in the CAPA. $CP_{50}$ of SW2_110A-CA was evaluated and averaged from three independent curve fits (Bottom Panel). 10 000 cells were used in flow cytometry for each sample at each concentration. Mean fluorescence was normalized, using no-pulse, only dye chase as 100% signal and a no-pulse/no-chase as 0% signal.
Figure 6A:
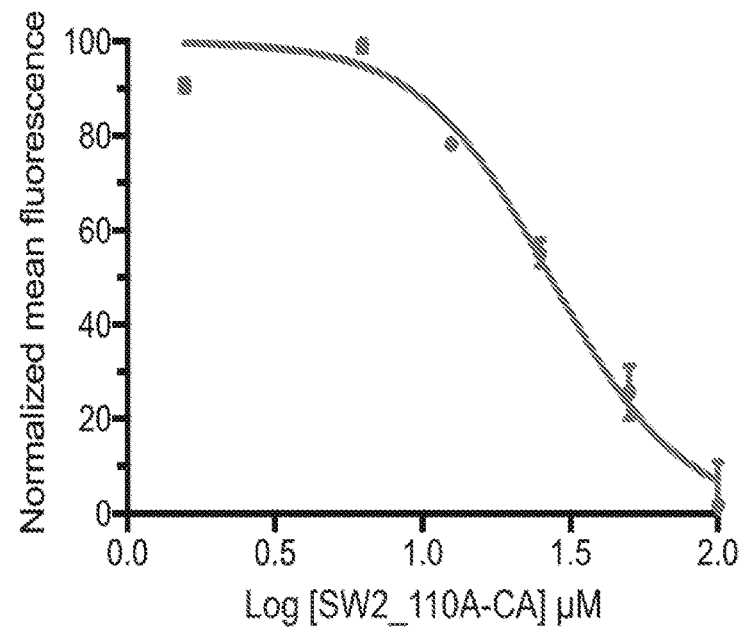

The ChIP-qPCR results indicate that SW2_110 has increased cell permeability compared to KED97. To confirm this difference, we again used the CAPA cell penetration assay recently developed by the Kritzer Lab (Peraro et al. 2017). CAPA is easy to perform, quantitative, and measures compound within the cytosol without interference from molecules trapped in endosomes. The approach is a pulse-chase experiment involving a HeLa cell line stably transfected with a cytosolic HaloTag protein (Los 2008 reference). These cells were incubated with compounds conjugated to a chloroalkane (CA) (pulse), where the cytosolic fraction will covalently react with the HaloTag protein. The cells are then treated with CA-TAMRA dye (chase), which reacts with the unblocked HaloTag. The red fluorescence is quantified using flow cytometry, which is inversely proportional to the CA-molecule cytosolic concentration. SW2_110A conjugated to the chloroalkane (denoted SW2_110A-CA) was compared to KED97L-CA, which has comparable CBX8 binding affinity (400 nM). An increase in permeability was observed with SW2_110A-CA showing a $CP_{50}$ of 25 µM (FIG. 6A).

Cellular Activity

We next evaluated the activity of SW2_110A in a CBX8-dependent cell line. Previous studies have identified a paralog-specific interaction between CBX8 and the AF9/ENL subunits of the super elongation complex (Monroe et al., 2011; Mueller et al., 2007). It has also been confirmed that CBX8 interacts with the MLL-AF9 translocation product that is the causative factor in a subset of leukemias (Garciá-Cuéllar et al., 2001; Hemenway et al., 2001; Monroe et al., 2011; Tan et al., 2011). Previous studies found that CBX8 is required for leukemogenesis in an MLL-AF9 mouse model of leukemia, as well as for viability of leukemia cell lines with MLL-AF9 translocations (Tan et al. 2011, Ayton and Cleary, 2003; Kumar et al., 2004). MLL-AF9 mediated oncogenesis is thought to be mediated primarily through aberrant gene activation (Sitwala et al., 2008; Yokoyama and Cleary, 2008; Armstrong et al., 2002), making the involvement of the CBX chromodomain unclear, as its presumed canonical role is binding of H3K27me3 to mediate transcriptional repression.

THP1 Cell Viability

Figure 6B:
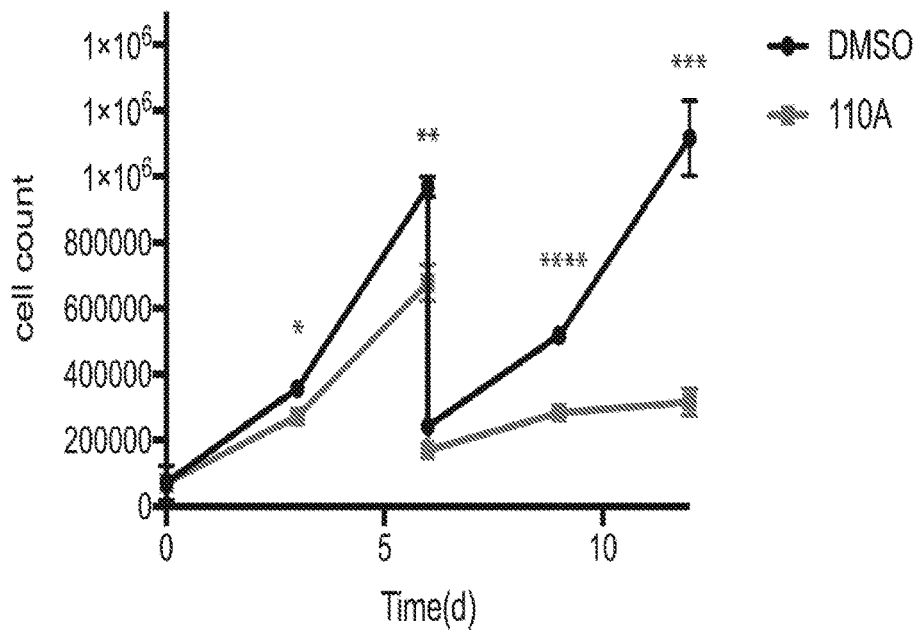
FIG. 6B shows cellular effects of SW2_110A. Treatment of THP1 cells with 100 μM SW2_110A inhibits cell proliferation (Top Panel), but not in control cell line K562 (Bottom Panel). s.d. was represented by error bars. (n=3, three biological replicates with three technical replicates for each biological replicates) $IC_{50}$ of SW2_110A inhibiting THP1 cell proliferation was quantified by a 12-day dose-dependent curve. The $IC_{50}$ is reported as the 95% confidence interval.
Figure 6B:
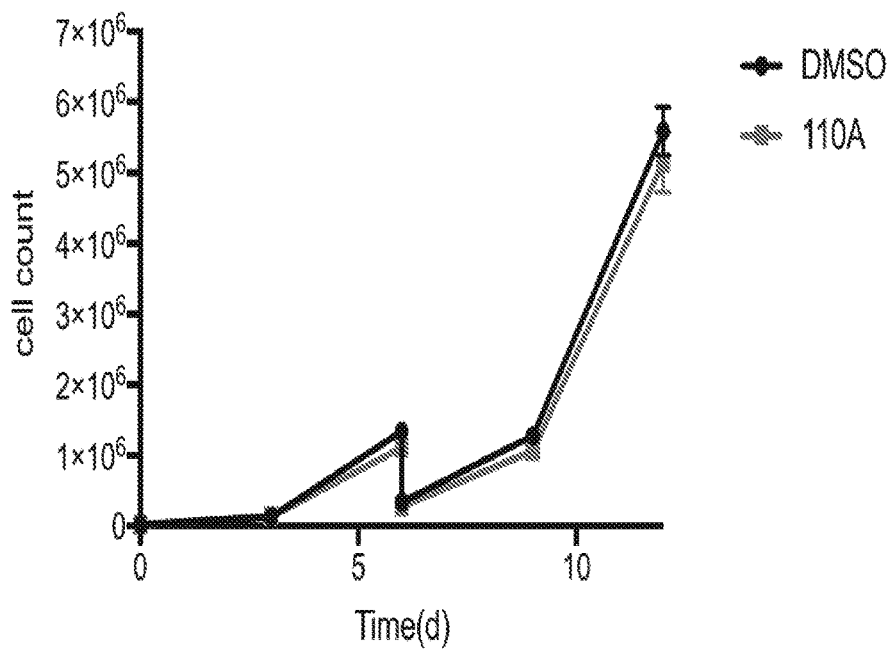
Figure 6C:
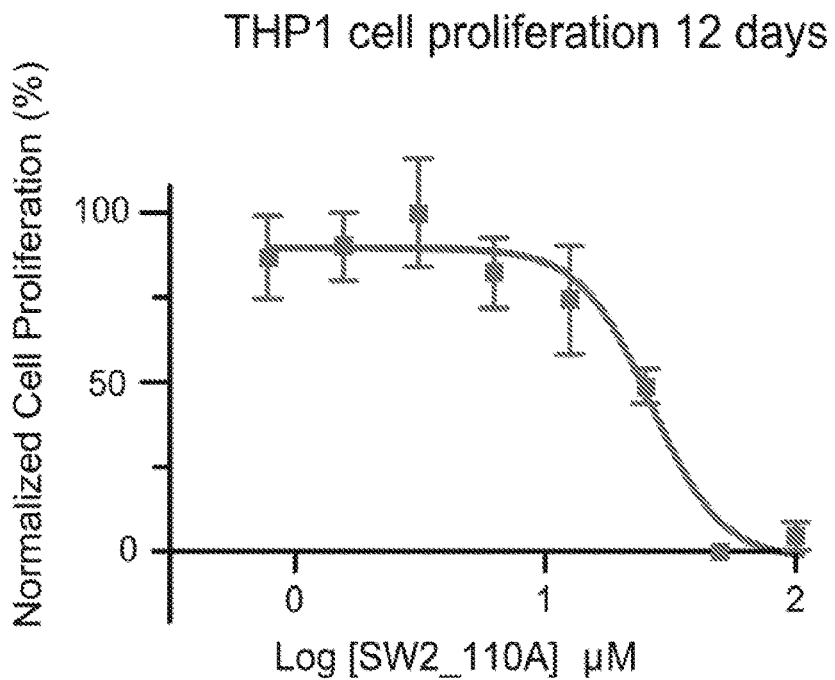
FIG. 6C shows THP1 cells were treated with 100 μM SW2_110A for 24 h (Top Panel). Relative transcript changes of HOXA9 (Bottom Panel), a CBX8 activated gene in MLL-AF9 leukemogenesis, was determined as fold over DMSO treated. Gene expression level was normalized to B2M. P-values were calculated using Student's two-tailed t-test: *P<0.05, P<0.01,*P<0.001, ****P<0.0001.
Figure 6C:
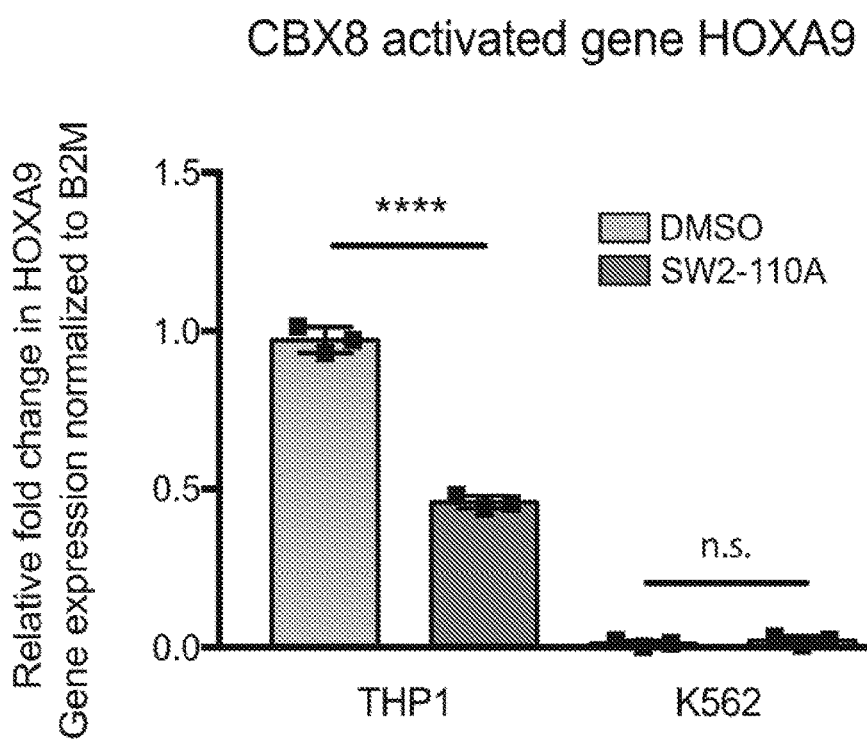
Figure 7A:
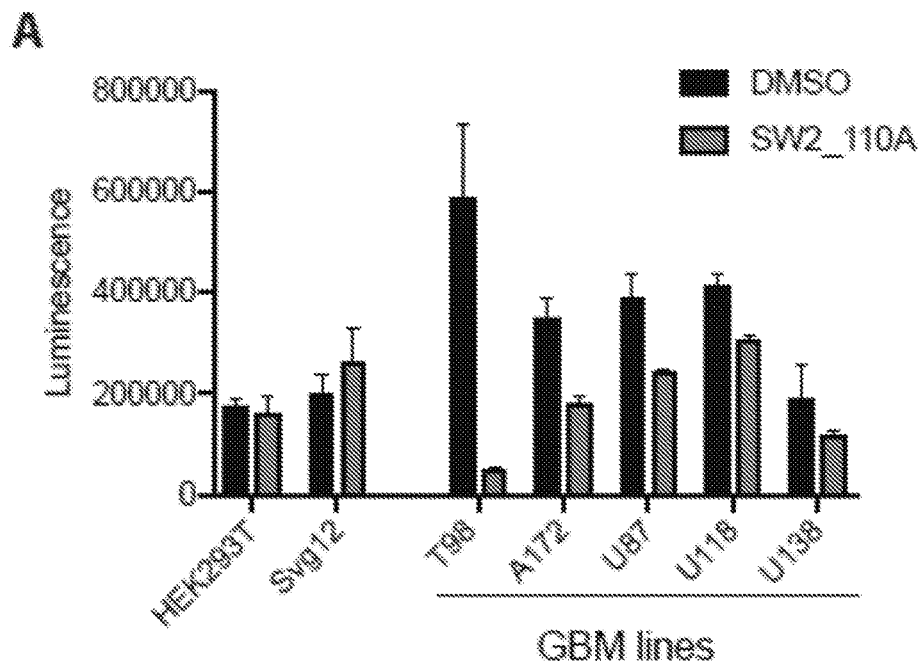
FIG. 7A: CBX8 inhibitor SW2_110A selectively inhibits the growth of GBM cell lines (T98, A172, U87, U118, U138) but not human astrocyte line Svg12 or transformed kidney line HEK293T. Cells were plated at 5,000 cell/well in a 96 well tissue culture dish and grown for 5 days in the presence of DMSO or 100 µM SW2_110A. The cell growth was measured using Cell-titer Glo® and plotted as raw luminescenece values.
Figure 7B:
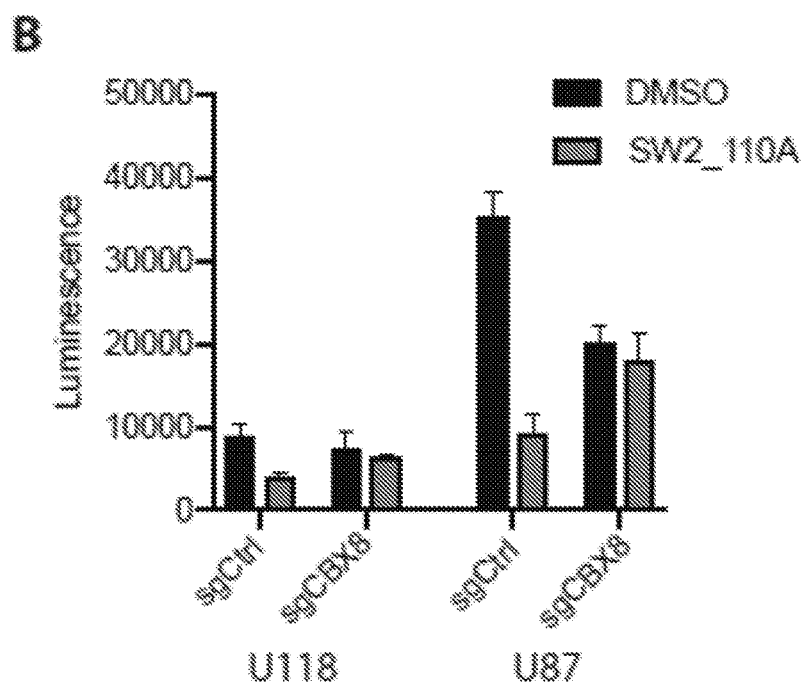
FIG. 7B: GBM cell lines U118 and U87 with knockout of CBX8 were generated using CRISPR. Control (sgCtrl) and CBX8 (sgCBX8) knockout cells were plated at 5,000 cell/well in a 96 well tissue culture dish and grown for 5 days in the presence of DMSO or 100 µM SW2_110A. The cell growth was measured using Cell-titer Glo® and plotted as raw luminescenece values.

First, we evaluated the viability of THP1, an MLL-AF9 translocated leukemia cell line, cultured with SW2_110A. Using 100 µM treatments, we observed a significant proliferation decrease starting at 3 days with almost ~80% inhibition after 12 days of treatment compared to DMSO. In contrast, the growth of control leukemia cell line K562 with a BCR-ABL translocation was not affected (FIG. 6B). The $IC_{50}$ of SW2_110A for growth inhibition of the THP1 cells after 12-day treatment was determined to be 25.0±1.1 µM (FIG. 6C) Similar effects on viability were observed for the more potent but less selective ligand 104A.

HOXA9 Gene Expression

In order to investigate how SW2_110A decreases THP1 cell viability, we examined whether CBX8 inhibition affects transcriptional activation by MLL-AF9. A previously well-established mechanism of MLL-AF9 transformation is the constitutive activation of the HOX genes, particularly HOXA9 (Ayton and Cleary, 2003; Kumar et al., 2004). We utilized qRT-PCR to demonstrate that HOXA9 gene expression is significantly decreased (>50%) upon SW2_110A treatment in THP1 cells consistent with previous reports, indicating a requirement on CBX8 for HOXA9 expression (Tan et al. 2011). (FIG. 6C) In contrast, SW2_110A did not affect HOXA9 gene expression level in a non-MLL-AF9 leukemic cell line, K562, consistent with their different oncogenic drivers. While it remains to be determined how CBX8 contributes to HOXA9 activation in MLL-AF9 leukemogenesis, these results indicate that the chromodomain is involved and is a potential therapeutic target in these cancers. In addition, SW2_110A is a promising chemical probe for mechanistic evaluation of CBX8 in transcription and oncogenesis, and will serve as starting point for determining the potential of CBX8 as a therapeutic target.

Using two generations of DNA-encoded chemical libraries, we identified selective, cell permeable, peptidomimetic ligands for the CBX8 ChD. While increased potency and partial selectivity was achieved after the first-round selection in PSL1, sequential custom library design led to highly increased cell permeability and selectivity. While DELs are predominantly used for hit generation to initiate traditional optimization efforts, this work highlights the potential benefits of including DNA-encoded chemistry within the design-make-test-analyze cycles (DMTA cycles) of medicinal chemistry. Compared with traditional synthesis, purification, and screening, this DNA-encoded approach is cheaper, faster, and less labor-intensive method for the identification and optimization of ligands. These benefits largely arise from the nature of the in vitro selection assay. In this assay, it is the concentration of the protein target (not the synthetic ligand) that drives the binding event. Thus, the concentration of the DNA-encoded ligands is insignificant and can be very low, which allows synthesis on a very small scale. Monomers can be incorporated that would be too expensive to include using traditional approaches. Similarly, this approach has a low requirement for purity of the synthetic ligands. While ligand purity can complicate the relationship between the observed enrichment of a molecule and its affinity to the protein target, this can be addressed by performing selections at multiple concentrations, as performed here (Satz, 2015). Conducted carefully, this can yield enrichment binding curves whereby the curve midpoint will correlate with protein affinity and can be unaffected by ligand purity (provided byproducts are non-ligands) (Satz, 2015; Satz, 2016). While the enrichment magnitude is dependent on compound purity, purity is less of an issue for peptides and peptidomimetics, as their synthesis is robust under on-DNA conditions (Halpin et al., 2004; Krusemark et al., 2016). In this work and our prior assay optimization, we observed a good correlation of off-DNA affinities and enrichments in most cases, provided the selection stringency was adequate, which is supportive of similar yields in the on-DNA synthesis.

In the case of the false positive, PSL2A_35, it may be that a side product generated in the reaction with this monomer is the true hit, which could be confirmed with additional testing. Also, this false positive may have arisen due to DNA sequence effects, which could be addressed with redundant barcoding.

Using this methodology, we have identified the tightest binding ligands to date for the CBX8 chromodomain, indicating that screening new combinations of amino acid monomers still can improve the affinity of 6-mer peptidomimetics for this target class. Of particular note, we identified a truncated scaffold lacking the position −4 monomer that retains affinity to CBX8 and displays improved selectivity, especially against the highly homologous CBX6. SW2_110A containing the truncated phenoxyphenyl cap yielded the first CBX ChD ligand to demonstrate complete selectivity for certain isoforms. For this ligand, no binding could be detected to the CBX 4 and 6 ChDs. In prior work with 6-mer ligands, binding to all the Pc ChDs was measurable, with the maximal selectivity achieved being ~20-fold. Understanding the structural basis for this selectivity will facilitate ligand optimization moving forward with CBX8 ChD ligands and for generation of selective ligands to the other Pc ChDs.

Importantly, the removal of a single amino acid reduced the molecular weight and increased hydrophobicity, improving cell permeability compared to the parental peptidomimetic. A major hurdle for developing peptidomimetics as chemical probes is cell permeability. This is particularly challenging for this type of protein-protein interaction, which includes an extended hydrogen bonding network in a beta-sheet-like interaction (Ref). Peptidomimetics that target interactions mediated by an alpha helix (such as stapled peptides) have the benefit that they can satisfy hydrogen bonding intramolecularly to improve cell permeability. Hydrogen bond donors are particularly problematic for cell permeability. A recent analysis of orally-available drugs and clinical candidates that are not 'rule of 5' compliant found that very few have 6 or greater hydrogen bond donors (HBD), while much greater allowances were found for other parameters, such as MW, polar surface area (PSA), hydrogen bond acceptors (HBA), and cLogP (Doak et al 2014). A similar result was found in the analysis of the AbbVie preclinical database (DeGoey et al 2017) and with recently approved orally available drugs (Shultz, 2019 J. Med. Chem.). Identification of SW2_110A as a selective and cell-permeable CBX8 ligand indicates that further improvements can still be made to increase "druglikeness" perhaps through further evaluation of bi-aromatic derivative structures or further minimization of the ligand and additional removal of amide bonds.

Further optimization of cell permeability will be essential for increasing the utility of chromodomain inhibitors for follow up biological studies. While there are many examples of canonical repressive functions for vertebrate PRC1, there are also examples of individual PRC1 subunits potentially acting in noncanonical roles. In particular, CBX8 has been implicated in transcriptional activation in development (Creppe et al., 2014) and disease (Tan et al 2011). Since these functions have been proposed to be independent of PRC1 (Béguelin et al., 2016, Tan et al 2011), they may or may not require the chromodomain. Previous studies have demonstrated the significance of HOX gene activations for MLL-AF9 leukemogenesis, and the requirement for CBX8 in HOX gene activation; however, the role for the CBX8 ChD in this process was still unknown. Using our cell permeable CBX8 inhibitors, we have determined that the CBX8 ChD is required for HOXA9 gene activation in MLL-AF9 leukemia, although the mechanism is still unresolved. In leukemia, MLL-AF9 binds to HOXA9 and the border of the H3K27me3 island is shifted (Bernt et al., 2011). Whether the CBX8 ChD is involved in a non-canonical protein-protein interaction with activators like Tip60 (Tan et al. 2011), or in canonical binding of H3K27me3 and recruiting MLL-AF9 at this boundary will be an intriguing avenue to explore using these cell permeable chromodomain inhibitors.

The Polycomb Group Chromobox proteins are attractive targets for drug development. Due to the high structure and sequence similarity of CBX ChD, along with the non-traditional binding pocket, development of selective and cell-permeable ligands remains challenging. Here, we have utilized DNA-encoded chemical libraries, rather than traditional high-throughput screening, for the successful identification and optimization of CBX8 ChD ligands. An optimal compound deactivated HOXA9 gene expression and demonstrated effectiveness in inhibiting THP1 cell growth, but did not display any cellular activity in K562 cells. Ligand validation and phenotypic analysis indicates that targeting the CBX8 ChD in MLL-AF9 translocated leukemia is an attractive strategy. This CBX8 ChD ligand is a useful biochemical tool to rapidly define other cancers and cell lines dependent on CBX8 ChD binding. In addition to defining the contribution of CBX8 to transcription and oncogenesis in cancers, the probe can be utilized to decipher CBX paralog-specific roles in chromatin regulation.

Translocations that involve the mixed lineage leukaemia (MLL) gene identify a unique group of acute leukaemias, and often predict a poor prognosis. They are found in >70% of infant leukemias and 10% of adult leukemias. MLL is a histone methyltransferase and the five most frequent translocations (>80% total) are members of the super elongation complex, which promotes gene transcription. The second and third most common partners (34% of MLL translocations), ENL and AF9 directly bind CBX8, and MLL-AF9 and MLL-ENL translocations require CBX8 for leukemia development and maintenance. Indeed, we find that leukemia growth (and HOXA9 transcription) with MLL-AF9 translocation is inhibited with CBX8 inhibitors, while leukemia with BCR-ABL translocations in not. Therefore CBX8 is a validated target for leukemias with MLL translocations with AF9 and ENL, which will likely extend to MLL tranlocations with other members of the super elongation complex.

Experimental Model and Subject Details
Cell Line Authentification.

Cell lines were obtained directly from ATCC or NIH AIDS reagent program and used at less than 15 passages.

KEY RESOURCES TABLE

| REAGENT or RESOURCE | SOURCE | IDENTIFIER |
|---|---|---|
| Antibodies | | |
| Rabbit polyclonal anti-CBX8 | Bethyl | Cat# A300-882A; RRID: AB_2071525 |
| Rabbit polyclonal anti-CBX7 | Bethyl | Cat# A302-525A; RRID: AB_1998945 |
| Mouse monoclonal anti-CBX6 | Santa Cruz | Cat# sc-86354; RRID: AB_2071496 |
| Rabbit polyclonal anti-CBX4 | Bethyl | Cat# A302-355A; RRID: AB_1907234 |
| Mouse monoclonal anti-CBX2 | Santa Cruz | Cat# sc-136387; RRID: AB_10840095 |
| Experimental Models: Cell lines | | |
| HEK 293T cells | ATCC | Cat# CRL-3216; RRID: CVCL_0063 |
| THP1 cells | ATCC | Cat# TIB-202; RRID: CVCL_0006 |
| K562 cells | ATCC | Cat# CCL-243; RRID: CVCL_0004 |
| Halo-GFP Hela cells | gift from Dr. | N/A |

KEY RESOURCES TABLE (continued)

| REAGENT or RESOURCE | SOURCE | IDENTIFIER |
|---|---|---|
| | Joshua A. Kritzer, Peraro et al., 2017 | |
| Chemicals, Peptides, and Recombinant Proteins | | |
| 5-/6-FAM NHS ester | ThermoFisher | 1.1 Cat# 46410; |
| Rink amide MBHA resin | Chem-Impex International | Cat# 14005; |
| Polystyrene-linked aldehyde resin | Sigma-Aldrich | Product# 516449; |
| Biotin-PEG3-azide | Click Chemistry Tools | Cat# AZ104-100; |
| FITC-labelled probe(For competitive FP assay) | Milosevich et al., 2016 | N/A |
| Fmoc-amino acid | Chem-Impex International (mainly) | N/A |
| Critical Commercial Assays | | |
| CellTiter-Glo ® | Promega | Cat# G7570 |
| Oligonucleotides | | |
| 40-mer ssDNA | IDT/Bioneer | N/A |
| Primers for qPCR and qRT-PCR | Thermo Scientific | N/A |

Cell Culture Conditions
HEK293T Cell Culture

Human female HEK293T cells were cultured in (DMEM (Gibco), 10% FBS (J R Scientific), 1% Sodium pyruvate (Invitrogen), 1% Pen/Strep(Invitrogen), 1% Glutamax (Thermo Scientific). After 72 h, the cells were split 1:4 with 0.25% Trypsin-EDTA (Gibco).

THP1 Cell Culture

Human THP1 cells were cultured in (RPMI (Gibco), 10% FBS (J R Scientific), 1% Sodium pyruvate (Invitrogen), 1% Pen/Strep(Invitrogen), 1% Glutamax (Thermo Scientific), 0.1% 2-mercaptoethanol. After 72 h, the cells were diluted to a concentration of 2×105 cells/mL with fresh media.

K562 Cell Culture

Human K562 cells were cultured in (RPMI (Gibco), 10% FBS (J R Scientific), 1% Sodium pyruvate (Invitrogen), 1% Pen/Strep(Invitrogen), 1% Glutamax (Thermo Scientific). After 72 h, the cells were diluted to a concentration of 2×105 cells/mL with fresh media.

Halo-GFP-Mito Hela Cell Culture

Cells were cultured in (DMEM (Gibco), 10% FBS (J R Scientific), 1% Sodium pyruvate (Invitrogen), 1% Pen/Strep (Invitrogen), 1% Glutamax (Thermo Scientific), 1 µg/mL puromycin). After 72 h, the cells were split 1:4 with 0.25% Trypsin-EDTA (Gibco).

Method Details

Materials and Methods

Oligonucleotides were purchased from IDT (Coralville, Iowa) or Bioneer (Alameda, Calif.) and used as provided. Analytical high-performance liquid chromatography (HPLC) separations were completed using an Agilent 1100 system with detection at 260 nm using a water/MeCN gradient containing 100 mM triethylammonium acetate, pH 5.5. Preparative HPLC separations were completed using a Varian ProStar system with detection at 260 and 280 nm using a water/MeOH gradient containing 0.75% hexafluoroisopropanol, 0.0035% triethylamine, pH 7.0. Reagents and solvents were used as received from commercial sources.

Preparation of 96 Single 140-Mer dsDNA Constructs

The integrated polymerase chain assembly (PCA)—PCR experiments were used to generate 96 single-gene barcode DNA constructs using a modified procedure (TerMaat et al.). For each reaction, six pairs of complementary 40-mer DNA oligonucleotides (previously described, Giaever et al.) were used. Six 40-mer oligos were pooled and used as templates for PCA. Each 5.0 µL PCA reaction contained 0.2 µM of each template 40-mer, with the following: 1.0 mM dNTPs, 0.1 U/µL of Vent DNA polymerase in 1×DNA polymerase buffer (NEB). All thermocycle procedures were as follows: 3 min at 94° C., then cycling for denaturation at 94° C. for 15 s, annealing at 58° C. for 15 s, extension at 72° C. for 30 s, and a final extension of 72° C. for 5 min after 20 cycles. Each 50 µL PCR reaction contained 5 µL of PCA product, 0.2 mM each dNTP, 0.4 µM of each end primer ($Z_A$ and $Z_D'$), and 0.025 U/µL DreamTaq DNA polymerase in 1×DreamTaq buffer (Thermo Fisher). The successive PCR went for 20 cycles using the same thermocycling conditions as PCA. Following PCR, each reaction was purified using SeraMag Carboxylate-Modified Magnetic SpeedBeads (GE Healthcare, Pittsburgh, PA) as previously reported (Jetson et al.) and quantified by UV absorbance at 260 nm.

CBX ChD Protein Expression and Purification

CBX chromodomain constructs (addgene plasmid #25158 (CBX2), #25237 (CBX4), #25296 (CBX6), #25241 (CBX7) and #62514 (CBX8, provided by Cheryl Arrowsmith), Kaustov et al.) were transformed into chemically competent BL21 CodonPlus RIL *E. coli* cells (Stratagene, La Jolla, Calif.) as N-terminal His6—tagged proteins. Bacterial growth was completed at 37° C. in LB media to OD600=2.0, followed by reducing the temperature to 16° C. over 30-60 min and induced with 1 mM IPTG for 16 h. Cells were collected by centrifugation at 6000 rpm for 20 min and resuspended in ChD binding buffer (20 mM Tris, pH 8, 150 mM NaCl, 0.01% Tween-20, 20 mM imidazole) with 1.0 mM PMSF. Bacteria pellets were stored at −80° C. until needed. Pellets were thawed on ice for 10 min in ChD binding buffer, and shaked at 4° C. supplemented with 100 µg/mL lysozyme, 1 mg/mL CHAPS and 1 mM PMSF, for 30 min. Cells were subsequently lysed by sonication (15 W, 30 s on, followed by 30 s off, twice, followed by 20 W for 1 min). The solubilized fraction was collected by centrifugation at 15000 rpm for 40 min at 4° C. Meanwhile, Ni-NTA Agarose resin (QIAGEN, Venlo, Netherlands) was washed with $H_2O$ and equilibrated with ChD binding buffer. The soluble fraction was incubated with the prewashed Ni-NTA agarose resin at 4° C. for 2 h. The resin was then washed 3× with ChD purification buffer (20 mM Tris, pH 8, 150 mM NaCl, 0.01% Tween-20, 1 mM PMSF). Proteins were eluted by the addition of 0.5 M imidazole to ChD purification buffer. The elution was diluted with 30% glycerol, flash frozen, and stored at −80° C. until needed. Protein purity was assessed by SDS-PAGE and concentration was determined by the Pierce 660 kit (Thermo Scientific).

Preparation of Kme3-Ser-CPF

The first two residues of the CBX consensus sequence were synthesized in bulk as previously described (Denton et al.). Briefly, 150 nmol of $NH_2$-5'-$CP_F$ in DEAE binding buffer (10 mM HOAc and 0.005% Triton X-100) was split between 6 cartridges. Each contained 220 µL 50% DEAE Sepharose slurry in 50% ethanol and was pre-washed with DEAE bind buffer. The DNA-loaded cartridges were washed 3×3 mL MeOH. Fmoc-amino acid coupling was achieved by incubating the cartridges in 1 mL of 50 mM Fmoc-amino acid, 50 mM EDC-HCl, and 5 mM HOAt in 40% DMF/60% MeOH for 30 minutes at RT, with double couplings. After couplings, the cartridges were washed 3×3 mL MeOH followed by 3×3 mL DMF. Fmoc deprotection was achieved by incubating the cartridges in 1 mL of 20% piperidine in DMF for 30 minutes at RT, then washed with 3×3 mL DMF, 3×3 mL MeOH, and 1 mL DEAE binding buffer after the final coupling. The DNA was eluted and collected by passing 1 mL of DEAE Elution Buffer (1.5 M NaCl and 0.005% Triton X-100) through each cartridge. The crude conjugate was desalted and concentrated to dryness.

Positional Scanning Library Synthesis.

The purified $Kme_3$-Ser-$CP_F$ conjugate was suspended in 4.8 mL DEAE binding buffer. To 96 wells in a 384-well filter plate, 20 µL DEAE Sepharose was added and washed 3×90 µL DEAE binding buffer. To each well, 50 µL of $Kme_3$-Ser-$CF_F$ solution (approximately 1 nmol conjugate per well) was added and washed 3×90 µL MeOH. Briefly, Fmoc-amino acids were coupled using 50 mM Fmoc-amino acid, 50 mM EDC-HCl, 5 mM HOAt in 40% DMF/60% MeOH for 30 minutes at RT with double coupling and deprotected by 20% piperidine in DMF for 30 minutes at RT. Wells were washed 3×90 µL MeOH and 3×90 µL DMF between each step. Following the final chemistry step, wells were washed 3×90 µL DMF, 3×90 µL MeOH, and 90 µL DEAE binding buffer. DNA-conjugates were eluted by incubating 2×40 µL DEAE Elution Buffer in each well for 5 minutes at RT and then collected by centrifugation. Each conjugate was then attached to a unique 140-mer dsDNA template sequence by PCR individually (1×DreamTaq Buffer, 0.5 µM $CF_F$-conjugate (PSL library member), 0.5 µM CPR, 0.2 mM dNTPs, 0.05 ng/µL template, and 0.025 U/µL). All PCRs were pooled and purified by SPRI and quantified by UV absorbance at 260 nm.

Positional Scanning Library Selection Against PcG CBX ChDs.

A frozen pellet from an induced 5 mL *E. coli* culture with CBX-$His_6$ ChD was suspended in 300 µL of ice-cold lysis buffer (20 mM Tris, pH 8, 150 mM NaCl, 100 µg/mL, 1 mg/mL CHAPS, 0.02% Tween-20, 1 mM PMSF) and lysed by sonication for 2 min (3 s on, 3 s off) at 30% power while on ice. The lysate was collected after centrifugation at 4000 g at 4° C. Meanwhile, 21 µL of His Mag Sepharose Ni (Ni-NTASepharose-MBs) were pre-washed with 3×21 µL of purification buffer (20 mM Tris, pH 8.0, 150 mM NaCl, 20 mM imidazole, 1 mM PMSF, 0.02% Tween-20). The soluble lysate was then combined with 12 µL of pre-washed Ni-NTA-Sepharose-MBs and incubated at 4° C. for 1 h. The MBs were separated and washed in 5×11 µL of purification buffer. After the last wash, the MBs were suspended in 12 µL of purification buffer. The CBX-bound MBs were split and diluted to yield 10 µL of 1×(~50 µM CBX), 10 µL of ⅒× (~5 µM CBX), and 10 µL of ½₀× (~2.5 µM CBX). The MBs were separated and 10 µL of the DNA pre-mix (50 nM Bz-Za-d on DNA construct 97 (nonligand), 0.5 nM 4-BrBA-F-A-I-Kme3-S-Za-d on DNA construct 98 (high-affinity ligand), and 50 nM CBX positional scanning library-DNA conjugates (approximately 0.5 nM of each library member) in 20 mM Tris, pH 8, 150 mM NaCl, 10 mM MgCl2, 0.02% Tween-20, 1 mg/mL BSA, 1 mg/mL sheared salmon sperm DNA) was added to all four samples (mock [no protein/MBs only], 50 µM CBX, 5 µM CBX, and 2.5 µM CBX) and allowed to incubate at RT for 1 h. The MBs were then separated and washed 5× in 10 µL of the above buffer. DNA conjugates and protein were eluted by incubating the MBs for 5 min at RT in the above buffer with 0.5 M imidazole. Each elution was collected and prepared for PCR and next-generation sequencing (NGS). The above procedure was applied to selections against all PcG CBX paralog.

Solid Phase Peptide Synthesis (SPPS).

Off-DNA peptides were prepared using traditional SPPS methods. All couplings and deprotections were monitored by ninhydrin tests. Briefly, 50 mg of Rink Amide MBHA resin was swelled for 20 minutes in 1,2-dichloroethane and 20 minutes in DMF before suspension in 20% piperidine in DMF for the initial Fmoc deprotection for 30 minutes at RT. Couplings were completed using 5.0 eq. (relative to the capacity of the resin) of Fmoc-AA (or carboxylic acid), 5.0 eq. HOAt, and 5.0 eq. DIC in DMF (approximately 0.1 M) and pre-activated for 20 minutes at RT before being added to the resin. Fmoc deprotections were achieved by incubating the resin for 30 minutes at RT in 20% piperidine in DMF. Peptides were cleaved and deprotected by incubating in 95% TFA, 2.5% triisopropylsilane, and 2.5% $H_2O$ for 3 hours at RT. The crude peptide was collected by precipitation out of ice-cold diethyl ether and then suspended in 50% MeOH/50% $H_2O$ and concentrated to dryness. The residue was dissolved in DMSO and purified on a semi-prep HPLC using a $H_2O$/MeOH+0.1% TFA gradient with detection at 215 nm and 254 nm. Yield was determined by mass of the dried, purified peptide as the TFA salt relative to the equivalents as determined by the mass of resin used. Purity was confirmed to be >95% by HPLC.

Synthesis of Diethyllysine Derivatives

Crude peptides were synthesized as described above. After purification of the peptide, reductive amination was accomplished via dissolvation of peptides in 80% MeOH and 20% DMSO, followed with 100 eq. acetaldehyde and 50 eq. $NaCNBH_3$ (final peptide conc. 0.1M) and incubated at 37° C. overnight. The mixture was concentrated and HPLC purified as described above.

Synthesis of C-Terminal Alkyne Peptide

Modified methods from previously reported procedure (Ten Brink et al.) were used to synthesize C-terminal alkyne peptides. Polystyrene-linked aldehyde resin (FMPB AM resin, 100 mg, 1.08 mmol/g) was added to a round bottom flask and gently stirred for 30 minutes at RT in DCM. DCM was gently evaporated and 5 mL of DMF with 5 mL of MeOH was added to the resin. To this, 10 eq. glacial AcOH was added with 10 eq. propargyl amine and 10 eq. $NaCNBH_3$ and gently stirred under light reflux for 3 hours at 80° C. The mixture was cooled and washed with MeOH, DCM, and DMF and re-swelled for 30 mins in 1,2-dichloroethane prior to the first acylation. To the resin, 5.0 eq. Fmoc-Ser(OtBu)—OH with 5.0 eq. DIC, 8.0 eq. HOAt in DMF was added and incubated at 37° C. overnight. The remaining synthesis, purification, and reductive amination were completed as described above. Purity was confirmed to be >95% by HPLC.

Synthesis of 5-/6-FAM.

To 10.0 mg of 5-/6-FAM NHS ester (ThermoFisher), 422 µL of THF was added. Once dissolved, 7.2 mg (3.0 eq.) of 4-azido-1-aminobutane was added and mixed vigorously. A precipitate initially formed but dissolved upon mixing and then the reaction was incubated at RT, protected from light, and incubated at RT for 16 hours. The reaction was then concentrated and purified by semi-prep HPLC with $H_2O$/MeOH 0.1% TFA gradient.

Synthesis of FAM-Peptide Conjugate.

To a 150 µL of 100 mM alkyne peptides in DMSO, 13.1 mg of a single isomer of 4-Azido-5/6-FAM (0.5 eq.) was added. To this, 5.0 µL of 2 M TEAA, pH 5.5, and 10 µL 0.1 M aminoguanidinium-HCl was added. Separately, 25 µL of CuBr-saturated DMSO was suspended in 50 µL of 50 mM THPTA and then added to the azide/alkyne mixture. The mixture was incubated at RT overnight and then 10 µL of 0.5 M EDTA, pH 8 was added to the mixture. The FAM-peptide conjugate was purified as described above. Purity was confirmed to be >95% by HPLC.

Synthesis of Biotin-Peptide Conjugate

To a 150 µL of 100 mM alkyne peptides in DMSO, 13.1 mg of Biotin-PEG3-azide (2.0 eq.) was added. To this, 5.0 µL of 2 M TEAA, pH 5.5, and 10 µL 0.1 M aminoguanidinium-HCl was added. Separately, 25 µL of CuBr saturated DMSO was suspended in 50 µL of 50 mM THPTA and then added to the azide/alkyne mixture. The mixture was incubated at RT for overnight and then 10 µL of 0.5M EDTA, pH 8 was added. The peptide-biotin conjugate was purified as described above. Purity was confirmed to be >95% by HPLC.

Synthesis of Chloroalkane Linker 2-(2-azidoethoxy)ethanol was prepared as described with minor modifications (Ji et al., 2018). 2 g (2 mmol) of 2-(2-chloroethoxy)ethanol was dissolved in 20 mL of water and 3.6 g (48 mmol) of sodium azide was added. The solution was refluxed for 48 hours. The solution was then extracted 4 times with 20 mL DCM. The aqueous layer was saturated with NaCl and extracted another time with 20 mL DCM. Pooled organic fractions were dried over $Na_2SO_4$ and concentrated. Solvent was evaporated to yield 1.82 g (13.9 mmol) of azido product, which was used directly without further purification. 1 g (7.6 mmol) of 2-(2-azidoethoxy) ethanol was dissolved in 40 mL of dry THF and stirred under argon with 1 g (9.1 mmol) of potassium tert-butoxide for 20 minutes. 1-chloro-6-iodohexane (2.24 g (9.1 mmol)) was dissolved in THF and added dropwise to the stirring alkoxide to generate a milky white suspension. This was allowed to stir at RT overnight. The slurry was filtered, and the filtrate was reduced to a thick oil. The product was purified on 40 g of silica prepared initially in hexanes. The product was eluted with 85/15 hexanes/ethyl acetate to give 642 mg (2.58 mmol) product.

Competitive Fluorescence Polarization (FP) Assay of PSL Hits Against CBX6 ChD, CBX7 ChD and CBX8 ChD.

FP was measured by titration of CBX ChDs to a FITC-labelled probe as previously reported (Simhadri et al.). Binding and competition FP assays were performed in black 384-well plates with optical bottoms. The protein concentrations used were selected based on the reported relative affinity of the CBX ChD protein for the FITC probes. The FITC-labeled probe was kept constant at 100 nM with 1 µM CBX6, 0.4 µM CBX7 or 4 µM CBX8 with varying amounts of peptide by 2-fold series dilutions, from 500 µM as highest peptide concentration to 0.488 µM as the lowest. Assays were performed for each peptide in four replicates. Raw data were analyzed using GraphPad Prism 7 following a "one site-Fit log IC50" competition model with any outliers (95% confidence) being excluded.

Direct Fluorescence Polarization (FP) Binding Assay of PSL Hits Against PcG CBX ChDs.

FP assays were conducted as above with slight modifications. Alkyne peptides described above were conjugated with a fluorescein group (5-/6-FAM) through copper catalyzed click reaction as previously described. The FAM-labeled peptide was kept constant at 100 nM. The CBX ChD proteins were titrated by 2-fold series dilutions in the assays. The highest protein concentrations, at which FAM-peptide was completely bound, used for each CBX in the direct binding assays depends on the binding affinity of the peptides. Assays were performed for each peptide in four replicates. Raw data were analyzed for determinations of Kd, using GraphPad Prism 7 following a "one-site" total binding model with any outliers (95% confidence interval) being excluded.

NMR Analysis of SW2_110A Binding.

The CBX8 CD construct was a gift to the lab from Cheryl Arrowsmith (Addgene plasmid #62514). GST-tagged CBX8 CD was created using Infusion and the pGSTag vector, given to the lab by Gerald Crabtree. The CBX8 CD were expressed in BL21 (DE3) pLysS *E. coli* cells. Cells were grown in LB media at 37° C. to an A600 OD of ~1.0. Cells were pelleted using centrifugation at 4,000 rpm and 18° C. for 10 minutes. Cells were then resuspended in M9 minimal media (4L LB cells per 1L M9) supplemented with $^{15}$N—NH$_4$Cl. Cells were alled to recover at 18° C. and 210 rpm for up to one hour before induction with 1 mM IPTG for 16-18 hours. Cells were pelleted via centrifugation at 6,000 rpm and 18° C. for 20 minutes. Cells were resuspended in 40 mL Low Salt Buffer (25 mM Tris-HCl, 50 mM NaCl) with DNase I and a protease inhibitor tablet. Resuspended pellets were lysed using the Emulsiflex. Cell lysate was cleared at 15,000 rpm and 4° C. for one hour.[10]

$^{15}$N-CBX8 CD was purified according to the following protocol. Clarified cell lysate containing GST-tagged $^{15}$N-CBX8 CD was rocked with glutathione agarose resin for one hour at 4° C. GST-tagged $^{15}$N-CBX8 CD bound beads were purified using a gravity flow column. Bound beads were rinsed thoroughly with High Salt Buffer (25 mM Tris-HCl, 1 M NaCl), followed by Low Salt Buffer. GST-tagged $^{15}$N-CBX8 CD was eluted from the beads using 50 mM glutathione in Low Salt Buffer, adjusted to a pH of 7.5. GST-tagged CBX8 CD was concentrated to a volume of 2 mL using a 10,000 MWCO filter. The GST-tag was cleaved using TEV protease at room temperature (25° C.) for three hours. The cleaved $^{15}$N-CBX8 CD was then purified using cation exchange chromatography and size exclusion (Superdex S75, 300/10). All $^{15}$N-CBX8 CD samples were moved into NMR Buffer (40 mM NaPi and 100 mM NaCl at pH 6.8) during size exclusion.

SDS-PAGE was used to confirm the identity and purity of $^{15}$N-CBX8 CD samples. Quantification of $^{15}$N-CBX8 CD was performed using the calculated extinction coefficient ($\varepsilon$=19,480 M$^{-1}$ cm$^{-1}$) and measured A280 value. All $^{15}$N-CBX8 CD samples were concentrated to 25-50 µM for NMR and flash frozen in liquid nitrogen for long-term storage at −80° C. Prior to collecting HSQC data, $^{15}$N-CBX8 CD samples were thawed overnight at 4° C.

$^{15}$N-HSQC spectra were collected on 25-50 µM $^{15}$N-CBX8 CD at 25° C. on a Bruker Avance II 800 MHz spectrometer equipped with a cryogenic probe. Titration with DMSO was performed by subsequently adding 1%, 2%, and 5% (v/v %) DMSO. Titration with SW2_110A was performed by addition of 0.5 (1% DMSO), 1.0 (2% DMSO), 2.5 (5% DMSO) or 11 (6% DMSO) molar ratios of. All spectra were processed using NMRPipe and ccpNmr.

Normalized chemical shift perturbation values (Δδ) were calculated for the DMSO and SW2_110A in Excel using the following equation:

$$\Delta\delta = \sqrt{(\Delta\delta_H)^2 + (0.2\Delta\delta_N)^2}$$

where Δδ is the chemical shift perturbation in in parts per million (ppm). Δδ values were considered significant when greater than the average plus one standard deviation, not including the highest 10% of CSP values or missing peaks.

Cell Proliferation Assays

THP1(MLL-AF9-induced leukemia cell line) cells were seeded at 0.1×10$^6$ cells/mL in 24-well flat bottom cell culture plate (#353047, Corning). Peptides SW2_110A and SW2_104A (100 µM) were added to the cells. Cells were grown for 72 h before trypsinized and counted. Cell suspension was homogenized by gentle pipetting and counted using Countess II (#AMQAF1000, Life Technologies). The media was then exchanged with fresh media containing DMSO, SW2_110A or SW2_104A. At day 6, 25 percent of cells in each well were split and transferred to new wells to avoid over-confluency, and media was replaced with fresh compounds in new media. The cell viability assay was extended to 12 days, with cell counting and fresh compound replenishment at day 3, 6, 9. Same procedures was applied for K562 cells, as control cell line (non-MLL-AF9-induced leukemia cell line).

CellTiter-Glo Luminescent Dose-Dependent Cell Viability Assay

The effect of SW2_110A and SW2_104A on cell viability was determined using a CellTiter-Glo ATP detection system (#G7573, Promega) THP1 cells were seeded in 0.1×10$^6$ cells/mL density in 96-well clear bottom white microplate (#655098, Greiner Bio-One). Cells were treated with compounds SW2_110A and SW2_104A for 12 days, with fresh compounds replenishment at day 3, 6, 9. For dose-response studies, IC$_{50}$ was derived from a eight-point 2-fold titration ranging from 100 µM to 1.56 µM of SW2_110A or SW2_104A. CellTiter-Glo reagent was added to cells, and incubated with gentle shake for 15 minutes in dim light at R.T. Luminescence was read on an GloMax® microplate reader. Luminescence was normalized to DMSO-treated groups. The IC$_{50}$ was calculated using the "log[inhibitor] vs. the normalized response-variable slope" equation in GraphPad Prism 7.

Sequential Salt Extraction 2.5×10$^6$ 293T cells were seeded in 10 cm cell culture dish (#353003, Corning) overnight. Next day, media was removed and cells were washed with PBS. Then, cells were pretreated with peptides SW2_110A or DMSO on plate (100 µM, 1% DMSO) in 3 mL media for 4 hours in 37° C. After the 4-hour pretreatment, media was removed and cells were washed again with PBS. Cells were harvested and washed with PBS. (Note: it is critical to balance the cell numbers the same in the peptide treated group and the DMSO treated control group.) Cells were resuspended in 1 mL Buffer A (25 mM HEPES, 25 mM KCl, 5 mM MgCl$_2$, 0.1% NP-40, 10% Glycerol, 0.05 M EDTA, pH 7.8, plus protease inhibitor) was added to the cell pellet from centrifuge and rotated at 4° C. for 10 minutes (Porter et al.). Cells were spun down at 6500×g for 5 min at 4° C. Supernatant was removed and cell pellet was resuspended with 500 µL of mRIPA (Modified Radioimmunoprecipitation Assay) Buffer (50 mM Tris, 1% Nonidet P-40, 0.25% Sodium deoxycholate, plus protease inhibitors). by pipetting up and down 15 times and incubated on ice for 5 minutes. (Note: it is critical to maintain the consistence for all washing steps with the subsequent NaCl containing mRIPA buffers) Then the sample was centrifuged for 3 min at 6500×g. The supernatant was saved in a separate tube, labeled as "0 mM fraction"—0 mM sequential salt extraction washing supernatant. (Notes: DMSO or the peptide SW2_110A was also added to the mRIPA washing buffers, in order to maintain the peptide in binding to the protein through the assay) The pellet was sequentially resuspended in 500 µl of mRIPA Buffer with increasing NaCl concentrations (100, 200, 300, 400, 500 mM). The procedures for 0 mM was repeated for each salt concentrations in the subsequent washes. All washing supernatants were saved and labeled. 4×Bolt LDS Sample Buffer (Invitrogen) with 10% β-mercaptoethanol (AMRESCO LLC, Solon, Ohio)

was added to each sample, and 50 µl of each fraction was loaded onto a 4-12% gradient gel (Invitrogen) for immunoblotting analysis of the proteins of interest. ImageJ was employed to quantitate the protein bands.

Peptide Pulldown Assay $2\times10^7$ HEK293T cells were seeded in a 15 cm cell culture dish overnight. Next day, media was removed and cells were washed with PBS. Cells were lysed with 5 ml Buffer A (25 mM HEPES, 5 mM KCl, 25 mM MgCl2, 0.05 mM EDTA, 10% glycerol, 0.1% NP-40, plus protease inhibitors) on ice for 15 minutes. The nuclei were pelleted and re-suspended in IP buffer (25 mM Tris, 300 mM NaCl, 1 mM EDTA, 1% NP-40, plus protease inhibitors) for 15 minutes. The sample were spun down at 15,000 rpm at 4° C. for 5 min and lysates were transferred to separate tubes. Protein concentrations were determined by Pierce 660 nm kit (Thermo Scientific). Streptavidin M-270 Dynabeads (Solulink, San Diego, Calif.) was washed three times with Pulldown Binding Buffer (50 mM Tris, 150 mM NaCl, 0.5 mM DTT). 10× of biotinylated peptides SW2_110A-B, as well as biotinylated H3K27me3 (21-44) and biotinylated H3 (21-44), were incubated with 50 µl pre-equilibriumed beads at 4° C. for an hour. After biotin-peptide being immobilized on resin, extra unbound peptides were removed by 3×washing, and 200 µg of nuclear lysate supernatant was added to each washed and immobilized biotinylated peptide (biotin-H3, biotin-H3K27me3, SW2_110A-B). The mixture was rotated at 4° C. for 2 hours. Then, the depleted lysate was removed and the beads were washed with Pulldown Binding Buffer 3× at 4° C. The beads were re-suspended with 30 µl Pulldown Binding Buffer. 10% of the lysate supernatant was used as input. 4×Bolt LDS Sample Buffer (Invitrogen) with 10% β-mercaptoethanol (AMRESCO LLC, Solon, Ohio) was added to each sample, and each fraction was heated at 95° C. for 5 min and loaded onto a 4-12% gradient gel (Invitrogen) for immunoblotting analysis of the proteins of interest. ImageJ was employed to quantitate the protein bands.

Chromatin Immunoprecipitation-qPCR (ChIP-qPCR)

ChIP: Hs68 cells were seeded at $4\times10^6$ in a 10 cm cell culture plates 16 hours prior to treatment. Cells were treated with 100 µM SW2-110A or DMSO for four hours. ChIP was performed as described in Connelly et al., 2018. Briefly, cells were washed with PBS and fixed on the plate with CiA Fix buffer (50 mM HEPES, pH 8.0, 1 mM EDTA, 0.5 mM ETGA, 100 mM NaCl) and 1% formaldehyde for 10 min at room temperature. Crosslinking was quenched with 0.125 M glycine for 5 min at 4° C. Cells were washed once with PBS and lifted off the plate then resuspended in CiA NP Rinse buffer 1 (50 mM HEPES pH 8.0, 140 mM NaCl, 1 mM EDTA, 10% glycerol, 0.5% NP-40, 0.25% Triton X) for 10 min. Cells were pelleted at 1200×g for 5 min at 4° C. The supernatant was removed, and the cells were resuspended in CiA NP rinse buffer 2 (10 mM Tris pH 8.0, 1 mM EDTA, 0.5 mM EGTA, 200 mM NaCl). Cells were collected by centrifugation, 1200×g for 5 min. Supernatant was removed and the cells were washed twice with shearing buffer (0.1% SDS, 1 mM EDTA, 10 mM Tris HCl, pH 8.0). Cells were resuspended in shearing buffer and sonicated for 7 min with the probe (Branson). Lysate was centrifuged at 21,000×g for 15 min to remove debris. Supernatant was collected and pre-cleared overnight with Protein A/G magnetic beads (Pierce). For immunoprecipitation, pre-cleared cell lysate was divided in thirds and incubated with 1 µg of antibody and Protein A/G magnetic beads for 3 hrs. Ten percent (10%) input was saved. The IPs were washed 2 times for 3 min at RT with IP buffer (50 mM HEPES/KOH pH 7.5, 300 mM NaCl, 1 mM EDTA, 1% Triton X, 0.1% DOC, 0.1% SDS) followed by a DOC (10 mM Tris pH 8.0, 0.25M LiCl, 0.5% NP-40, 0.5% DOC, 1 mM EDTA) wash and a 1×TE wash. Protein was eluted from beads (1% SDS, 0.1 M NaHCO3) twice for 20 minutes at RT. Samples, including input, were treated with RNase A at 37° C. for 30 min followed by proteinase K for 3 hours at 55° C. Samples were uncrosslinked overnight at 65° C. Phenol chloroform extraction followed by isopropanol precipitation were used to isolate the DNA. DNA was resuspended in 20 µL TE for qPCR analysis. Antibodies used for IP were CBX8 (Bethyl, rabbit), IgG (CST, rabbit), CBX7 (Bethyl, rabbit).

qPCR: qPCR was performed on the isolated ChIP DNA using SYBR master mix (Thermo) and run on the BioRad CFX thermo cycler. Three biological replicates were performed in technical triplicate. Enrichment was determined by percent input. The Forward and Reverse primers used Table 3 below and are listed in the article Sijie Wang, et al., "Optimization of Ligands Using Focused DNA-Encoded Libraries To Develop a Selective, Cell-Permeable CBX8 Chromodomain Inhibitor," *ACS Chem. Biol.* 2020, 15, 112-131. DOI: 10.1021/acschembio.9b00654 (including all Supplemental Materials related thereto, the "Wang et al. Article"), the entirety of which is incorporated herein by reference.

TABLE 3

Primer sequences used in qPCR

| Gene name | Forward primer (5'-3') | Reverse primer (5'-3') |
|---|---|---|
| LMNB2 | CCGAATCTCTGAAAT GAAAGTCCATGC (SEQ ID NO: 14) | TTAAAGATCTGAGGG ACTCCTCAGTC (SEQ ID NO: 15) |
| CCND2 (Pemberton et al) | ACTGTCTGAAATGAA GGTGAAGC (SEQ ID NO: 16) | GATTTGATGGACACT TGGTTTGT (SEQ ID NO: 17) |
| GATA6 (Pemberton et al) | GCCTCTCCATTCCAG AGTTTT (SEQ ID NO: 18) | TCCAGAAACCGTTCT CATCC (SEQ ID NO: 19) |
| RUNX3 (Pemberton et al) | TCAAAAGGCATCCGC CTCTCCGT (SEQ ID NO: 20) | AAGGATGCACCTGCC GGGAATTG (SEQ ID NO: 21) |

Quantitative Reverse Transcriptase Polymerase Chain Reaction (qRT-PCR)

$1\times10^6$ THP1 and K562 cells were treated with SW2_110A at 100 µM or DMSO (1%) for 72 h. Cells were harvested after 72 h for RNA extraction. After homogenization of THP1 or K562 cells using TRIzol reagent (Thermo Scientific), RNA was extracted from the aqueous phase in the phase separation step. RNA pellet was washed with 75% ethanol and concentrated for subsequent reverse transcription. 2 µg RNA was then converted into cDNA using Verso cDNA synthesis kit (Thermo Scientific). SYBR Green Mastermix (Thermo Scientific) was used for quantitative PCR. Primers for human HOXA9 gene and B2M gene as control are used in the qPCR.

| Gene name | Forward primer (5'-3') | Reverse primer (5'-3') |
|---|---|---|
| HOXA9 (Tan et al.) | GGCCCAGGACCGAGA TACTT (SEQ ID NO: 22) | CGCTCACGGACAATC TAGTTGT (SEQ ID NO: 23) |

| Gene name | Forward primer (5'-3') | Reverse primer (5'-3') |
|---|---|---|
| B2M | TGCTGTCTCCATGTT TGATGTATCT (SEQ ID NO: 24) | TCTCTGCTCCCCACC TCTAAGT (SEQ ID NO: 25) |

Chloroalkane Penetration Assay (CAPA)

CAPA is a recently developed cell penetration assay for measuring relative cytosolic access without interference from endosomally trapped peptides (Peraro et al. 2017). Halo-GFP-Mito Hela cells were cultured and seeded at a $1 \times 10^5$ cells/well in a 24- or 48-well plate the day before experiments. Cells were rinsed by PBS and treated with chloroalkane conjugated CBX8 peptidomimetic ligands SW2_110A-CA or KED97L-CA in acidified Opti-MEM (0.15% 6N HCl) for 4 h. Next, media was removed and cells were washed by phenol red-free Opti-MEM for 30 minutes, followed by incubation with 5 µM HT-TAMRA (HTag-TMR, Promega) for another 30 minutes. Then, cells were washed for 15 minutes by phenol red-free DMEM +10% FBS +1% pen/strep, followed with PBS wash and trypsin incubation. Cells were transferred to a new microcentrifuge tube and pelleted by centrifuge, with two times of PBS washes. Cell pellets were resuspended in 250 µL PBS, and 200 µL was used for flow cytometry analysis. Live cells will be gated and 10000 cells were measured per sample. Mean fluorescence intensity was calculated from raw data, and these values were normalized to the samples with no dye (0% red signal) and with dye but no HT-molecule (100% red signal).

QUANTIFICATION AND STATISTICAL ANALYSIS. Statistical details can be found in the Figure legends. Bar graphs are plotted as mean±S.D. Statistical significance was calculated using Prism 7. Asterisks indicate the level of significance using student's T test (* $p<0.05$  $p<0.01$, * $p<0.001$, **** $p<0.0001$).

Those skilled in the art will recognize that numerous modifications can be made to the specific implementations described above. The implementations should not be limited to the particular limitations described. Other implementations may be possible.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES

1. Ayton, P. M., and Cleary, M. L. (2003). Transformation of myeloid progenitors by MLL oncoproteins is dependent on Hoxa7 and Hoxa9. Genes Dev. 17, 2298-2307.
2. Bernt, K. M., Zhu, N., Sinha, A. U., Vempati, S., Faber, J., Krivtsov, A. V., Feng, Z., Punt, N., Daigle, A., Bullinger, L. and Pollock, R. M., 2011. MLL-rearranged leukemia is dependent on aberrant H3K79 methylation by DOT1L. Cancer cell, 20(1), pp. 66-78.
3. Béguelin, W., Teater, M., Gearhart, M. D., Calvo Fernández, M. T., Goldstein, R. L., Cardenas, M. G., . . . Melnick, A. M. (2016). EZH2 and BCL6 Cooperate to Assemble CBX8-BCOR Complex to Repress Bivalent Promoters, Mediate Germinal Center Formation and Lymphomagenesis. Cancer Cell, 30(2), 197-213.
4. Chou, R. H., Yu, Y. L., & Hung, M. C. (2011). The roles of EZH2 in cell lineage commitment. American Journal of Translational Research, 3(3), 243-250.
5. Chung, C. Y., Sun, Z., Mullokandov, G., Bosch, A., Qadeer, Z. A., Cihan, E., . . . Bernstein, E. (2016). Cbx8 Acts Non-canonically with Wdr5 to Promote Mammary Tumorigenesis. Cell Reports, 16(2), 472-486.
6. Connelly, K. E., & Dykhuizen, E. C. (2017). Compositional and functional diversity of canonical PRC1 complexes in mammals. Biochimica et Biophysica Acta— Gene Regulatory Mechanisms, 1860(2), 233-245.
7. Connelly, K. E., Weaver, T. M., Alpsoy, A., Gu, B. X., Musselman, C. A. and Dykhuizen, E. C., 2018. Engagement of DNA and H3K27me3 by the CBX8 chromodomain drives chromatin association. Nucleic acids research.
8. Creppe, Catherine, et al. "A Cbx8-containing polycomb complex facilitates the transition to gene activation during ES cell differentiation." PLoS genetics 10.12 (2014): e1004851.
9. Denton, K. E., Wang, S., Gignac, M. C., Milosevich, N., Hof, F., Dykhuizen, E. C., & Krusemark, C. J. (2018). Robustness of In Vitro Selection Assays of DNA-Encoded Peptidomimetic Ligands to CBX7 and CBX8. SLAS Discovery, 23(5), 417-428.
10. Franzini, Raphael M, Dario Neri, and Jorg Scheuermann. 2014. "DNA-Encoded Chemical Libraries: Advancing Beyond Conventional Small-Molecule Libraries." Accounts of Chemical Research 47 (4): 1247-55.
11. Goodnow Jr, Robert A., Christoph E. Dumelin, and Anthony D. Keefe. "DNA-encoded chemistry: enabling the deeper sampling of chemical space." Nature Reviews Drug Discovery 16.2 (2017): 131.
12. J. A. Kennison, The Polycomb and Trithorax group proteins of Drosophila: trans-regulators of homeotic gene function, Annu. Rev. Genet. 29 (1995) 289-303
13. Kaustov, L., Ouyang, H., Amaya, M., Lemak, A., Nady, N., Duan, S., . . . Arrowsmith, C. H. (2011). Recognition and specificity determinants of the human Cbx chromodomains. Journal of Biological Chemistry, 286(1), 521-529.
14. Klauke, K., Radulović, V., Broekhuis, M., Weersing, E., Zwart, E., Olthof, S., . . . De Haan, G(2013). Polycomb Cbx family members mediate the balance between haematopoietic stem cell self-renewal and differentiation. Nature Cell Biology, 15(4), 353-362.
15. Kim, K. H., & Roberts, C. W. M. (2016). Targeting EZH2 in cancer. Nature Medicine, 22(2), 128-134.
16. Koppens, M., & Van Lohuizen, M. (2016). Context-dependent actions of Polycomb repressors in cancer. Oncogene, 35(11), 1341-1352.
17. Krusemark, Casey J., et al. "Directed chemical evolution with an outsized genetic code." PloS one 11.8 (2016): e0154765.
18. Kumar, A. R., Hudson, W. A., Chen, W., Nishiuchi, R., Yao, Q., and Kersey, J. H. (2004). Hoxa9 influences the phenotype but not the incidence of Mll-AF9 fusion gene leukemia. Blood 103, 1823-1828.
19. Li, Gang, et al. "Altered expression of polycomb group genes in glioblastoma multiforme." PloS one 8.11 (2013): e80970.
20. Marian, C. A., Stoszko, M., Wang, L., Leighty, M. W., de Crignis, E., Maschinot, C. A., Gatchalian, J., Carter, B. C., Chowdhury, B., Hargreaves, D. C. and Duvall, J. R., 2018. Small molecule targeting of specific BAF (mSWI/

SNF) complexes for HIV latency reversal. *Cell chemical biology,* 25(12), pp. 1443-1455
21. Milosevich N, Hof F. Chemical inhibitors of epigenetic methyllysine reader proteins[J]. Biochemistry, 2015, 55(11): 1570-1583.
22. Milosevich, N., Gignac, M. C., McFarlane, J., Simhadri, C., Horvath, S., Daze, K. D., . . . Hof, F. (2016). Selective Inhibition of CBX6: A Methyllysine Reader Protein in the Polycomb Family. *ACS Medicinal Chemistry Letters,* 7(2), 139-144.
23. Mills, A. A. (2010). Throwing the cancer switch: Reciprocal roles of polycomb and trithorax proteins. *Nature Reviews Cancer,* 10(10), 669-682.
24. Monroe, S. C., Jo, S. Y., Sanders, D. S., Basrur, V., Elenitoba-Johnson, K. S., Slany, R. K., and Hess, J. L. (2011). MLL-AF9 and MLL-ENL alter the dynamic association of transcriptional regulators with genes critical for leukemia. *Exp Hematol.* 39, 77-86.
25. Morey, L., Pascual, G., Cozzuto, L., Roma, G., Wutz, A., Benitah, S. A. and Di Croce, L., 2012. Nonoverlapping functions of the Polycomb group Cbx family of proteins in embryonic stem cells. *Cell stem cell,* 10(1), pp. 47-62.
26. Mueller, D., Bach, C., Zeisig, D., Garcia-Cuellar, M. P., Monroe, S., Sreekumar, A., Zhou, R., Nesvizhskii, A., Chinnaiyan, A., Hess, J. L., and Slany, R. K. (2007). A role for the MLL fusion partner ENL in transcriptional elongation and chromatin modification. *Blood* 110, 4445-4454.
27. Ren, C., Morohashi, K., Plotnikov, A. N., Jakoncic, J., Smith, S. G., Li, J., . . . Zhou, M. M. (2015). Small-molecule modulators of methyl-lysine binding for the CBX7 chromodomain. *Chemistry and Biology,* 22(2), 161-168.
28. Ren, C., Smith, S. G., Yap, K., Li, S., Li, J., Mezei, M., . . . Zhou, M. M. (2016). Structure-Guided Discovery of Selective Antagonists for the Chromodomain of Polycomb Repressive Protein CBX7. *ACS Medicinal Chemistry Letters,* 7(6), 601-605.
29. Satz, Alexander L. "DNA encoded library selections and insights provided by computational simulations." *ACS chemical biology* 10.10 (2015): 2237-2245.
30. Satz, Alexander L. "Simulated screens of DNA encoded libraries: the potential influence of chemical synthesis fidelity on interpretation of structure-activity relationships." *ACS combinatorial science* 18.7 (2016): 415-424.
31. Sauvageau, M., & Sauvageau, G. (2010). Polycomb group proteins: Multi-faceted regulators of somatic stem cells and cancer. *Cell Stem Cell,* 7(3), 299-313.
32. Santiago, C, K Nguyen, and M Schapira. 2011. "Druggability of Methyl-Lysine Binding Sites." Journal of Computer-Aided Molecular Design 25 (12): 1171-78.
33. Simhadri, C., Daze, K. D., Douglas, S. F., Quon, T. T. H., Dev, A., Gignac, M. C., . . . Hof, F. (2014). Chromodomain antagonists that target the polycomb-group methyllysine reader protein chromobox homolog 7 (CBX7). *Journal of Medicinal Chemistry,* 57(7), 2874-2883.
34. Stuckey, J. I., Dickson, B. M., Cheng, N., Liu, Y., Norris, J. L., Cholensky, S. H., . . . Frye, S. V. (2016). A cellular chemical probe targeting the chromodomains of Polycomb repressive complex 1. *Nature Chemical Biology,* 12(3), 180-187.
35. Stuckey, J. I., Simpson, C., Norris-Drouin, J. L., Cholensky, S. H., Lee, J., Pasca, R., . . . James, L. I. (2016). Structure-Activity Relationships and Kinetic Studies of Peptidic Antagonists of CBX Chromodomains. *Journal of Medicinal Chemistry,* 59(19), 8913-8923.
36. Tan, J., Jones, M., Koseki, H., Nakayama, M., Muntean, A. G., Maillard, I., & Hess, J. L. (2011). CBX8, a Polycomb Group Protein, Is Essential for MLL-AF9-Induced Leukemogenesis. *Cancer Cell,* 20(5), 563-575.
37. Zhang, C. Z., Chen, S. L., Wang, C. H., He, Y. F., Yang, X., Xie, D., & Yun, J. P. (2018). CBX8 exhibits oncogenic activity via AKT/b-catenin activation in hepatocellular carcinoma. *Cancer Research,* 78(1), 51-63.

We claim:
1. A pharmaceutical composition comprising one or more pharmaceutically acceptable diluents, excipients, or carriers; together with a compound having a formula selected from the group consisting of:
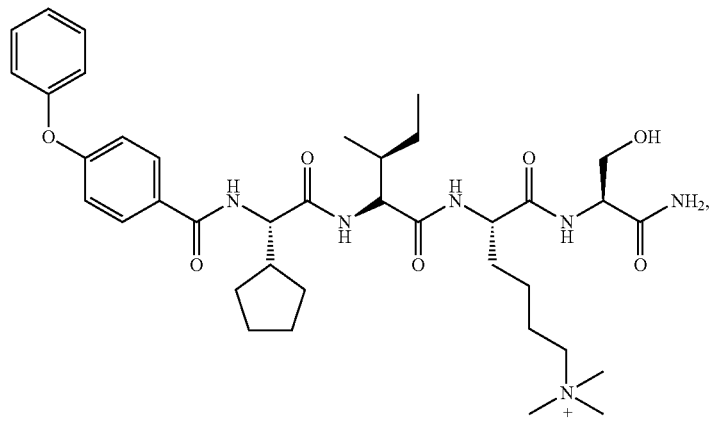
SW2_101B
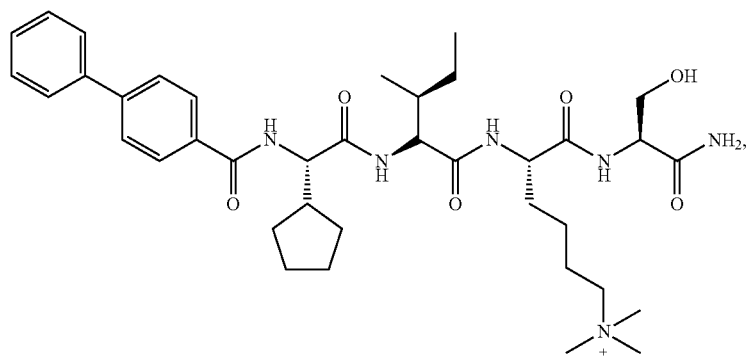
SW2_89
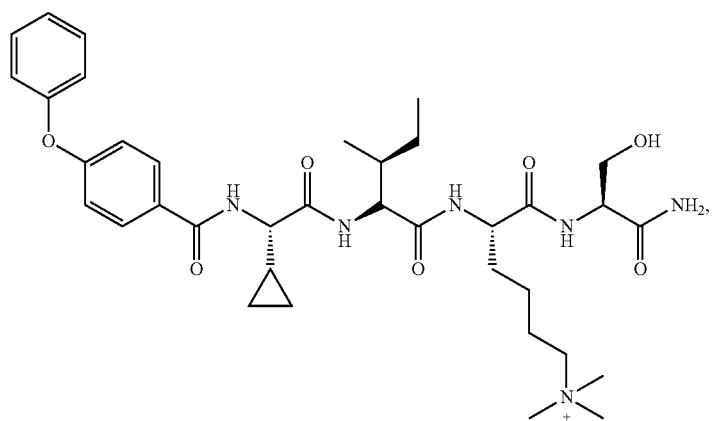
SW2_101F

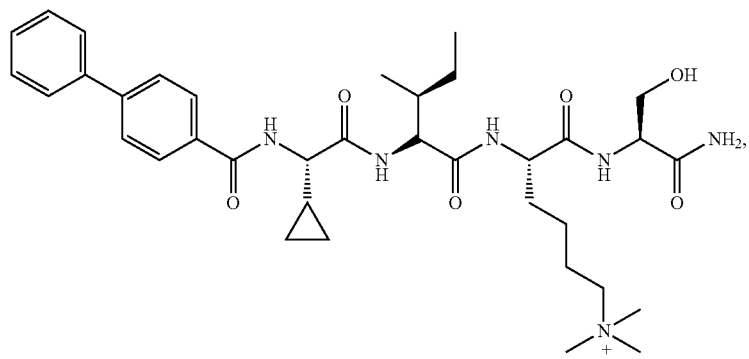
SW2_101A
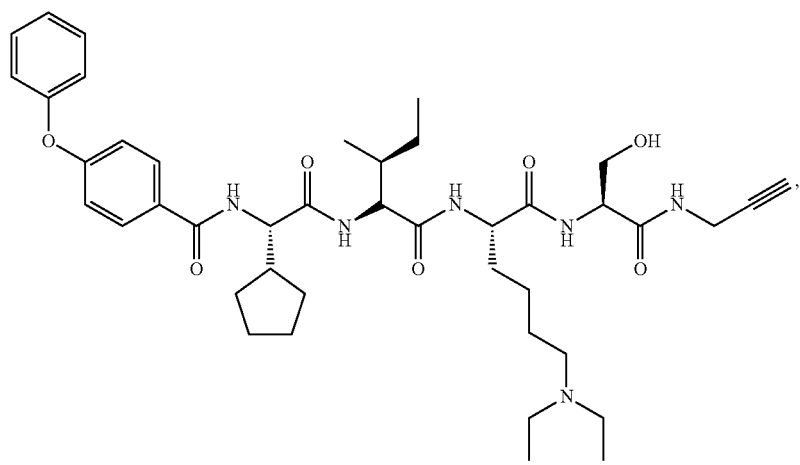
SW2_110A
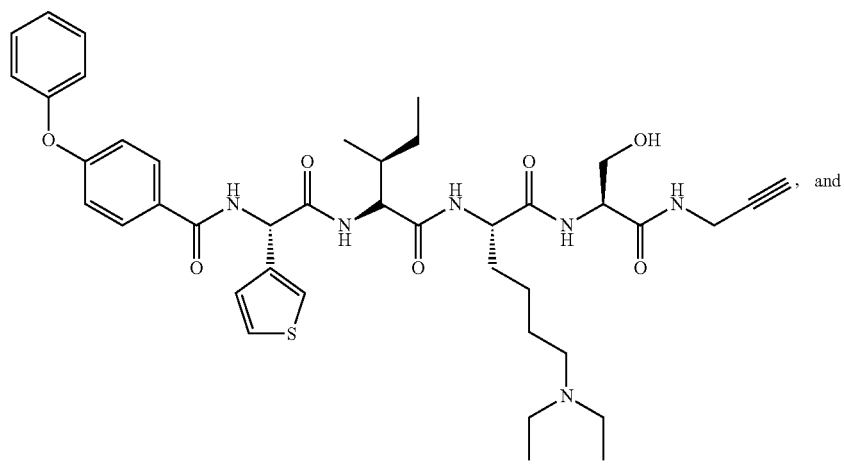
SW2_110B

-continued

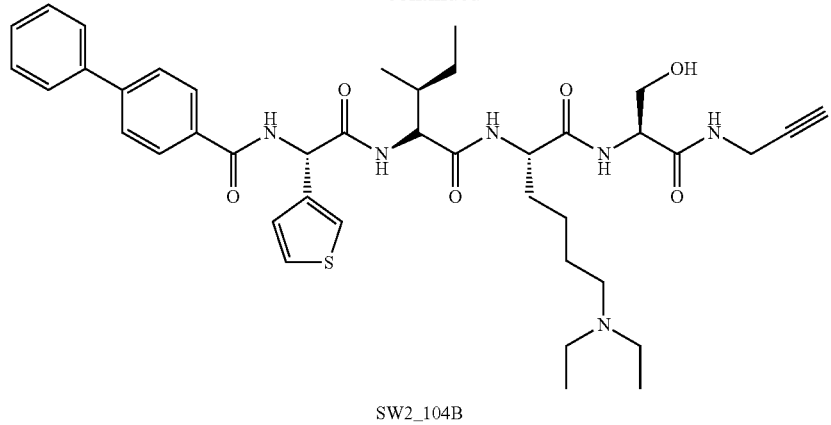

SW2_104B

2. The pharmaceutical composition of claim 1, wherein the compound is present in a therapeutically effective amount for treating a patient of cancer or leukemia, that is associated with activities of CBX8.

3. The pharmaceutical composition of claim 1, wherein the pharmaceutical composition is a dosage unit form.

4. The pharmaceutical composition of claim 1, wherein the pharmaceutical composition is formulated for administration by at least one of a route selected from the group consisting of: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally, subcutaneous, subdermal, sublingual, transdermal, and transmucosal.

5. The pharmaceutical composition of claim 4, wherein the pharmaceutical composition is formulated for administration by buccal.

6. The pharmaceutical composition of claim 4, wherein the pharmaceutical composition is formulated for administration by oral.

* * * * *

SEQUENCE LISTING

```
Sequence total quantity: 25
SEQ ID NO: 1            moltype =    length =
SEQUENCE: 1
000

SEQ ID NO: 2            moltype =    length =
SEQUENCE: 2
000

SEQ ID NO: 3            moltype = AA  length = 5
FEATURE                 Location/Qualifiers
REGION                  1..5
                        note = KED97
SITE                    1
                        note = X1 - 3-chloro-4-hydroxy-Tyr
SITE                    1
                        note = X1 - alpha amino acylation
SITE                    4
                        note = Lys - side chain N-trimethyl_Lys
SITE                    5
                        note = Ser - C-terminal amide
source                  1..5
                        mol_type = protein
                        organism = synthetic construct
SEQUENCE: 3
XVIKS                                                                    5

SEQ ID NO: 4            moltype =    length =
SEQUENCE: 4
000
```

```
SEQ ID NO: 5              moltype =    length =
SEQUENCE: 5
000

SEQ ID NO: 6              moltype =    length =
SEQUENCE: 6
000

SEQ ID NO: 7              moltype =    length =
SEQUENCE: 7
000

SEQ ID NO: 8              moltype =    length =
SEQUENCE: 8
000

SEQ ID NO: 9              moltype =    length =
SEQUENCE: 9
000

SEQ ID NO: 10             moltype =    length =
SEQUENCE: 10
000

SEQ ID NO: 11             moltype =    length =
SEQUENCE: 11
000

SEQ ID NO: 12             moltype =    length =
SEQUENCE: 12
000

SEQ ID NO: 13             moltype =    length =
SEQUENCE: 13
000

SEQ ID NO: 14             moltype = DNA  length = 27
FEATURE                   Location/Qualifiers
misc_feature              1..27
                          note = LMNB2 forward primer
source                    1..27
                          mol_type = other DNA
                          organism = synthetic construct
SEQUENCE: 14
ccgaatctct gaaatgaaag tccatgc                                      27

SEQ ID NO: 15             moltype = DNA  length = 26
FEATURE                   Location/Qualifiers
misc_feature              1..26
                          note = LMNB2 reverse primer
source                    1..26
                          mol_type = other DNA
                          organism = synthetic construct
SEQUENCE: 15
ttaaagatct gagggactcc tcagtc                                       26

SEQ ID NO: 16             moltype = DNA  length = 23
FEATURE                   Location/Qualifiers
misc_feature              1..23
                          note = CCND2 forward primer
source                    1..23
                          mol_type = other DNA
                          organism = synthetic construct
SEQUENCE: 16
actgtctgaa atgaaggtga agc                                          23

SEQ ID NO: 17             moltype = DNA  length = 23
FEATURE                   Location/Qualifiers
misc_feature              1..23
                          note = CCND2 reverse primer
source                    1..23
                          mol_type = other DNA
                          organism = synthetic construct
SEQUENCE: 17
gatttgatgg acacttggtt tgt                                          23

SEQ ID NO: 18             moltype = DNA  length = 21
FEATURE                   Location/Qualifiers
misc_feature              1..21
```

```
                         note = GATA6 forward primer
source                   1..21
                         mol_type = other DNA
                         organism = synthetic construct
SEQUENCE: 18
gcctctccat tccagagttt t                                             21

SEQ ID NO: 19            moltype = DNA   length = 20
FEATURE                  Location/Qualifiers
misc_feature             1..20
                         note = GATA6 reverse primer
source                   1..20
                         mol_type = other DNA
                         organism = synthetic construct
SEQUENCE: 19
tccagaaacc gttctcatcc                                               20

SEQ ID NO: 20            moltype = DNA   length = 23
FEATURE                  Location/Qualifiers
misc_feature             1..23
                         note = RUNX3 forward primer
source                   1..23
                         mol_type = other DNA
                         organism = synthetic construct
SEQUENCE: 20
tcaaaaggca tccgcctctc cgt                                           23

SEQ ID NO: 21            moltype = DNA   length = 23
FEATURE                  Location/Qualifiers
misc_feature             1..23
                         note = RUNX3 reverse primer
source                   1..23
                         mol_type = other DNA
                         organism = synthetic construct
SEQUENCE: 21
aaggatgcac ctgccgggaa ttg                                           23

SEQ ID NO: 22            moltype = DNA   length = 20
FEATURE                  Location/Qualifiers
misc_feature             1..20
                         note = HOXA9 forward primer
source                   1..20
                         mol_type = other DNA
                         organism = synthetic construct
SEQUENCE: 22
ggcccaggac cgagatactt                                               20

SEQ ID NO: 23            moltype = DNA   length = 22
FEATURE                  Location/Qualifiers
misc_feature             1..22
                         note = HOXA9 reverse primer
source                   1..22
                         mol_type = other DNA
                         organism = synthetic construct
SEQUENCE: 23
cgctcacgga caatctagtt gt                                            22

SEQ ID NO: 24            moltype = DNA   length = 25
FEATURE                  Location/Qualifiers
misc_feature             1..25
                         note = B2M forward primer
source                   1..25
                         mol_type = other DNA
                         organism = synthetic construct
SEQUENCE: 24
tgctgtctcc atgtttgatg tatct                                         25

SEQ ID NO: 25            moltype = DNA   length = 22
FEATURE                  Location/Qualifiers
misc_feature             1..22
                         note = B2M reverse primer
source                   1..22
                         mol_type = other DNA
                         organism = synthetic construct
SEQUENCE: 25
tctctgctcc ccacctctaa gt                                            22
```